(12) United States Patent  
Matsumoto et al.

(10) Patent No.: US 7,854,890 B2  
(45) Date of Patent: Dec. 21, 2010

(54) ANALYTICAL TOOL, ANALYTICAL TOOL PACK, CARTRIDGE INCLUDING PLURALITY OF PACKS, METHOD OF MAKING ANALYTICAL TOOL PACK, ANALYZER, AND MECHANISM FOR TAKING OUT OBJECT

(75) Inventors: Daisuke Matsumoto, Kyoto (JP); Eisaku Oshiman, Kyoto (JP); Hidefumi Komuro, Kyoto (JP)

(73) Assignee: Arkray, Inc., Kyoto (JP)

( * ) Notice: Subject to any disclaimer, the term of this patent is extended or adjusted under 35 U.S.C. 154(b) by 1134 days.

(21) Appl. No.: 10/515,713

(22) PCT Filed: May 19, 2003

(86) PCT No.: PCT/JP03/06240

§ 371 (c)(1), (2), (4) Date: Nov. 23, 2004

(87) PCT Pub. No.: WO03/100408

PCT Pub. Date: Dec. 4, 2003

(65) Prior Publication Data

US 2005/0221470 A1    Oct. 6, 2005

(30) Foreign Application Priority Data

May 23, 2002 (JP) .............................. 2002-149481
May 23, 2002 (JP) .............................. 2002-149482

(51) Int. Cl.
*G01N 33/00* (2006.01)

(52) U.S. Cl. ........................... 422/63; 422/99; 422/102

(58) Field of Classification Search ................... 422/63, 422/99, 102
See application file for complete search history.

(56) References Cited

U.S. PATENT DOCUMENTS

| 5,997,811 | A | * | 12/1999 | Esposito | ........................ 422/1 |
| 6,599,406 | B1 | | 7/2003 | Kawanaka et al. | |
| 6,827,829 | B2 | | 12/2004 | Kawanaka et al. | |
| 7,470,400 | B2 | * | 12/2008 | Uchigaki et al. | .............. 422/63 |
| 7,473,398 | B2 | * | 1/2009 | Bhullar et al. | ........... 422/82.01 |

FOREIGN PATENT DOCUMENTS

EP    0 732 590    9/1996

(Continued)

*Primary Examiner*—Sam P Siefke
(74) *Attorney, Agent, or Firm*—Hamre, Schumann, Mueller & Larson, P.C.

(57) ABSTRACT

The present invention relates to an analytical tool pack (1) including an analytical tool (13) accommodated in one or between a plurality of sealing sheets (12a, 12b). The analytical tool pack (1) includes a stopper portion (146) for holding the analytical tool (13) with the analytical tool (13) caused to project from the sealing sheets (12a, 12b). Preferably, the analytical tool pack (1) further comprises a base film (14) bonded to the sealing sheets (12a, 12b). For example, the stopper portion (146) comprises the bonded portion of the sealing sheets (12a, 12b) and the base film (14). The present invention further relates to an analyzer which uses the analytical tool pack (1). The analyzer comprises an opening mechanism for making a cut (15) in the analytical tool pack (1), and a pushing mechanism for moving the analytical tool (13) relative to the sealing sheets (12a, 12b) to cause the analytical tool (13) to project through the cut (15).

16 Claims, 40 Drawing Sheets

| | FOREIGN PATENT DOCUMENTS | |
|---|---|---|
| EP | 1 118 856 | 7/2001 |
| JP | 8-262026 | 11/1996 |
| JP | 2000-19147 | 1/2000 |
| JP | 2000-171427 | 6/2000 |
| JP | 2000-314711 | 11/2000 |
| JP | 2001-033417 | 2/2001 |
| JP | 2001-033418 | 2/2001 |
| JP | 2001-141686 | 5/2001 |
| JP | 2001-281199 | 10/2001 |
| JP | 2001-337066 | 12/2001 |
| WO | WO 99/05516 | 2/1999 |

\* cited by examiner

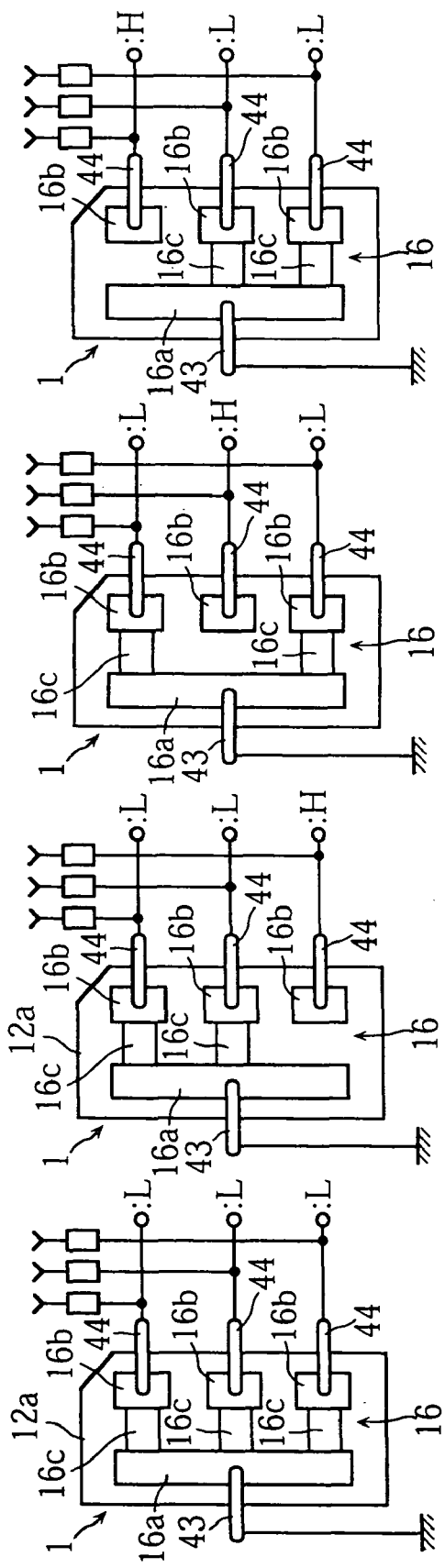

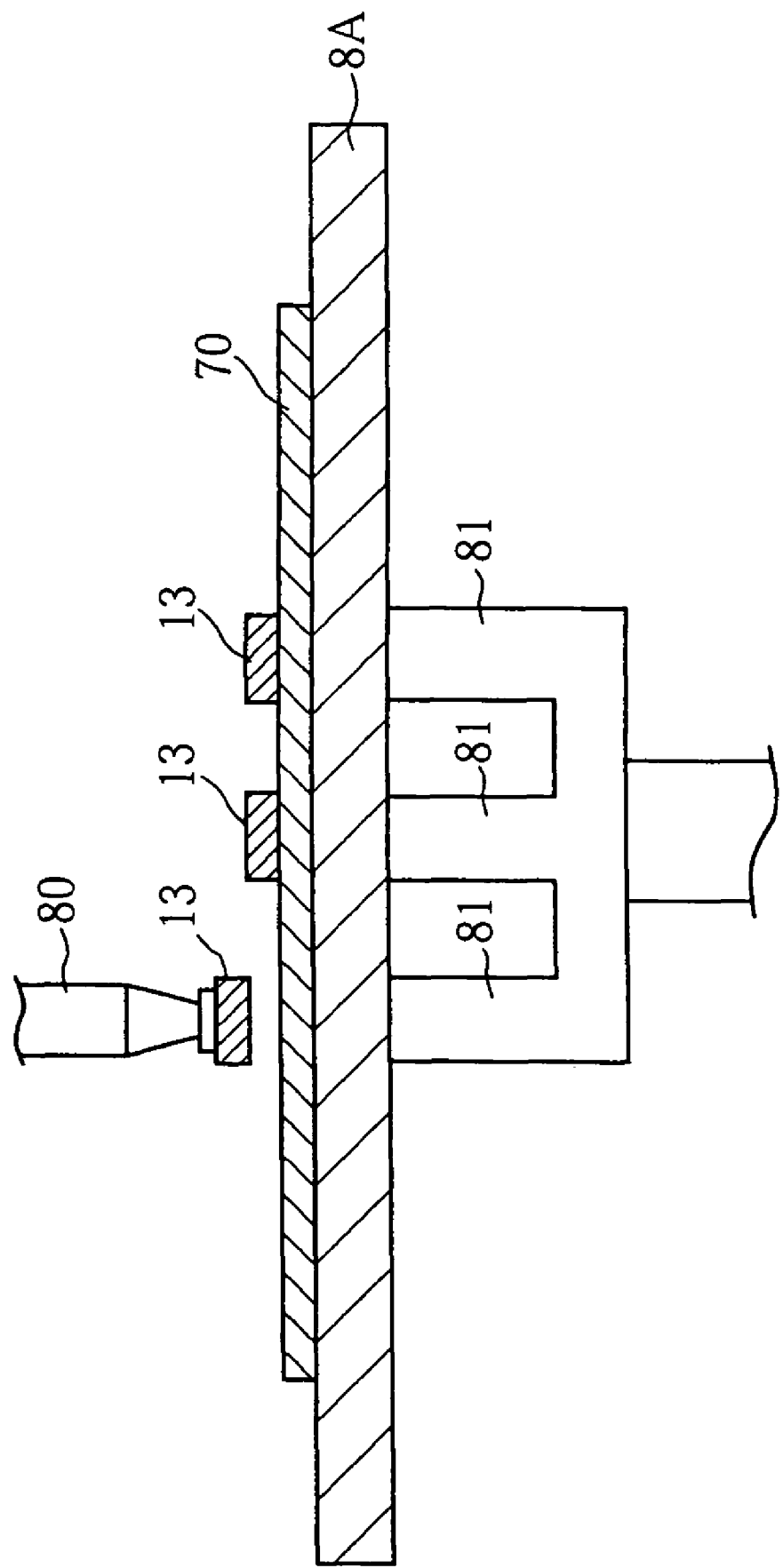

ANALYTICAL TOOL, ANALYTICAL TOOL PACK, CARTRIDGE INCLUDING PLURALITY OF PACKS, METHOD OF MAKING ANALYTICAL TOOL PACK, ANALYZER, AND MECHANISM FOR TAKING OUT OBJECT

TECHNICAL FIELD

The present invention mainly relates to a technique for analyzing a particular component in a sample liquid. It also relates to a technique for taking out an object from an object-containing pack such as an analytical tool pack.

BACKGROUND ART

For diabetics, it is preferable to regularly measure his or her own glucose level in blood and take appropriate measures such as medicine administration in accordance with the measurements. JP-A-H08-262026 and JP-A-2001-33418, for example, disclose devices for measuring a blood glucose level.

As shown in FIG. 45, in a first device disclosed in JP-A-H08-262026, when an operation portion 91 provided on a housing 90 is operated, a sensor S partially projects through an opening 90a formed at the front end of the housing 90. In the first device, when the blood of the user is applied to a predetermined portion of the sensor S, the measurement circuit (not shown) in the housing 90 computes the glucose level in blood, and the measurement result is displayed on a display 92.

As shown in FIG. 46, in the first device, the sensor S is accommodated in the housing 90 as a package (cartridge) 95. The package 95 includes a base member 95a formed with a plurality of radially extending recesses 96, and a film 95b bonded to the base member. Each of the recess 96 serves to accommodate a sensor S.

As shown in FIGS. 47A and 47B, when the operation portion 91 is operated to take out the sensor S, a blade 97a breaks through part of the film 95b of the package 95 and then pushes the rear end of the sensor S toward the outer circumference of the package 95. As a result, the sensor S breaks through part of the film 95b and is pushed to the opening 90a of the housing 90.

With such a structure, by setting the package 95 in the housing 90, measurement of the glucose level in blood can be performed a plurality of times by successively using the plurality of sensors S.

In the first device, when the sensor S is taken out from the package 95, the sensor S itself breaks through the film 95b. Therefore, the front end of the sensor S needs to be made sharp. However, since the user may touch the front end of the sensor S, the sharp front end may cause the user to fear and hence is not preferable. Moreover, the sensor S may not break the film 95b easily, so that taking out of the sensor S by breaking the film 95b by the sensor S itself is sometimes difficult.

In a second device disclosed in JP-A-2001-33418, a film member accommodating a sensor is placed in a device. The sensor is taken out by breaking the film and used for measuring a blood glucose level, for example.

In the second device, the sensor is taken out from the film member, and the measurement is performed. Therefore, the number of parts which need be disposed of after the measurement is large. That is, two parts, i.e. the empty film member and the sensor need be disposed of. Moreover, since the timing at which the film becomes unnecessary does not coincide with the timing at which the sensor becomes unnecessary, the two parts need be disposed of separately, which is inconvenient.

DISCLOSURE OF THE INVENTION

A first object of the present invention is to make it possible to properly take out a stored object such as a sensor without making sharp the front end of the stored object. A second object of the present invention is to reduce the burden of disposing of the used parts after the analysis.

According to a first aspect of the present invention, there is provided an analytical tool pack comprising a wrapping member made of a sealing sheet, and an analytical tool accommodated in the wrapping member. The analytical tool pack further comprises a stopper portion for holding the analytical tool with the analytical tool caused to project from the wrapping member.

The sealing sheet may comprise a pair of sheet elements or a single sheet. When the sealing sheet comprises a pair of sheet elements, the wrapping member is formed by directly or indirectly bonding the paired sheet elements to each other at the peripheries thereof. When the sealing sheet comprises a single sheet, the wrapping member may be formed by folding the sheet.

Preferably, the wrapping member further comprises a base film bonded to the sealing sheet. For example, in this case, the stopper portion comprises the bonded portion of the sealing sheet and the base film.

Preferably, the analytical tool includes an engagement portion for engaging with the stopper portion.

Preferably, at least one of the sealing sheet and the base film retains desiccant. The desiccant may be contained in the sealing sheet and the base film or applied to the surfaces thereof. Alternatively, the desiccant may be held by the base film or the analytical tool.

Preferably, the analytical tool is caused to project through a cut formed in the sealing sheet by using a cutter, and the base film includes a through-hole for allowing the insertion of the cutter.

Preferably, the analytical tool includes an end which is caused to project through a cut formed in the sealing sheet by using a cutter, and the end is entirely rounded.

Preferably, the analytical tool is moved relative to the wrapping member by using a pushing member, the base film includes a through-hole for allowing the movement of the pushing member, and the analytical tool further includes an engagement portion for engaging the pushing member.

The through-hole of the base member may have an outline which is in the form of a closed loop or an outline which is partially cut away (i.e., part of the through-hole is open to a side of the base film).

Preferably, the analytical tool includes a substrate, a plurality of electrodes formed on the substrate, and a plurality of holes each for partially exposing a respective one of the electrodes selectively. The electrodes may be continuously exposed.

Preferably, the analytical tool pack of the present invention further comprises an information providing portion for outputting information relating to the analytical tool. For example, the information providing portion is capable of outputting information by the combination of conduction/non-conduction between a plurality of pairs of conductors, or by correlation with a resistance between conductors, or by correlation with locations where a projection and a recess are formed.

For example, the analytical tool pack in use is loaded in an accommodation portion of an analyzer. Preferably, in this case, the analytical tool pack further comprises a pack orientation checker for preventing improper loading of the analytical tool into the accommodation portion. Preferably, the analytical tool caused to project from the wrapping member can be restored in the wrapping member for accommodation again.

According to a second aspect of the present invention, there is provided an analytical tool pack comprising a wrapping member, and an analytical tool accommodated in the wrapping member, the analytical tool pack further comprising an information providing portion for outputting information relating to the analytical tool.

For example, the information providing portion is capable of outputting information by the combination of conduction/non-conduction between a plurality of pairs of conductors, or by correlation with a resistance between conductors, or by correlation with locations where a projection and a recess are formed. Preferably, the information providing portion is provided at an obverse surface of the wrapping member.

According to a third aspect of the present invention, there is provided an analytical tool accommodated in a wrapping member for providing an analytical tool pack and caused to project from the wrapping member in use, the analytical tool pack including a stopper portion for holding the analytical tool. The analytical tool includes an engagement portion for engaging with the stopper portion.

According to a fourth aspect of the present invention, there is provided analytical tool accommodated in a wrapping member for providing an analytical tool pack and caused to project from the wrapping member in use, the analytical tool pack being capable of moving the analytical tool relative to the wrapping member by using a pushing member. The analytical tool includes an engagement portion for engaging with the pushing member.

According to a fifth aspect of the present invention, there is provided an analytical tool accommodated in a wrapping member for providing an analytical tool pack and including an end which is caused to project from the wrapping member in use of the analytical tool, and the end is entirely rounded.

According to a sixth aspect of the present invention, there is provided a cartridge including a container accommodating a plurality of analytical tool packs, each of the analytical tool packs including a wrapping member, and an analytical tool accommodated in the wrapping member. The container is formed with a through-hole communicating with the inside of the container and utilized for pushing out the analytical tool pack accommodated in the container.

Preferably, the plurality of analytical tool packs are bundled in the container. For example, the analytical tool packs are bundled together by applying an adhesive element on a surface of each tool pack and stacking the packs for bonding together, by maintaining the stacked state of tool packs by using a member in the form of a strip, or connecting side surfaces of the stacked analytical tool packs by using an adhesive sheet.

According to a seventh aspect of the present invention, there is provided a method of making an analytical tool pack comprising the steps of placing an analytical tool on a punch film or a sealing film, and bonding the sealing film to the punch film. The analytical tool is kept at an appropriate position relative to the punch film at least for a time period from when the placing step is completed and till when the bonding step is started.

For example, the position keeping is performed by using a suction unit.

According to an eighth aspect of the present invention, there is provided a method of making an analytical tool pack comprising fixing an analytical tool to a sealing film or a punch film. The fixing step is performed simultaneously with respect to a plurality of analytical tools by using a plurality of pressing heads, and the pressing heads are capable of setting respective heights individually.

According to a ninth aspect of the present invention, there is provided an analyzer for analyzing a sample by using an analytical tool pack including a wrapping member and an analytical tool accommodated in the wrapping member, the analysis being performed with the analytical tool caused to project from the wrapping member. The analyzer comprises an opening mechanism for making a cut in the wrapping member, and a pushing mechanism for moving the analytical tool relative to the wrapping member to cause the analytical tool to project through the cut.

Preferably, the analyzer of the present invention obtains output relating to analysis results from the analytical tool, with the analytical tool caused to project from the wrapping member.

For example, the pushing mechanism comprises a first and a second members which are movable relative to each other in a first direction, and a pushing member which is movable in a second direction crossing the first direction in accordance with the relative movement between the first and the second members, the pushing member serving to move the analytical tool relative to the wrapping member.

For example, the pushing member is pivotally fixed to the first member while being connected to the second member for relative movement to the second member. Preferably, in this case, the second member is provided with a guide for moving a portion connected to the pushing member in the second direction. Preferably, the pushing member comprises a blade.

For example, the pushing mechanism further comprises a holder for moving the wrapping member together with the first member or the second member. Preferably, in this case, the pushing mechanism further comprises a releaser for releasing the holding of the analytical tool by the holder.

For example, the releaser increases the distance between the first member and the second member in the second direction when a particular positional relationship is established between the first member and the second member.

Preferably, the analyzer of the present invention further comprises a restorer for restoring the analytical tool projected from the wrapping member into the wrapping member for accommodation again.

Preferably, the restorer is provided by the pushing member.

In the analyzer of the present invention, the second member performs reciprocating movement between a first predetermined position and a second predetermined position relative to the first member twice in a single sample analysis operation. In this case, the pushing member engages and moves the analytical tool to cause the analytical tool to project from the wrapping member when the second member moves from the first position toward the second position in the first reciprocating movement. On the other hand, when the pushing member engages and moves the analytical tool to restore the analytical tool into the wrapping member when the second member moves from the second position toward the first position in the second reciprocating movement.

In this case, it is preferable that the second member is provided with a cam groove for controlling the operation of the pushing member. For example, the cam groove has a configuration which makes the pushing member operate differently during the first reciprocating movement and during the second reciprocating movement.

As the analytical tool pack, use may be made of one in which the wrapping member comprises a sealing sheet, and a base film formed with a through-hole and bonded to the sealing sheet. In this case, the opening mechanism includes a cutter for making a cut in the wrapping member, and the cutter and the pushing member move through the through-hole.

For example, the opening mechanism includes an operation button, and a cutter which moves together with the operation button.

For example, the analyzer of the present invention may further comprise an accommodation portion into which the analytical tool pack is to be loaded. Preferably, in this case, the accommodation portion includes a pack orientation checker for preventing improper loading of the analytical tool pack into the accommodation portion.

For example, the analyzer of the present invention comprises a device body including an accommodation portion for accommodating a plurality of analytical tool packs, and a lid connected to the device body. The analytical tool packs are accommodated while being pressed against each other by a pressing member. Preferably, in this case, the lid is connected to the pressing member to release the pressing of the analytical tool packs in opening the accommodation portion.

According to a tenth aspect of the present invention, there is provided an object taking-out mechanism for taking out an object from a pack in which the object is accommodated in a wrapping member. The mechanism comprises an opening mechanism for making a cut in the wrapping member, and a pushing mechanism for pushing out the object through the cut.

BRIEF DESCRIPTION OF THE DRAWINGS

FIG. 4A is a sectional view of the analyzer shown in FIG. 1, whereas

FIG. 5A is a sectional view taken along lines Z1-Z1 in FIG. 4A, whereas

FIG. 10A is a sectional view taken along lines Z2-Z2 in FIG. 9, whereas

FIG. 14A-14H each is a schematic view for describing the manner of recognizing the information relating to the biosensor by utilizing the information providing portion.

FIG. 18A is a sectional view taken along lines Z4-Z4 in FIG. 16, whereas

FIG. 21 is a sectional view taken along lines Z6-Z6 in FIG. 19.

FIG. 37A is a sectional view showing a measurement mechanism in feeding a biosensor, whereas

FIG. 38A is a sectional view showing a measurement mechanism in feeding a biosensor, whereas

FIG. 39A is a sectional view showing a measurement mechanism in which the blade is escaping, whereas

FIG. 40A is a sectional view showing a measurement mechanism in which the biosensor is being returned, whereas

BEST MODE FOR CARRYING OUT THE INVENTION

Preferred embodiments of the present invention will be described below with reference to the accompanying drawings.

Figure 1:
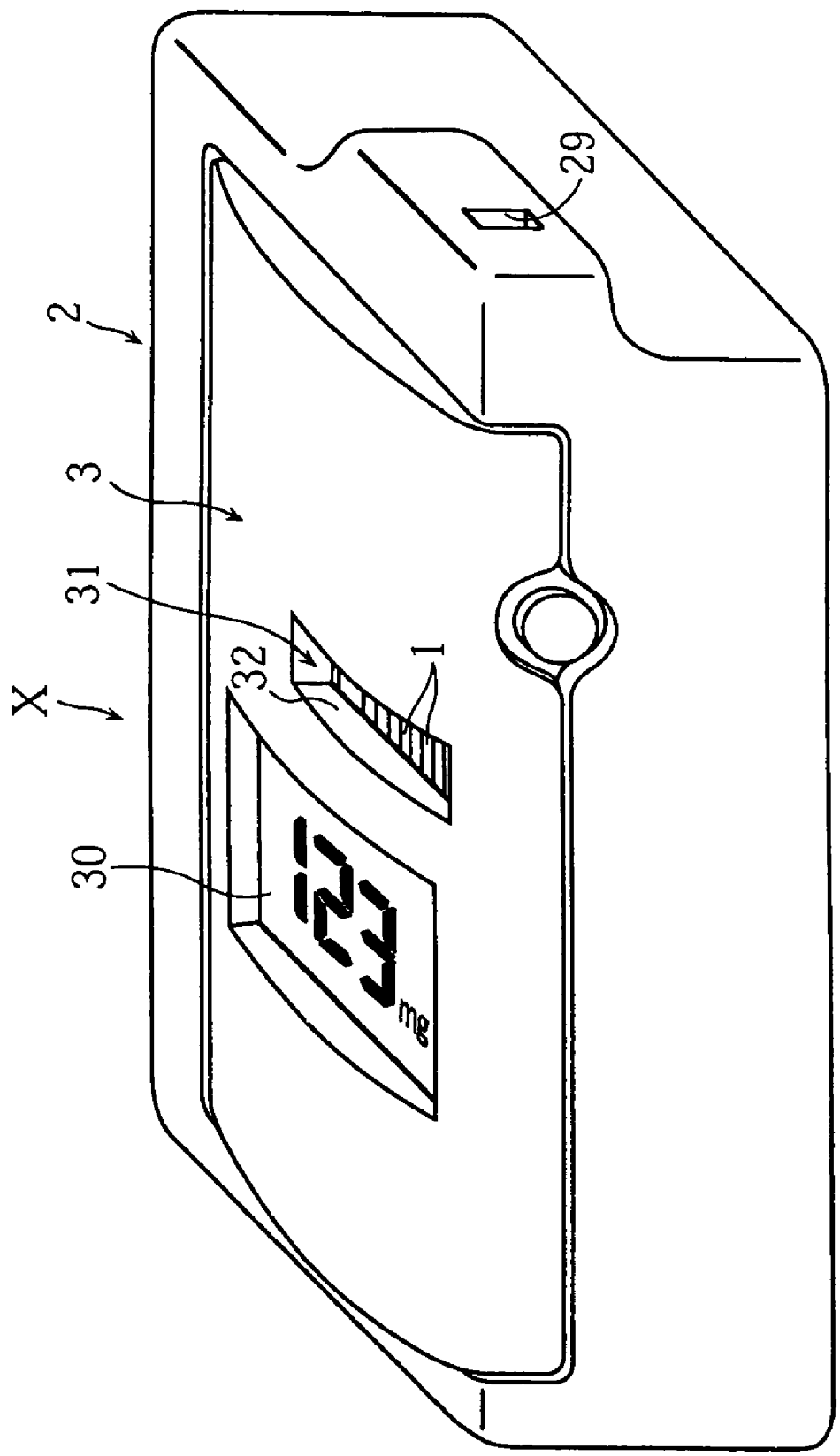
FIG. 1 is an entire perspective view showing an analyzer according to a first embodiment of the present invention.

A sensor pack according to the present invention encloses a biosensor and is used for analyzing a sample liquid such as blood supplied to the biosensor, specifically, for measuring e.g. the glucose level in blood. In use, the sensor pack is set to an analyzer X shown in FIGS. 1 and 2.

The analyzer X comprises a device body 2 formed with an accommodation portion 20 for accommodating a sensor pack 1, and comprises a lid 3 which is attached to the device body 2 in an openable and closeable manner. The lid 3 is provided with a display 30 and a window 31. The display 30, serving to show measurement results, comprises an LCD, for example. The window 31 is used for checking the number of remaining sensor packs 1 in the accommodation portion 20. The window 31 may be formed by covering an opening 32 provided in the lid 3 by a transparent member 33.

Figure 3:
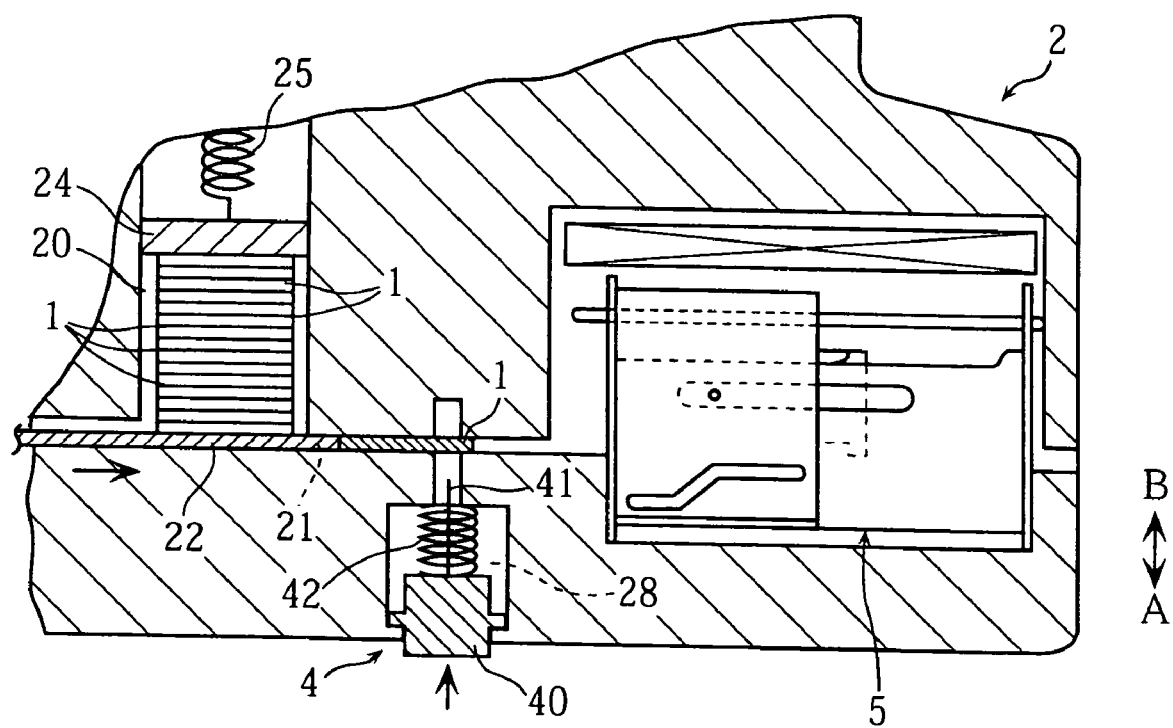
FIG. 3 is a sectional view showing a principal portion of the analyzer of FIG. 1.

As shown in FIG. 3, in addition to the accommodation portion 20, the device body 2 includes an opening mechanism 4, a measurement mechanism 5, a passage 21 extending from the accommodation portion 20 to the measurement mechanism 5 through a wait position (stop position at which the opening mechanism 4 performs the opening operation), and a feeder 22 for moving the sensor pack 1 within the passage 21.

Figure 2:
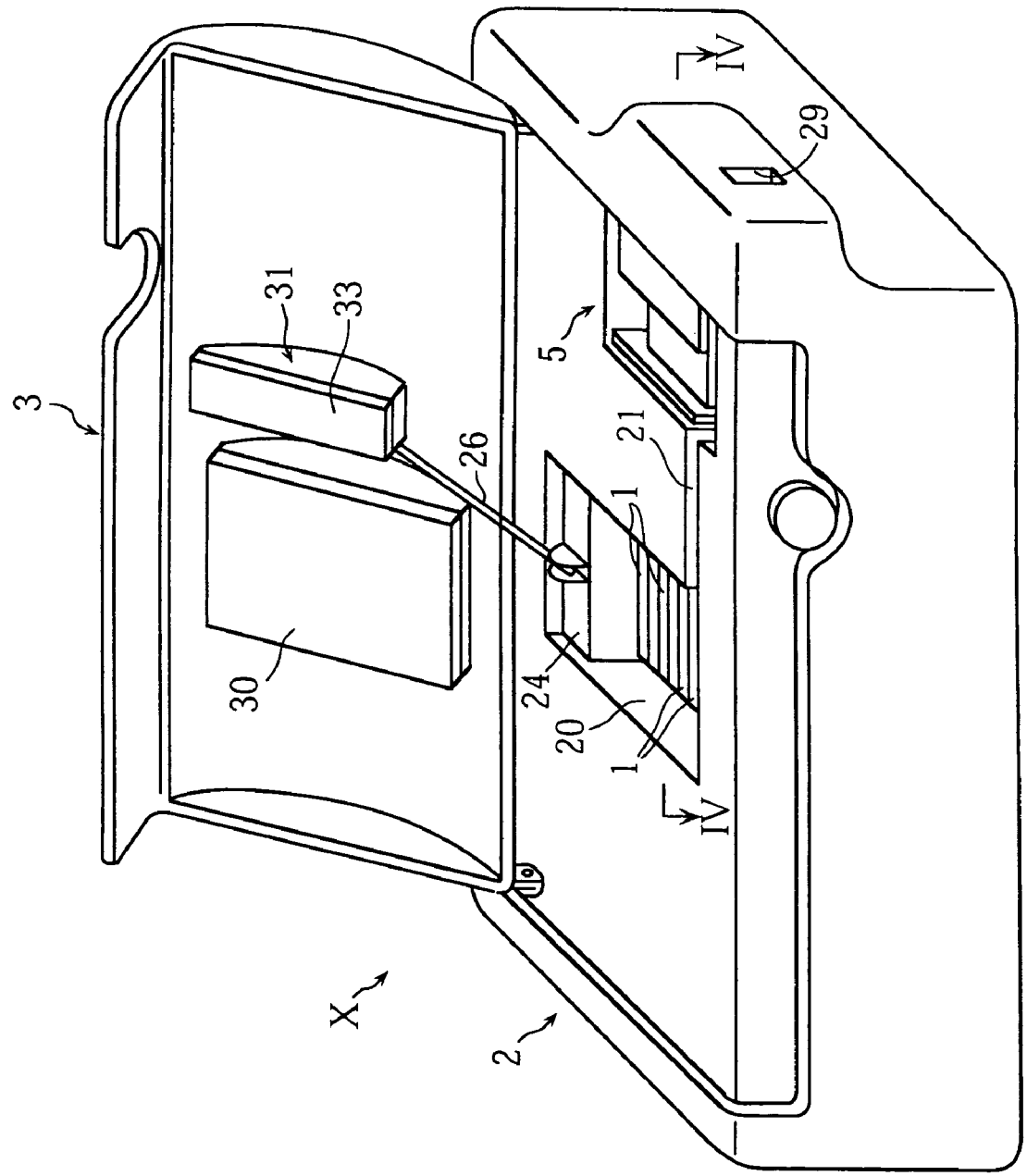
FIG. 2 is a perspective view showing the analyzer of FIG. 1 in the state in which the lid is opened.

As shown in FIGS. 2 through 4, the accommodation portion 20 serves to accommodate a plurality of sensor packs 1 as stacked. As shown in FIG. 5A, the accommodation portion 20 is formed with a tapered portion 23 for preventing improper loading of the sensor packs (loading of the sensor packs 1 upside down or inside out). Though not clearly shown in the figure, the tapered portion 23 extends in a direction perpendicular to the sheet surface. On the other hand, each sensor pack 1 is formed with a tapered surface 10 provided by chamfering one of the corners. Therefore, the sensor pack 1 can be loaded properly in the accommodation portion 20 when the tapered surface 10 of the sensor pack 1 is aligned with respect to the tapered portion 23 of the accommodation portion 20. The sensor pack 1 cannot be loaded properly without such alignment. Thus, improper loading of the sensor pack 1 is prevented. The means for preventing the improper loading of the sensor pack 1 is not limited to the example shown in FIG. 5. For example, as shown in FIG. 5B', the accommodation portion 20 may be formed with a projection 23' while the sensor pack 1 is formed with a recess 10, or another arrangement may be employed.

The accommodation portion 20 further accommodates a pushing member 24. The pushing member 24 is fixed to the device body 2 via a resilient member 25 (illustrated as a coil spring in FIGS. 3 and 4). By the resilient force of the resilient member 25, the sensor pack 1 is pushed in the direction indicated by the arrow A in the figure. The sensor pack 1, thus held in the pushed state, is then held at the wait position and finally transferred to the measurement mechanism 5 by the movement of the feeder 22. Preferably, the feeder 22 is moved automatically by a motor, for example. Alternatively, the device body 2 or the lid 3 may be provided with an operation knob projecting therefrom and movable together with the feeder 22, so that the feeder 22 is moved manually by moving the operation knob.

Figure 4A:
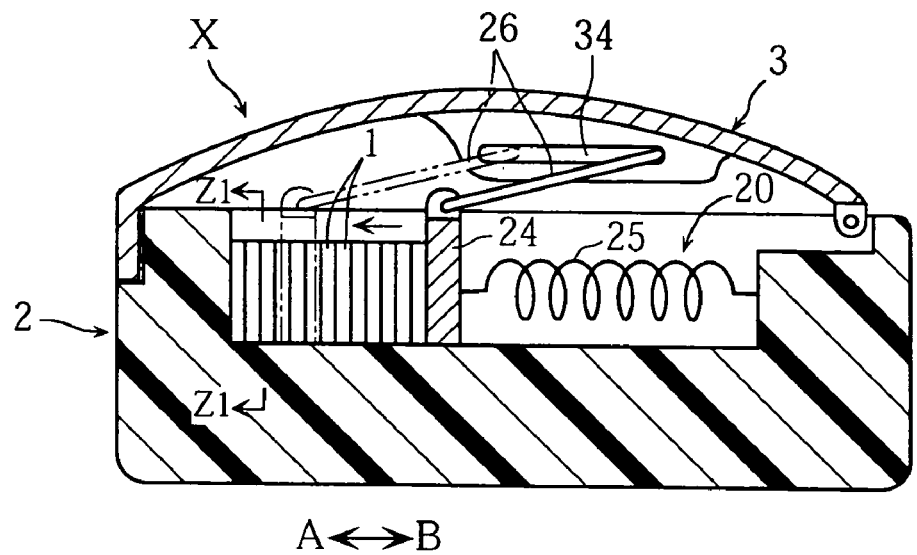
Figure 4B:
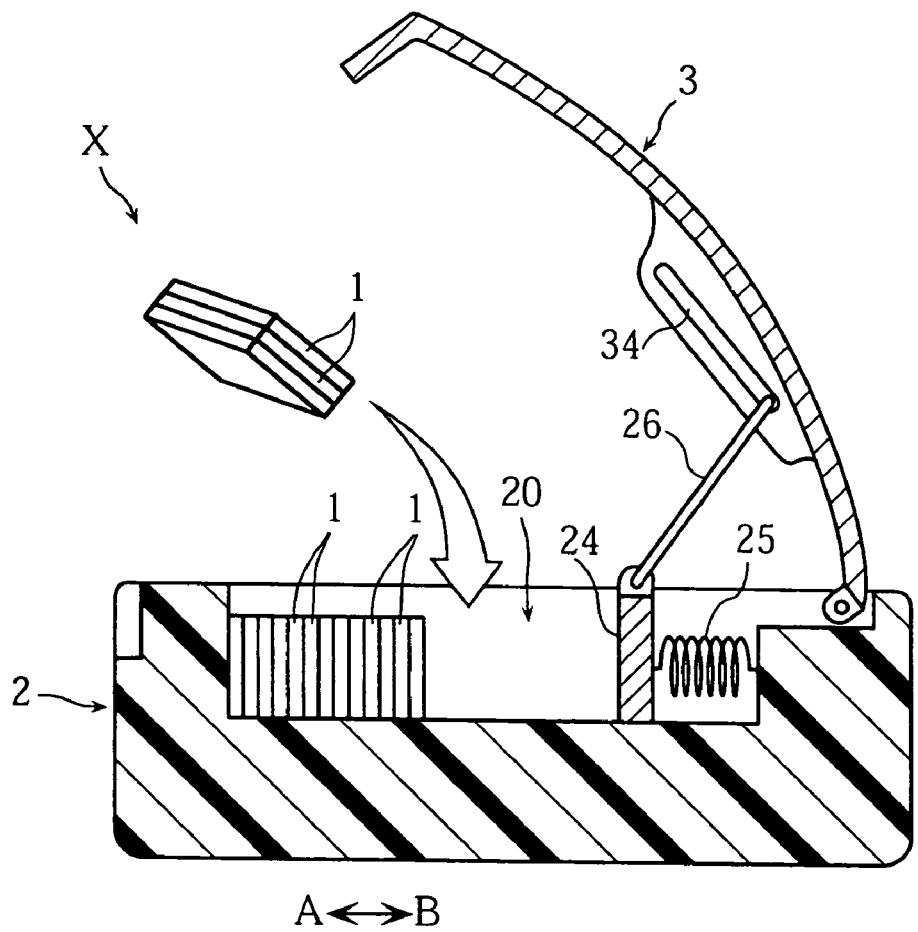
FIG. 4B is a sectional view of the state in which the lid is opened in the analyzer.
Figure 5A:
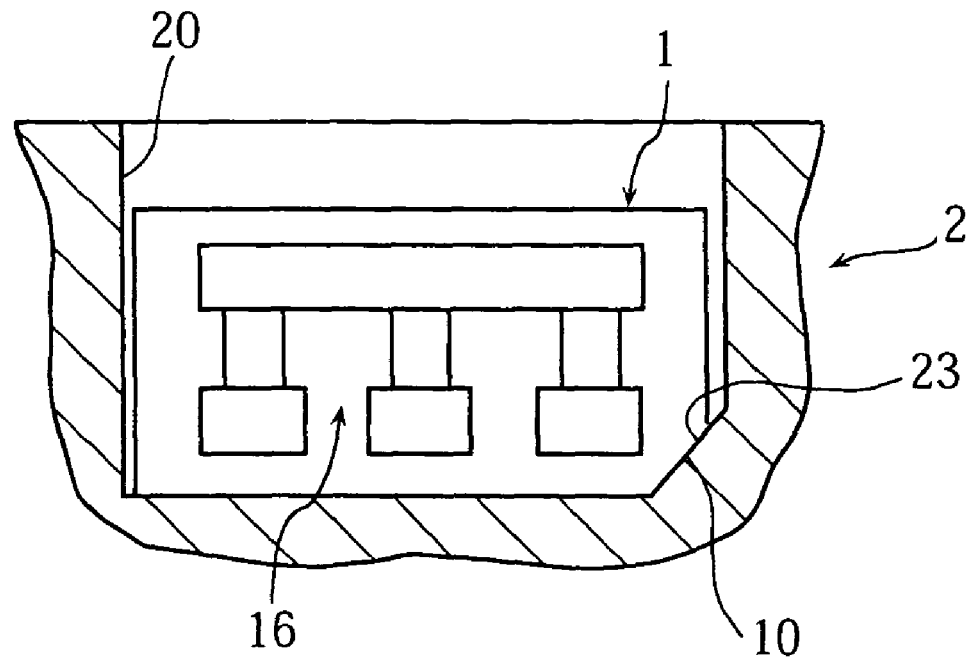
Figure 5B:
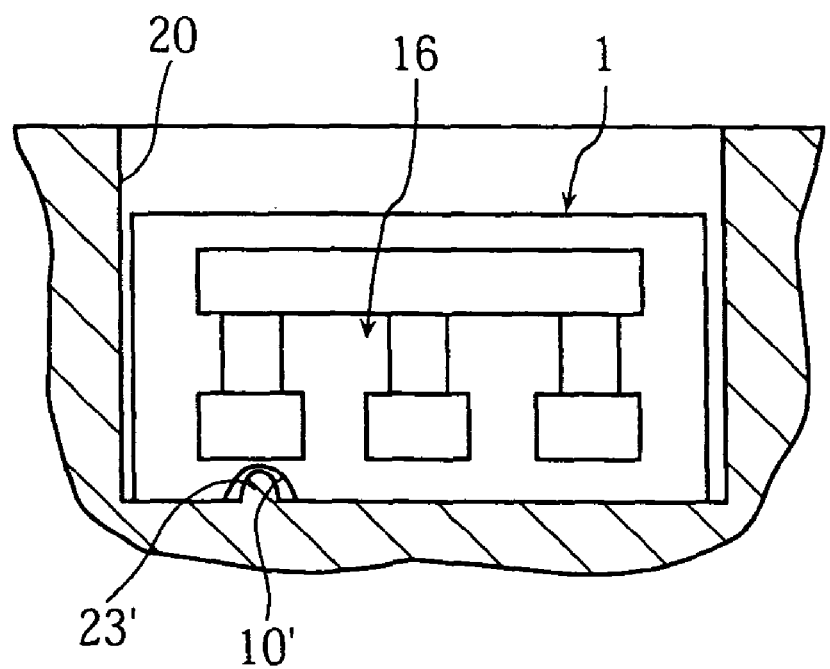
FIG. 5B is a sectional view corresponding to FIG. 5A for showing another example of sensor pack.

As shown in FIGS. 4A and 4B, the pushing member 24 is connected to the lid 3 via a rod 26. The rod 26 has a first end connected to the pushing member 24 for pivotal movement and a second end connected to the lid 3 via an elongated hole 34 formed in the lid 3. As shown in FIG. 4A, the elongated hole 34 extends in the direction indicated by the arrows AB in the state in which the lid 3 is closed. Therefore, when the lid 3 is closed, the second end of the rod 26 can move smoothly within the elongated hole 34. Accordingly, following the movement of the pushing member 24, the rod 26 can move in the direction indicated by the arrows AB in the figure, whereby the pushing member 24 can maintain the state for properly pushing the sensor pack 1.

As shown in FIG. 4B, in opening or closing the lid 3, the direction in which the elongated hole 34 extends becomes non-parallel to the direction indicated by the arrows AB. In this state, the second end of the rod 26 cannot move smoothly within the elongated hole 34. Therefore, when the lid 3 is opened, the push member 24, following the movement of the lid 3, moves in the direction indicated by the arrow B, whereby a space is defined between the push member 24 and the sensor pack 1. The space is utilized for additionally loading a sensor pack 1 into the device body 2.

Figure 6:
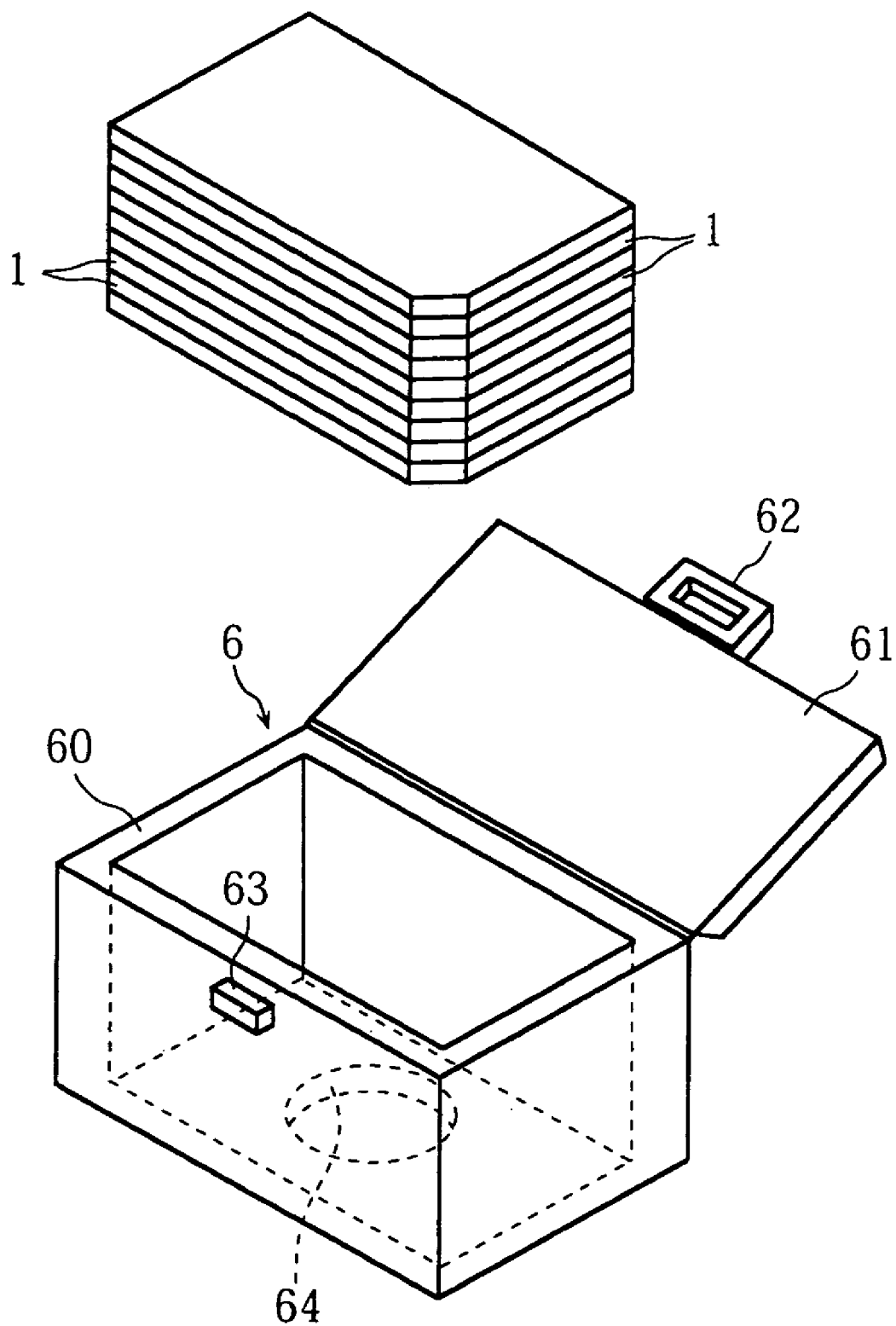
FIG. 6 is an exploded perspective view of a sensor cartridge.
Figure 7:
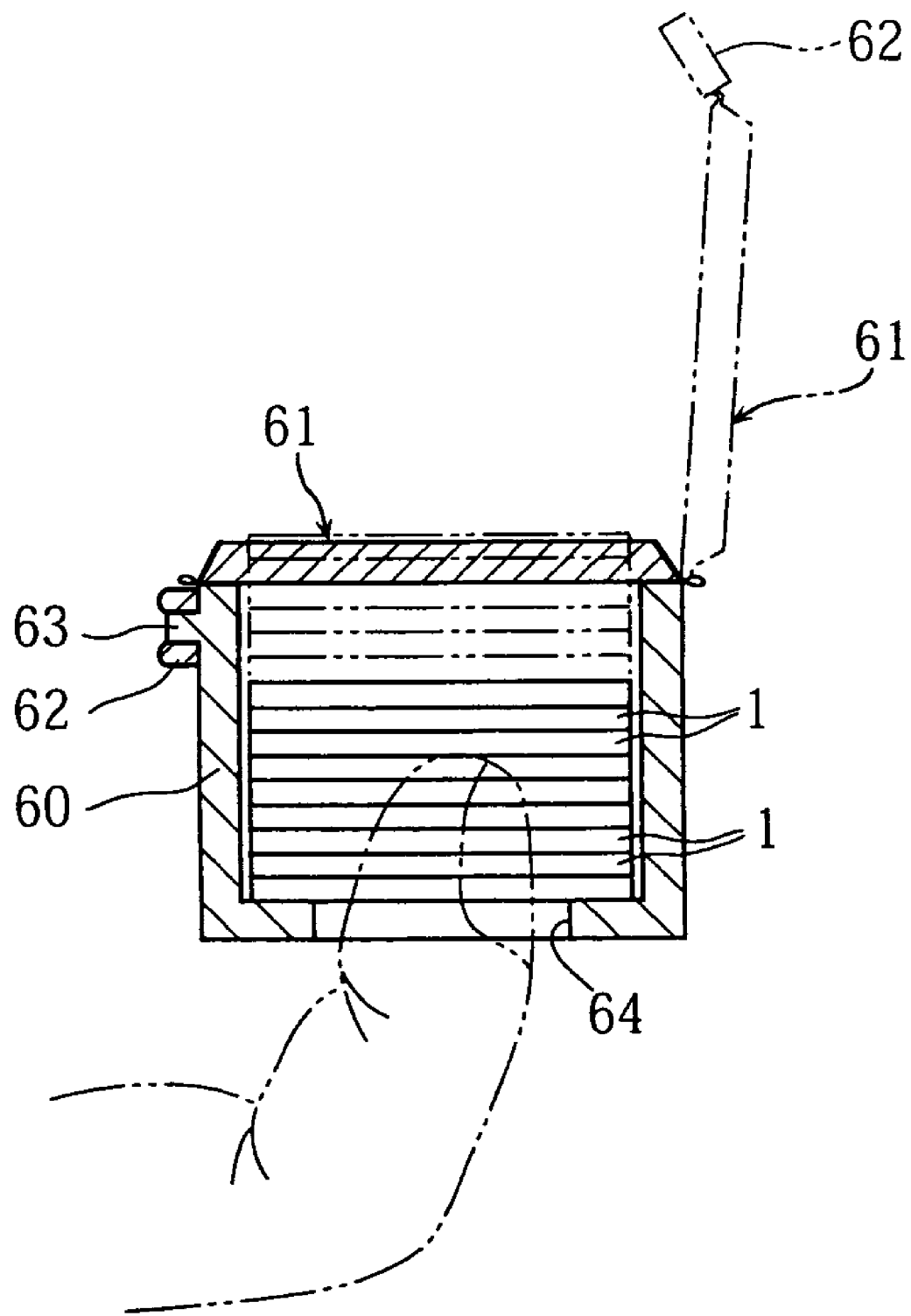
FIG. 7 is a sectional view of a sensor cartridge.

As shown in FIGS. 6 and 7, a plurality of sensor packs 1 for additional loading are preferably stored as accommodated in a container 6. The illustrated container 6 includes a container body 60 for accommodating a plurality of sensor packs 1, and a lid 61 attached to the container body 60 and provided with a hook 62. The container body 60 is provided with a projection 63 and an opening 64. The projection 63 serves to engage the hook 62. By this engagement, the state in which the lid 61 is closed is maintained properly. As better shown in FIG. 7, the sensor packs 1 accommodated in the container body 60 can be pushed up by inserting e.g. a finger into the opening 64. Thus, a required number of sensor packs 1 can be taken out easily.

Figure 8:
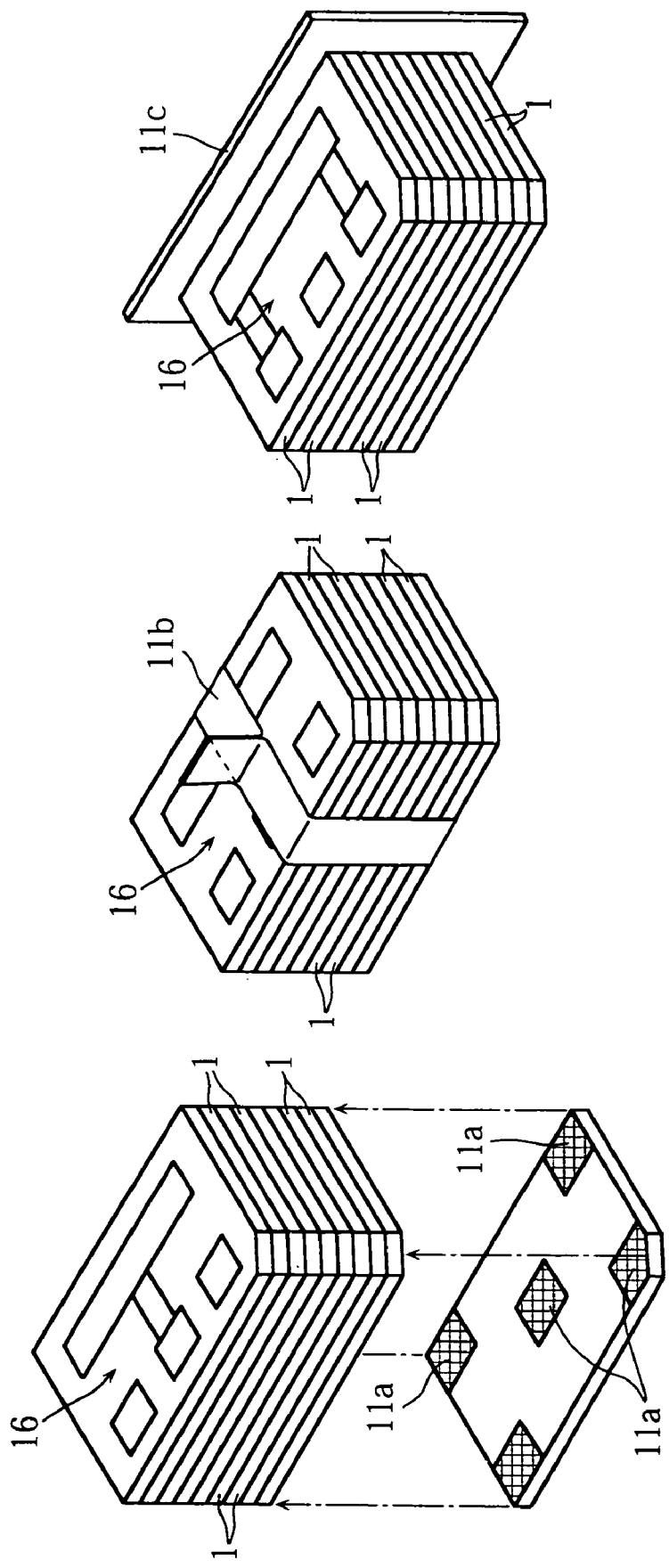
FIG. 8A-8C each is a perspective view for showing a manner of bundling of a plurality of sensor packs.

Preferably, in the container body 60, a plurality of sensor packs 1 are stored as stacked and bundled together. Specifically, the bundle of sensor packs 1 is made by using an adhesive element 11a such as a double-sided adhesive tape or an adhesive as shown in FIG. 8A, by using a strip lib as shown in FIG. 8B or by using a film 11c having an adhesive surface as shown in FIG. 8C. The methods shown in FIGS. 8A-8C are merely examples, and the sensor packs 1 may be bundled by methods other than those shown in the figures.

Figure 9:
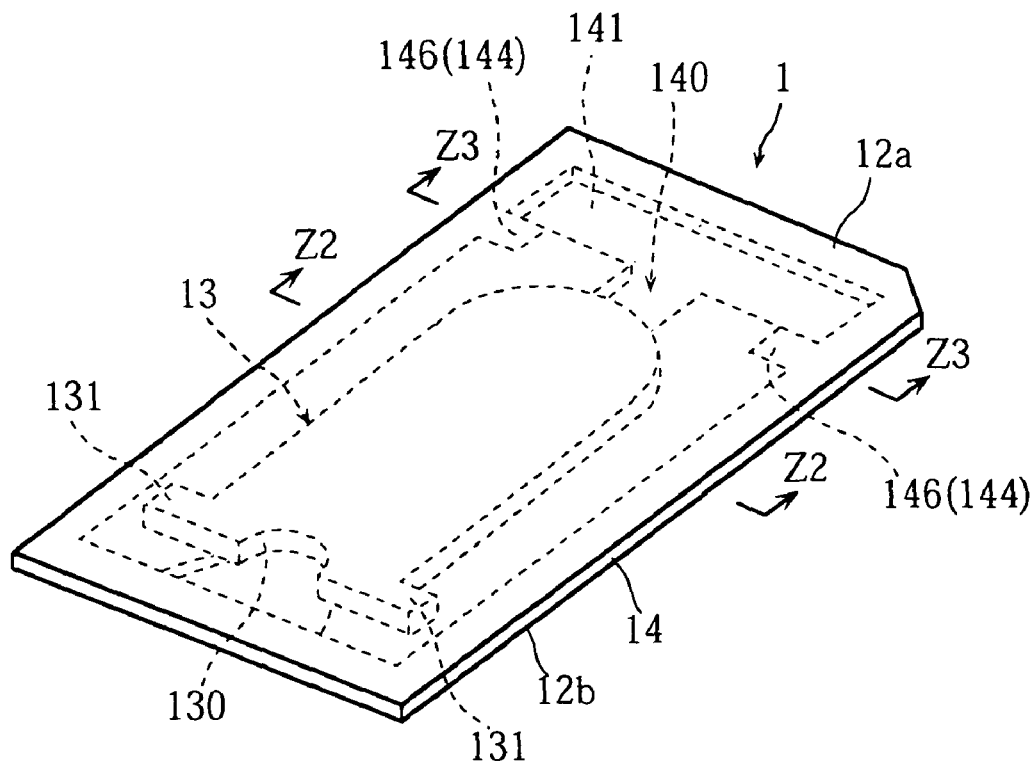
FIG. 9 is an entire perspective view of a sensor pack.

As shown in FIGS. 9 and 10, the sensor pack 1 includes a pair of sealing sheets 12a, 12b, and a biosensor 13 and a base film 14 which are enclosed between the sealing sheets. In using the sensor pack 1, a slit 15 is formed at the front end as shown in FIG. 11, and the biosensor 13 is caused to project from the slit 15, as shown in FIG. 12B.

Figure 13:
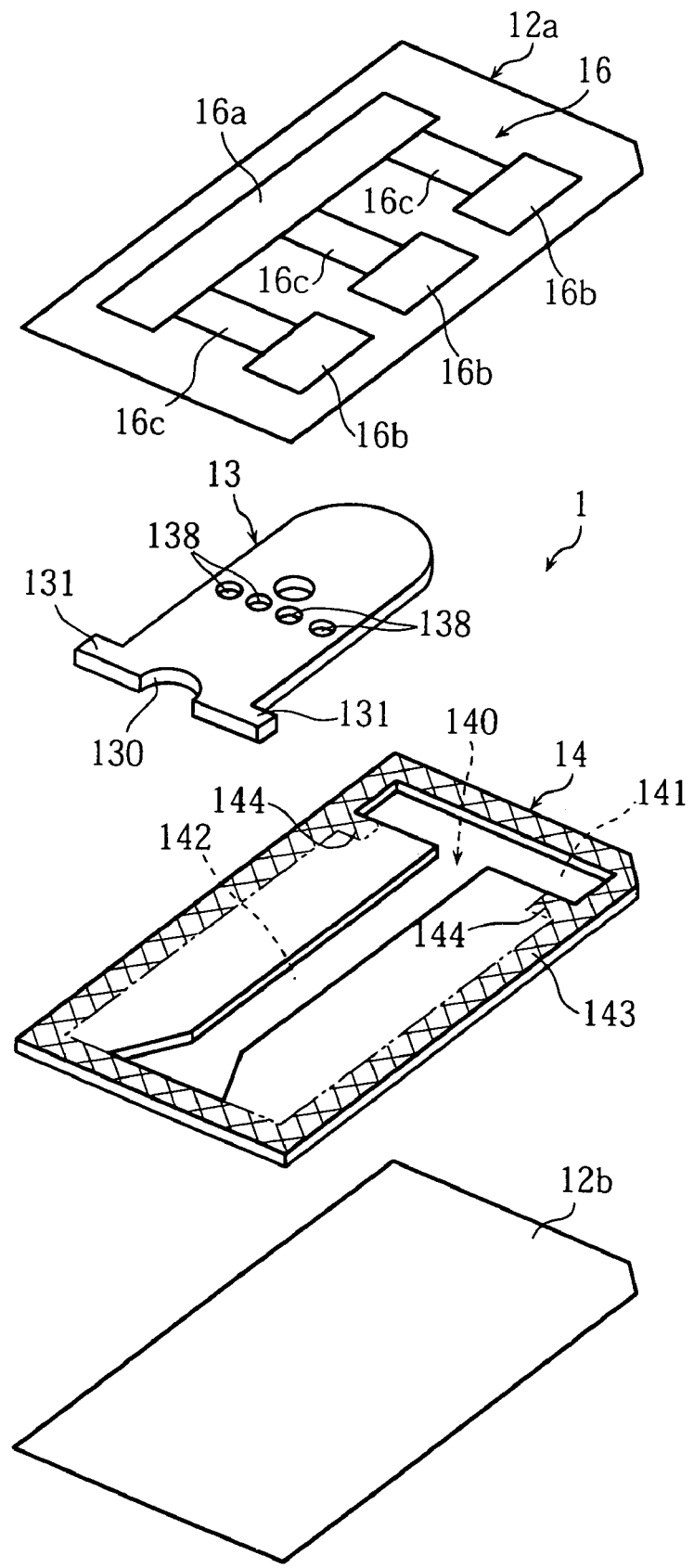
FIG. 13 is an exploded perspective view of a sensor pack.

For example, each of the sealing sheets 12a, 12b may be a laminate formed by disposing an aluminum foil between resin sheets. As shown in FIG. 13, the sealing sheet 12a has an obverse surface provided with an information providing portion 16 for outputting information relating to the biosensor 13. Examples of the information relating to the biosensor 13 may include data (correction information) which enables computation based on the sensitivity of the biosensor 13, or individual information on the biosensor 13 (the date of production, the expiry date, the manufacturer, the place of production (e.g. country or factory), and the identification information of the lot (lot number) in which the biosensor 13 is included. In this embodiment, the formation pattern of the information providing portion 16 is selected depending on the content of the information to be outputted. For example, as shown in FIGS. 14A-14H, the information providing portion 16 includes a common electrode 16a in the form of a strip and three individual electrodes 16b. With respect to each of the individual electrodes 16b, whether or not the individual electrode 16b is connected to the common electrode 16a via a conductor 16c is selected, whereby an appropriate pattern (information) can be selected from eight patterns. The number of the individual electrodes and the number of patterns are not limited to those illustrated in the figures. The information providing portion 16 can be provided with an intended pattern by screen printing or vapor deposition, for example. The recognition manner of the information provided by the information providing portion 16 will be described later.

Figure 15A:
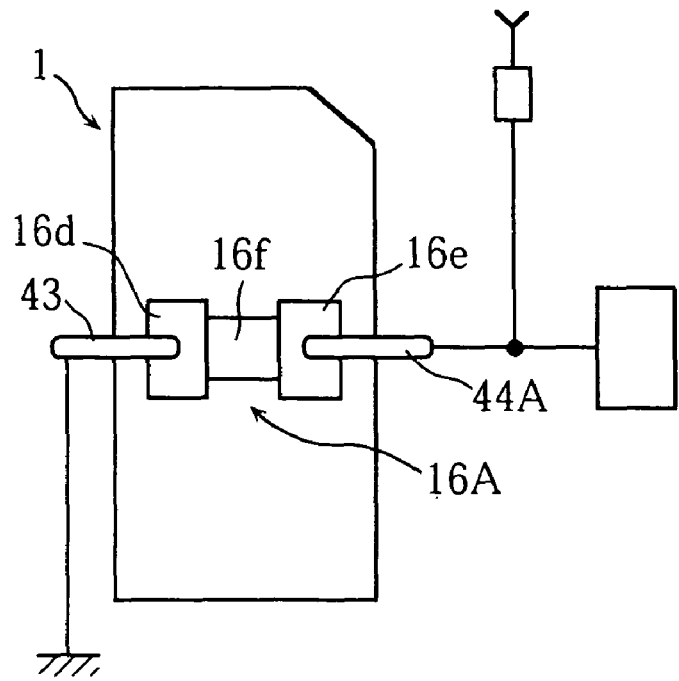
FIGS. 15A and 15B each is a schematic view for describing another example of information providing portion.
Figure 15B:
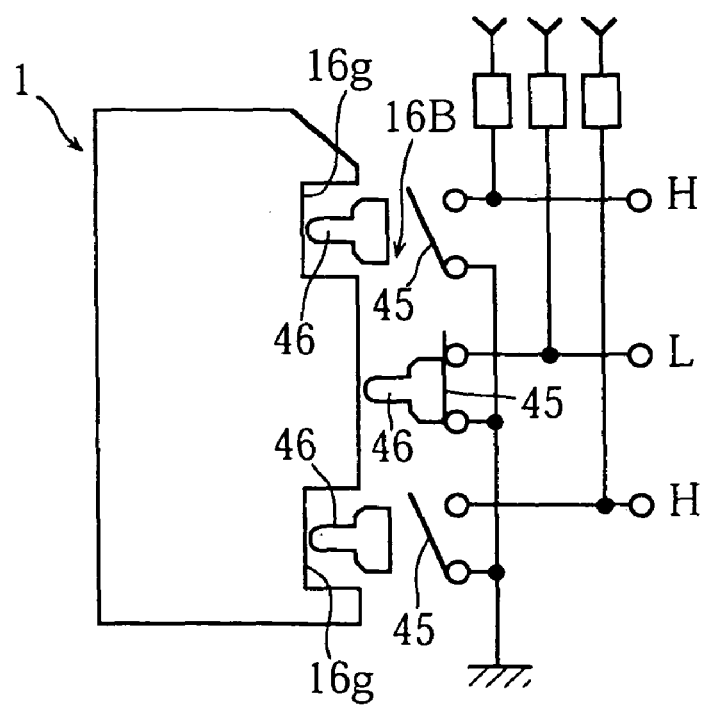

The information providing portion may have another structure as shown in FIGS. 15A and 15B. The information providing portion 16A shown in FIG. 15A includes a pair of pads 16d, 16e connected to each other via a resistor 16f. In the information providing portion 16A, the resistance of the resistor 16f is set depending on the content of the information to be outputted. The resistance of the resistor 16f is adjusted by selecting the thickness, width, length or material of the resistor 16f. The information providing portion 16B shown in FIG. 15B can output information of an intended content by selecting whether or not a cutout 16g is formed at a predetermined portion. Obviously, the information providing portion may have a structure different from those shown in FIGS. 13, 15A and 15B.

As shown in FIGS. 11 through 13, the base film 14 has a T-shaped through-hole 140. The through-hole 140 comprises an unsealing groove 141 and a guide groove 142 connected to each other. As better shown in FIG. 11, the unsealing groove 141 is utilized for forming the slit 15 in the front end of the sensor pack 1. The slit 15 is formed by breaking the sensor pack 1 with a blade 41, and the unsealing groove 141 is provided to help the penetrating movement of the blade 41. The guide groove 142 is utilized for causing the biosensor 13 to project from the sensor pack 1. Specifically, the biosensor 13 is caused to project from the sensor pack 1 by moving the biosensor 13 by using a blade 553, and the guide groove 142 guides the movement of the blade 553. The configuration of the through-hole 140 is not limited to the illustrated one. For example, part of the through-hole may be open to a side of the base film.

The base film 14 having the above configuration is bonded to one of the sealing sheets 12a at the periphery thereof and more specifically at a bonding region 143 which is cross-hatched in FIG. 13. Though not illustrated in the figure, the base film 14 is bonded also to the other one of the sealing sheets 12b in a similar manner.

Figure 10A:
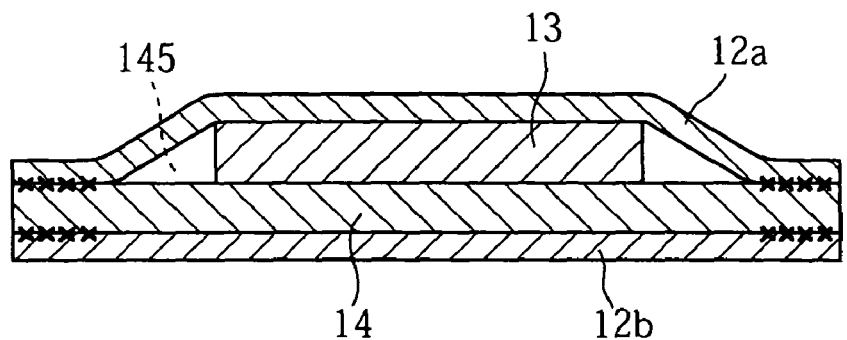
Figure 10B:
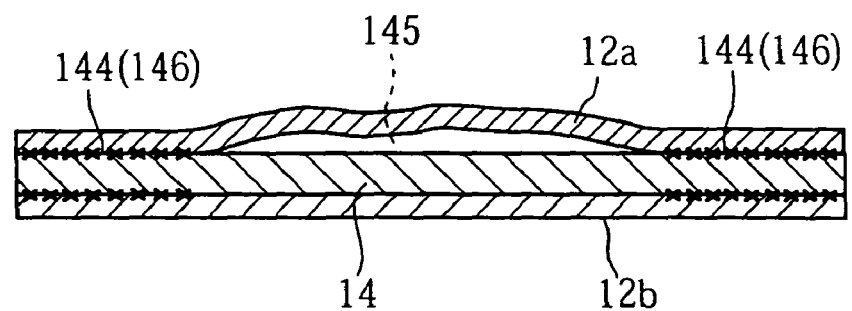
FIG. 10B is a sectional view taken along lines Z3-Z3 in FIG. 9.
Figure 11A:
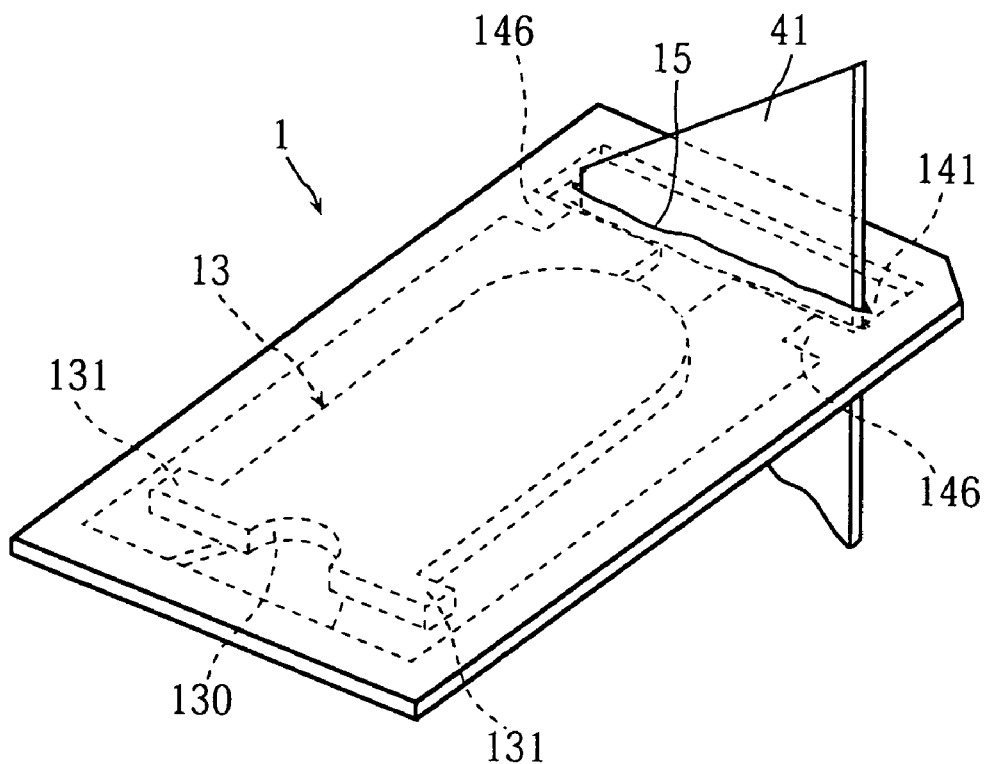
FIGS. 11A and 11B are perspective views for describing the operation for forming a cut in the sensor pack.
Figure 11B:
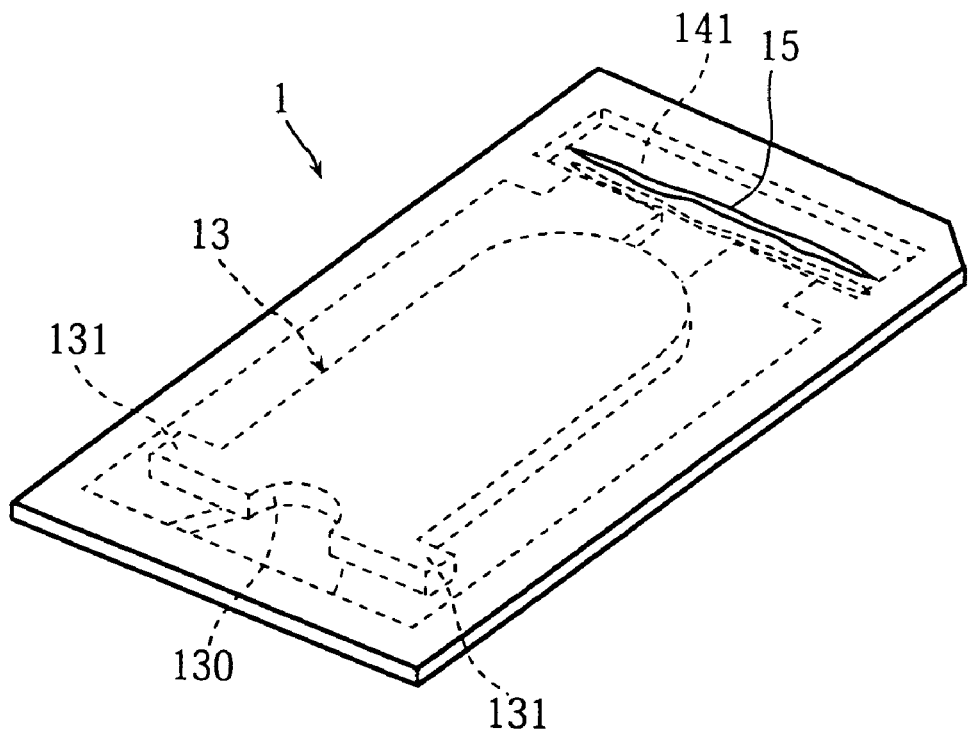

The bonding region 143 includes a pair of extensions 144. With the provision of the extensions 144, a space 145 accommodating the biosensor 13 is defined between the sealing sheet 12a and the base film 14. As shown in FIGS. 9, 10A and 10B, the width of the space 145 is narrow at a portion corresponding to the extensions 144. The narrow portion serves as a stopper portion 146 for stopping the movement of the biosensor 13, as will be described later.

The provision of the stopper portion 146 eliminates the need for providing a stopper mechanism for stopping the movement of the biosensor 13 in the analyzer X, whereby the analyzer X is advantageous in terms of the manufacturing cost. Further, the handling of the biosensor 13 for measurement or disposal, for example, can be performed while keeping the biosensor 13 integral with the pack. Moreover, the biosensor 13 after use can be easily accommodated again just by pushing the biosensor 13 into the sensor pack 1.

Since the space 145 accommodates the biosensor 13, it is preferable to keep the humidity in the space 145 low. The base film 14 can be made of a resin material such as polyethylene, polyethylene terephthalate or polyamide. Therefore, desiccant powder such as silica or molecular sieve may be contained in the base film 14 to provide dehumidifying function. In this case, the content of the desiccant powder is preferably 1 to 60% by weight, and more preferably 20 to 40% by weight relative to the total weight of the base film 14. The desiccant powder may be contained or applied to the sealing sheet 12a, or the biosensor 13 itself may have dehumidifying function.

The containing or the like of the desiccant powder eliminates the need for loading a desiccant in the space 145 and provides an advantage in terms of the manufacturing cost. Since dropping of the desiccant from the space 145 does not occur in opening the sensor pack 1, troubles due to the dropped desiccant can be avoided.

Figure 16:
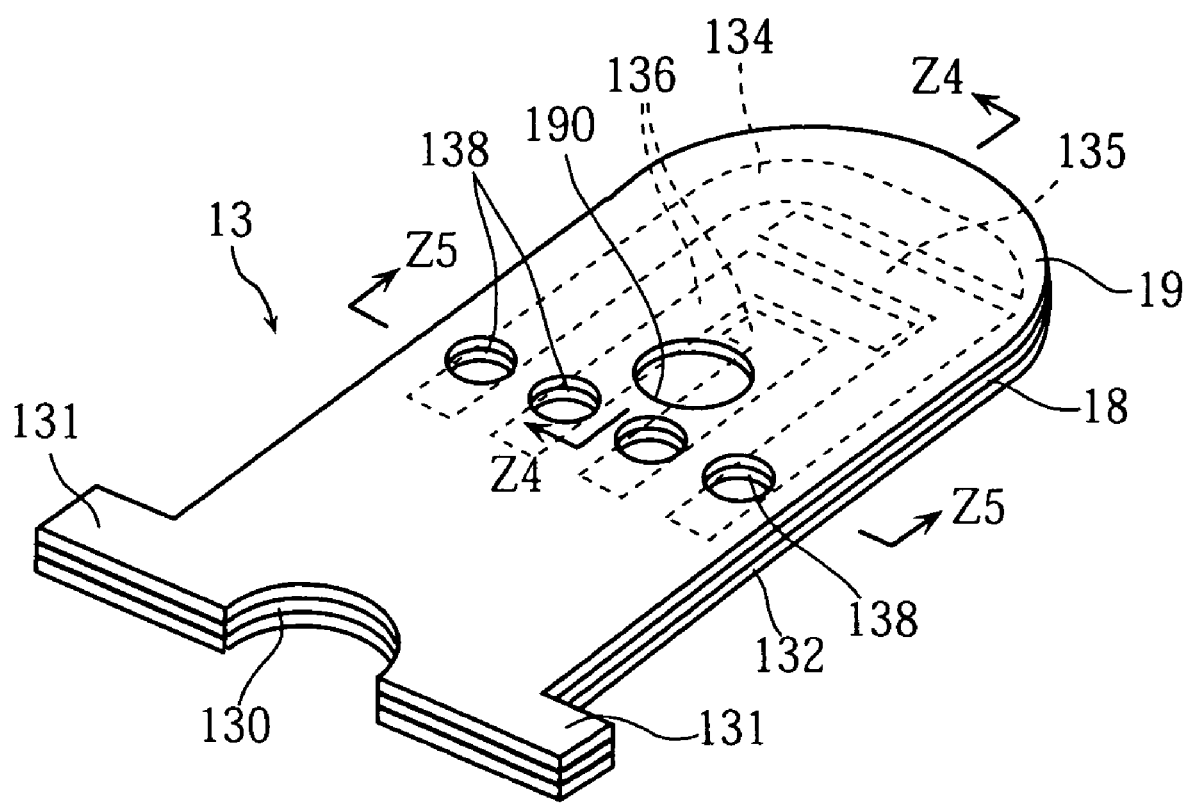
FIG. 16 is an entire perspective view of a biosensor.
Figure 17:
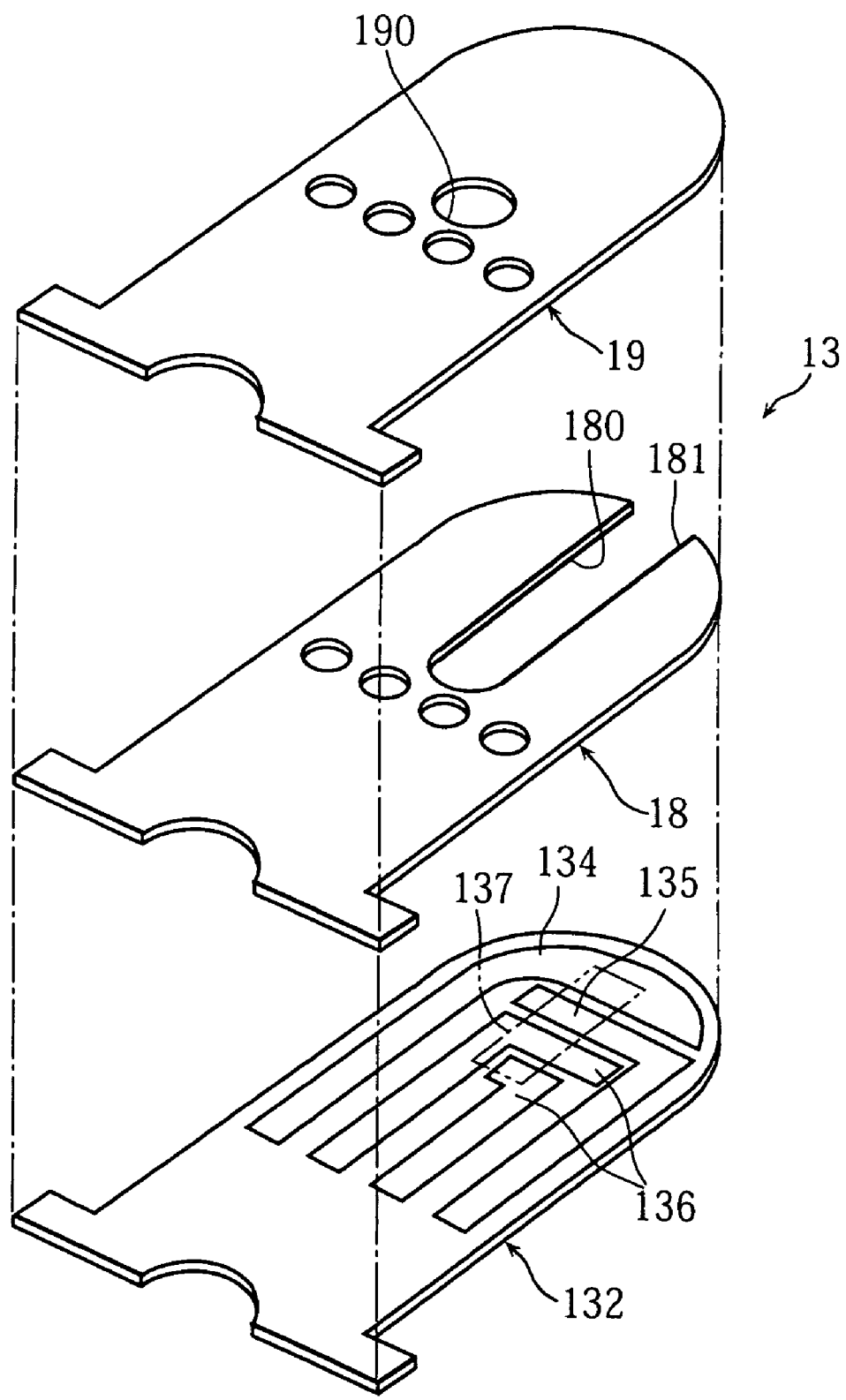
FIG. 17 is an exploded perspective view of a biosensor.
Figure 18A:
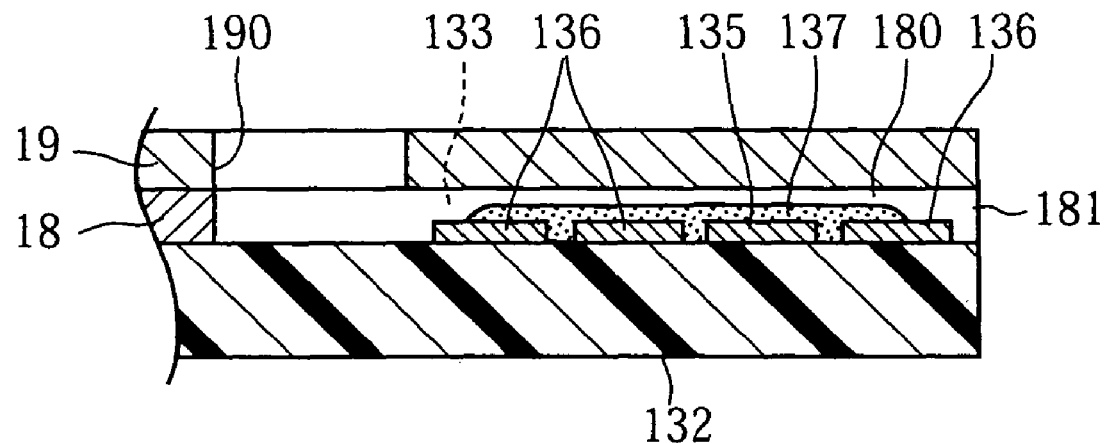

As shown in FIGS. 13, 16 and 17, the biosensor 13 has a rounded front end, and a rear end provided with a cutout 130 and a stopper portion 131. As better shown in FIGS. 12A and 12B, the cutout 130 serves to allow the penetration of the blade 553 through the sensor pack 1 and the pushing of the biosensor 13 by the blade 553. The stopper portion 131 of the biosensor 13 engages the stopper portion 146 of the sensor pack 1 when the biosensor 1 has moved to stop the movement of the biosensor 13. As shown in FIGS. 16 and 17, the biosensor 13 comprises a substrate 132, and a spacer 18 and a cover 19 which are stacked on the substrate. As shown in FIG. 18A, a flow path 133 is defined on the substrate 132.

As shown in FIGS. 17 and 18A, the spacer 18 is formed with a narrow slit 180 having an open end, and the slit 180 defines the flow path 133. The cover 19 is formed with a hole 190 communicating with the slit 180 so that gas in the flow path 133 can be discharged to the outside through the hole 190. Therefore, when a sample liquid is supplied through the front open end (sample introduction port) 181 of the slit 180, the sample liquid travels through the flow path 133 toward the hole 190 by capillary action.

Figure 18B:
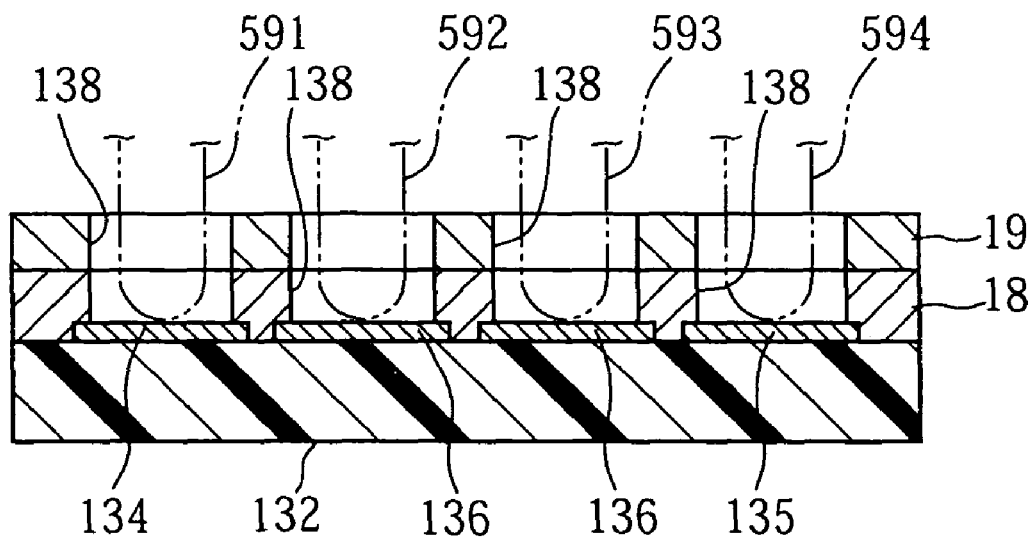
FIG. 18B is a sectional view taken along lines Z5-Z5 in FIG. 16.

As shown in FIGS. 16 and 17, on the substrate 132 are provided an operative electrode 134, a counterpart electrode 135, a pair of detection electrodes 136, and a reagent layer 137 continuously bridging the electrodes 134-136. As shown in FIG. 18B, each of the electrodes 134-136 is partially exposed via through-holes 138 penetrating through both of the spacer 18 and the cover 19. With this arrangement, probes 591-594, which will be described later, can be brought into contact with the electrodes 134-136 through the through-holes 138, whereby the application of a voltage to the reagent layer 137 and the measurement of the responsive current when the voltage is applied can be performed.

The reagent layer 137, which may be solid, is prepared by dispersing a relatively small amount of oxidoreductase in a relatively large amount of mediator (electron carrier), for example.

As the electron carrier, use may be made of iron complex or Ru complex, for example. In this case, examples of usable iron complex include potassium ferricyanide, whereas examples of usable Ru complex include one having $NH_3$ as a ligand.

The selection of the oxidoreductase depends on the kind of the particular component as the measurement target substance. Examples of particular component include glucose, cholesterol and lactic acid. Examples of oxidoreductase for such particular components include glucose dehydrogenase, glucose oxidase, hexokinase, cholesterol dehydrogenase, cholesterol oxidase, lactic acid dehydrogenase and lactic acid oxidase.

For example, the above-described sensor pack 1 can be manufactured by the method which will be described below with reference to FIGS. 19-23. Herein, it is assumed that the biosensor 13 to be accommodated in the sensor pack 1 is manufactured in advance, and the description of the manufacturing method is omitted.

Figure 19:
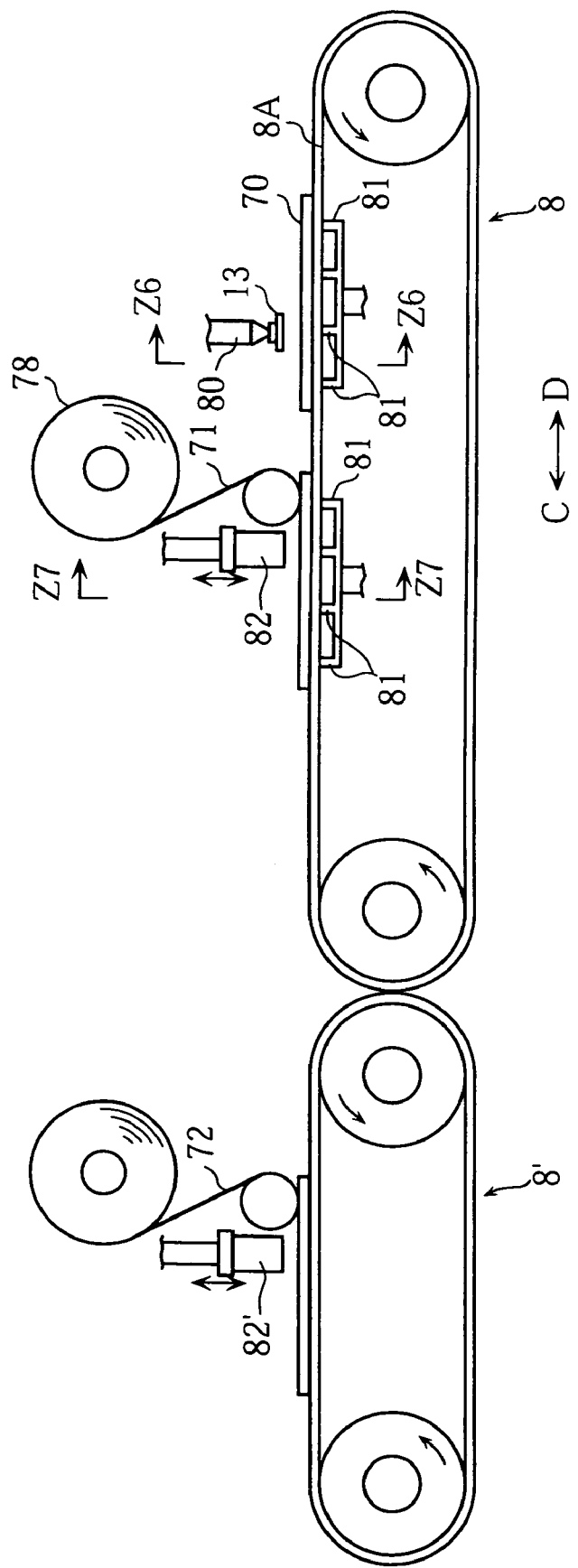
FIG. 19 is a schematic view showing a manufacturing apparatus to describe a method of manufacturing a sensor pack.

As shown in FIG. 19, the sensor pack 1 is formed by placing the biosensor 13 at an appropriate position on a punch film 70, bonding sealing films 71 and 72, and then cutting the bonded member.

Figure 20A:
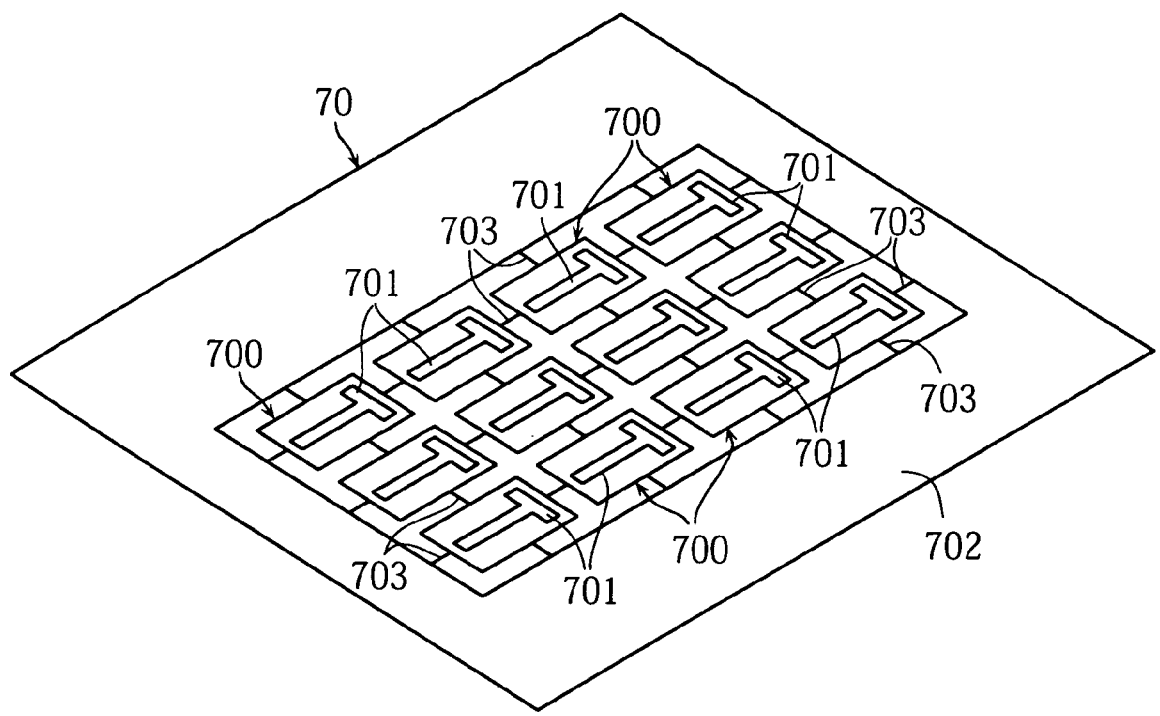
FIGS. 20A and 20B each is a perspective view showing a principal portion to describe a method of manufacturing a sensor pack.
Figure 20B:
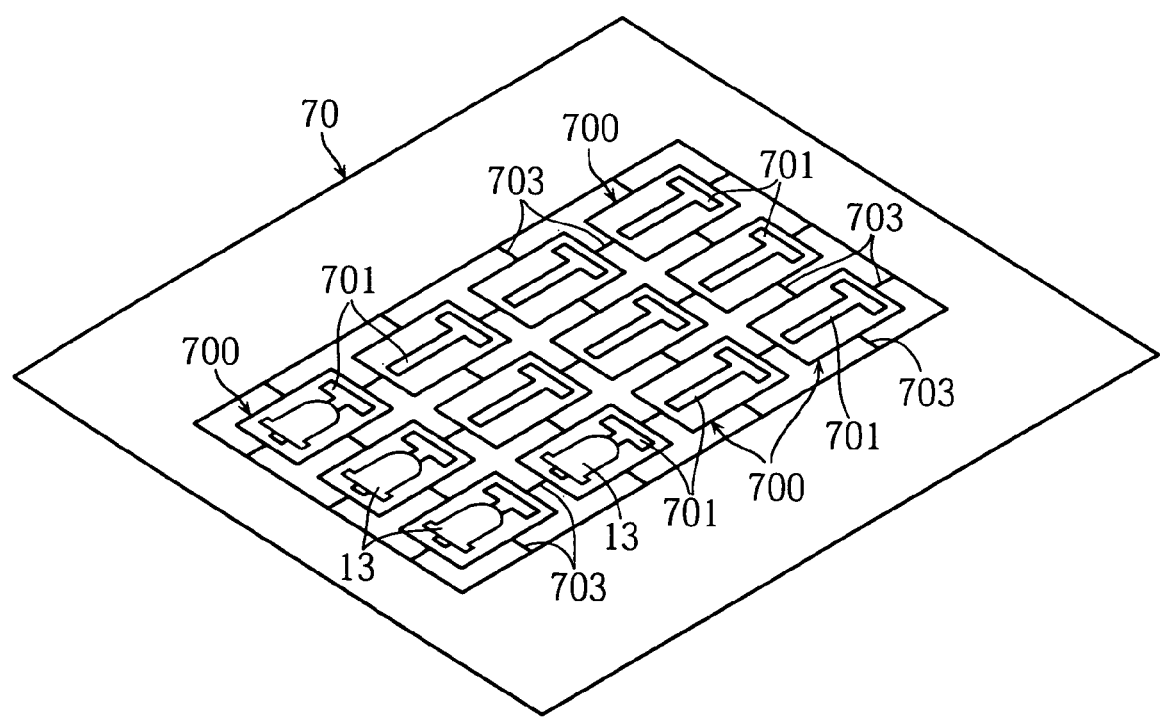

Specifically, as shown in FIG. 20A, a plurality of base film forming regions 700 are defined on the punch film 70. Each of the base film forming regions 700 is formed with a generally T-shaped through hole 701. Each of the base film forming regions 700 is supported relative to a flame portion 702 and/or an adjacent base film forming region 700 via a support bar 703. As shown in FIG. 19, the punch film 70 is transferred by a belt conveyor 8. The belt 8A of the belt conveyor 8 is made porous or in the form of a mesh to have excellent breathability.

As shown in FIGS. 19 and 21, the placing of the biosensor 13 on the punch film 70 is performed automatically by using a vacuum collet 80, for example. As will be understood from e.g. FIGS. 20B and 21, the placing operation is performed individually with respect to each of the base film forming region 700. Alternatively, a plurality of biosensors 13 may be placed simultaneously. The biosensors 13 thus placed are kept at respective positions by a plurality of suction nozzles 81 provided below the punch film 70. Specifically, since the through-hole 701 is formed in each of the base film forming regions 700 and the belt 8A has excellent breathability, when each of the suction nozzles 81 is placed directly below the biosensor 13 to suck the biosensor, the biosensor 13 is pulled toward the suction nozzle 81 while being kept in close contact with the base film forming region 700.

The suction nozzles 81 are movable together with the punch film 70 in the direction indicated by arrows CD in FIG. 19. Therefore, each of the biosensors 13 is transferred together with the punch film 70 while being positioned at the base film forming region 700. The positioned state is maintained until the subsequent step for bonding the sealing film 71 is completed.

Figure 22A:
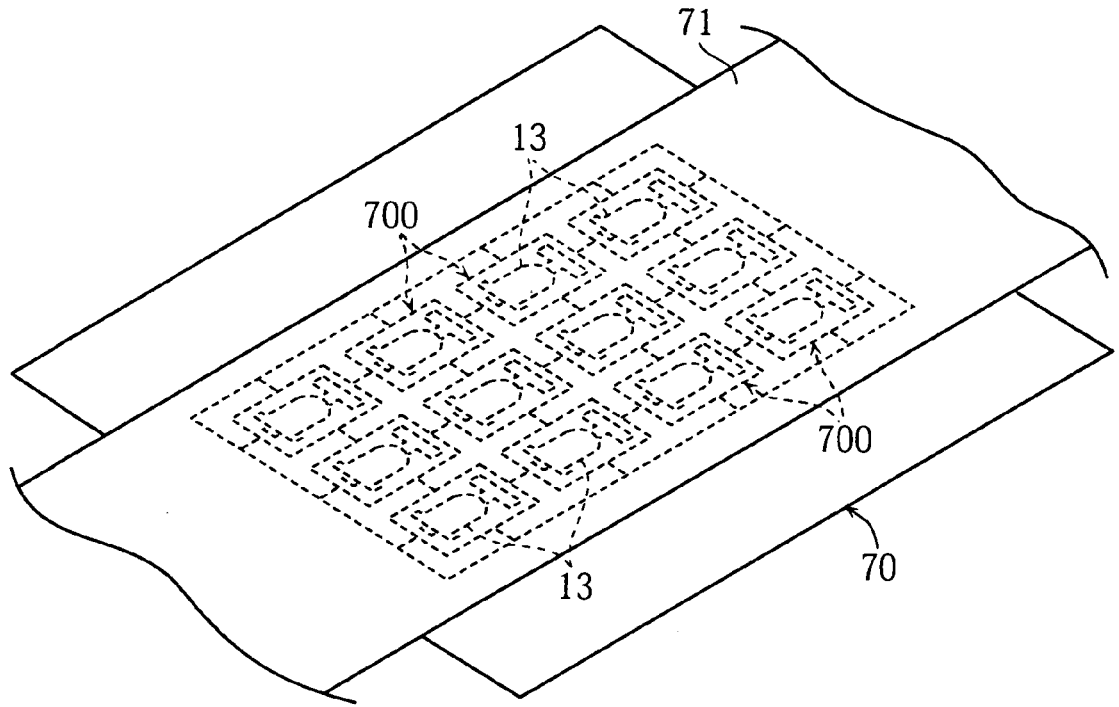
FIGS. 22A and 22B each is a perspective view showing a principal portion to describe a method of manufacturing a sensor pack.
Figure 22B:
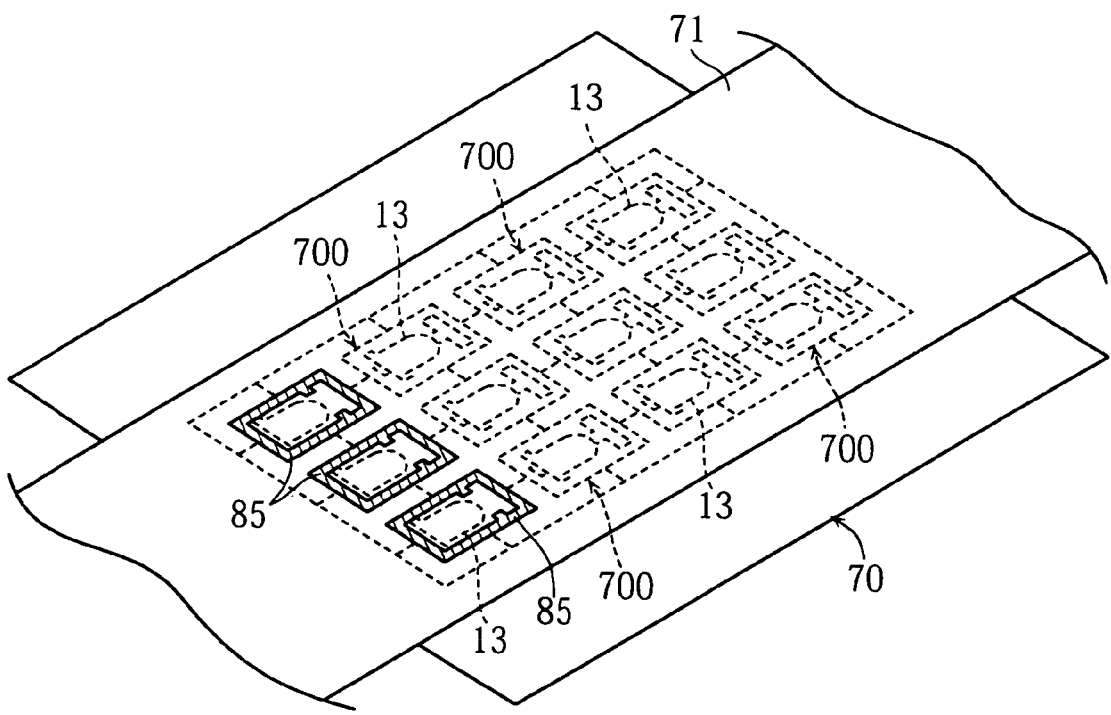
Figure 23:
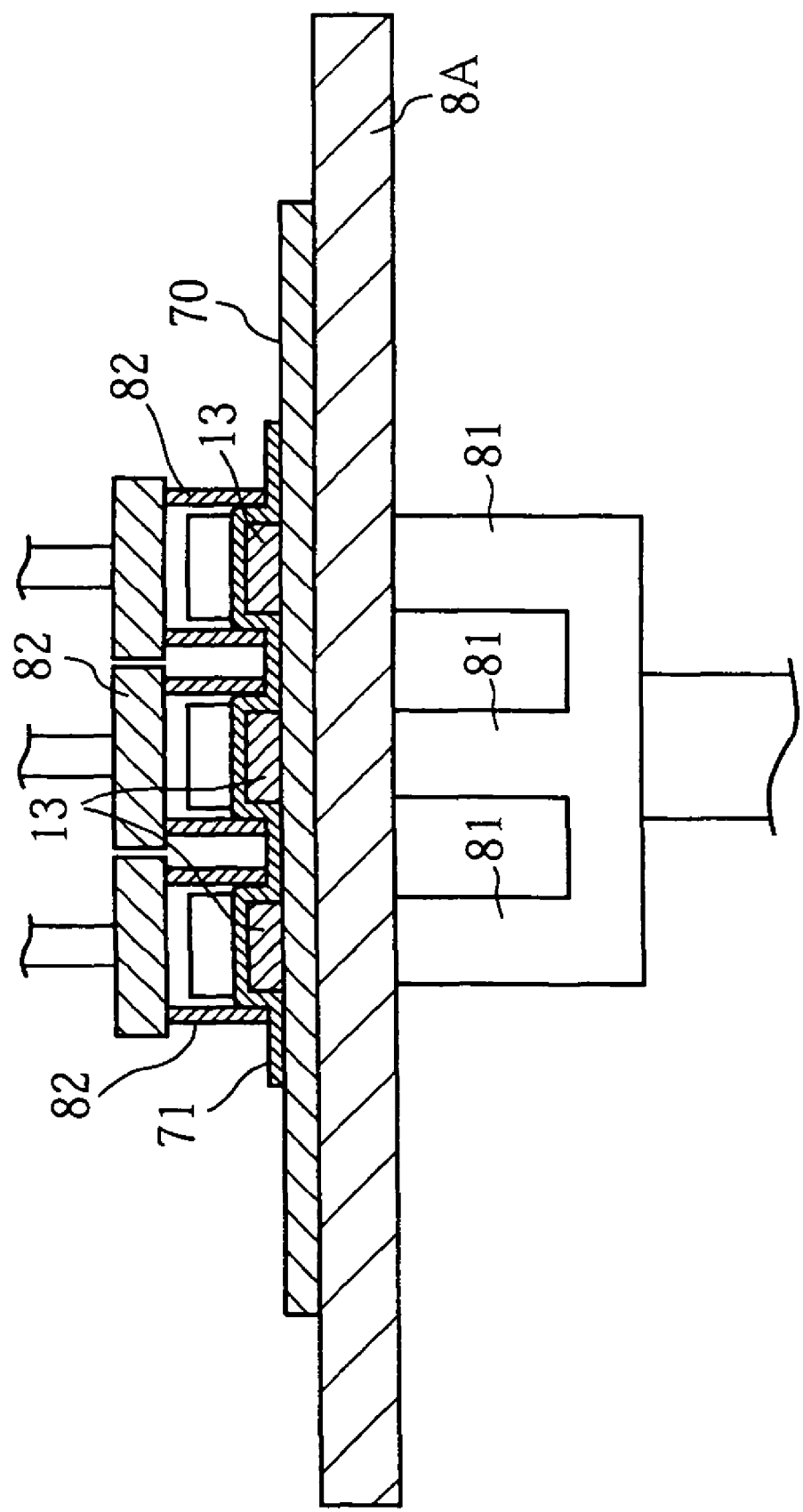
FIG. 23 is a sectional view taken along lines Z7-Z7 in FIG. 19.

The bonding of the sealing film 71 is performed by laying the sealing film 71 on the punch film 70 as an overlying layer as shown in FIG. 22A, and then applying thermal energy by using a plurality of (three in the figure) fusing stamps 82 as shown in FIGS. 19 and 23. The sealing film 71 is supplied from the roll 78. The sealing film 71 is formed, in advance, with information providing portions (indicated by reference sign 16 in FIG. 13) at portions corresponding to the base film forming portions 700. The information providing portions may be formed after the sealing film 71 is bonded.

The fusing stamps 82, which are spaced in the widthwise direction of the belt conveyor 8, fuse the sealing film 71 to a plurality of base forming regions 700 simultaneously. Each of the fusing stamps 82 has an end surface having a configuration corresponding to the hatched portion 85 in FIG. 22B so that thermal energy can be applied selectively to the peripheral portion of each of the base film forming regions 700. Each of the fusing stamps 82 is individually movable up and down by the driving force of a non-illustrated pump, for example. Therefore, even when the regions (fusion portions) to which the fusing stamps 82 are to apply thermal energy differ from each other in height, such a problem can be properly addressed, and proper bonding can be achieved. Specifically, as a result of the individual driving of the fusing stamps 82, each of the fusing stamps 82 can be located at its own height position. Therefore, even when the fusion portions have height variation, each of the fusion stamps 82 can be located at a position corresponding to the higher fusion portion. Thus, thermal energy can be properly applied to each fusion portion, whereby thermal fusing can be properly performed.

After the thermal fusing, the biosensor 13 is retained at an appropriate position between the punch film 70 and the sealing film 71. The suction of the biosensor 13 by using the suction nozzle 81 is released.

Subsequently, after the sealing film 71 is cut, the sealing film 71 and the punch film 70 are turned over and transferred onto a belt conveyor 8' for bonding a sealing film 72 (See FIG. 19). With the sealing film 72 placed on the punch film 70 as an overlying layer, the sealing film 72 is bonded. As a result, the biosensor is hermetically sealed between the paired sealing films 71 and 72. The bonding of the sealing film 72 is performed by using fusing stamps 82' which are similar to those described above. Thereafter, cutting is performed at a portion corresponding to each of the film forming regions 700, whereby individual sensor packs 1 as shown in FIGS. 9 and 13 are obtained.

Each of the sealing films 71, 72 is not limited to one in the form of a hoop, and use may be made of one which has been cut to a size corresponding to the size of the punch film 70. The bonding of the sealing film 72 may be performed by placing the sealing film 72 on the belt conveyor 8' in advance, placing the sealing film 71 and the punch film 70 on the sealing film 72 without turning over, and then performing fusing.

The opening mechanism 4 shown in FIG. 3 serves to open the sensor pack 1 held at the wait position. The blade 41 and an operation button 40 are included in the opening mechanism 4. The operation button 40 is accommodated in a space 27 defined in the device body 2 while being biased toward the front side of the device body 2 (in the direction indicated by the arrow A in the figure) by a resilient member 42 (illustrated as a coil spring in FIG. 3). The blade 41 is integrally formed on the operation button 40 to move together with the operation button 40. Therefore, when a pushing force to push the operation button 40 toward the deeper side of the device body (in the direction indicated by the arrow B in the figure) is applied to the button, the blade 41 moves together with the operation button 40 in the arrow B direction to penetrate through the front end of the sensor pack 1, as shown in FIG. 11A. Accompanying the pushing of the operation button 40, a power source for driving the measurement mechanism 5, for example, may be turned on or the feeder 22 shown in FIG. 3 may be moved to automatically feed a sensor pack 1 toward the measurement mechanism 5. When the force exerted to the operation button 40 is released, the operation button 40 and the blade 41 return to their original positions. Thus, the slit 15 as shown in FIG. 11B is formed at the front end of the sensor pack 1, whereby the sensor pack 1 is opened. Although the blade 41 moves integrally with the operation button 40 in the illustrated example, the blade may be so arranged as to move following the movement of the operation button. In this case, the following movement may be realized by a mechanical system or an electrical system.

At the wait position, information relating to the biosensor 13 is read by utilizing the information providing portion 16 before the sensor pack 1 is opened. Specifically, as will be understood from FIGS. 14A-14H, the device body 2 is provided with a single common terminal 43 and three individual terminals 44. When the sensor pack 1 is at the wait position, the common terminal 43 comes into contact with the common electrode 16a of the sensor pack 1, whereas the tree individual terminals 44 come into contact with respective individual electrodes 16b of the sensor pack 1. The information of the information providing portion 16 is recognized based on the presence or absence of conduction between each of the individual terminals 44 and the common terminal 43 as well as the combination thereof. As will be understood from FIGS. 14A-14H, eight kinds of information distinguishable from each other can be recognized in this embodiment. When the information providing portion 16A as shown in FIG. 15A is utilized, a single measurement terminal 44A is provided in the device body 2 (See FIGS. 2 and 3). When the information providing portion 16B as shown in FIG. 15B is utilized, a plurality of switches 45 and a plurality of movable members 46 capable of individually opening and closing the switches 45 are provided in the device body. In this case, each switch 45 is kept open when the relevant movable member 46 is received in a cutout 16g of the sensor pack 1, whereas the switch 45 is closed when the movable member 46 is located at a portion which is not formed with a cutout 16g. The information of the information providing portion 16B is recognized based on the combination of ON/OF of each switch 45.

For example, when the sensor pack 1 is provided with information on the lot and the usable period, the device may automatically perform correction so as not to perform the measurement when the usable period of the sensor pack 1 is expired. With such an arrangement, when a user additionally loads sensor packs 1 into the accommodation portion (See FIGS. 2 and 3), the user need not pay attention to the lot and usable period of each sensor pack 1 to be loaded, which is convenient.

Figure 24:
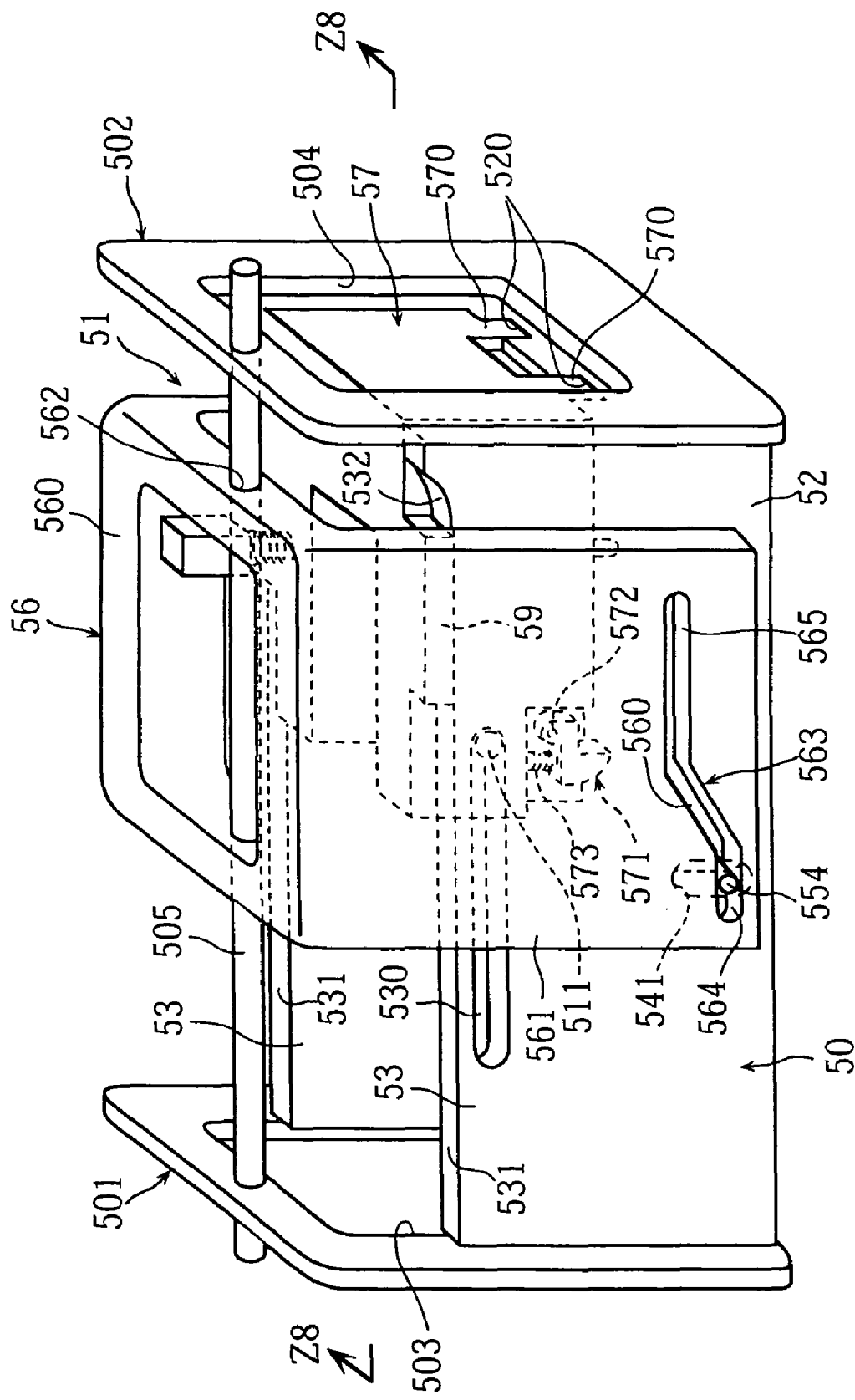
FIG. 24 is an entire perspective view of a measurement mechanism.

The measurement mechanism 5 serves to cause the biosensor 13 to project from the sensor pack 1 opened and transferred from the wait position and to measure the concentration of a particular component in the sample liquid supplied to the biosensor 13. As shown in FIG. 24, the measurement mechanism 5 includes a base 50, and a slider 51 slidably connected to the base. The slider 51 is reciprocally movable by known means such as a rack and pinion mechanism by utilizing the driving force of e.g. a motor (not shown).

Figure 25:
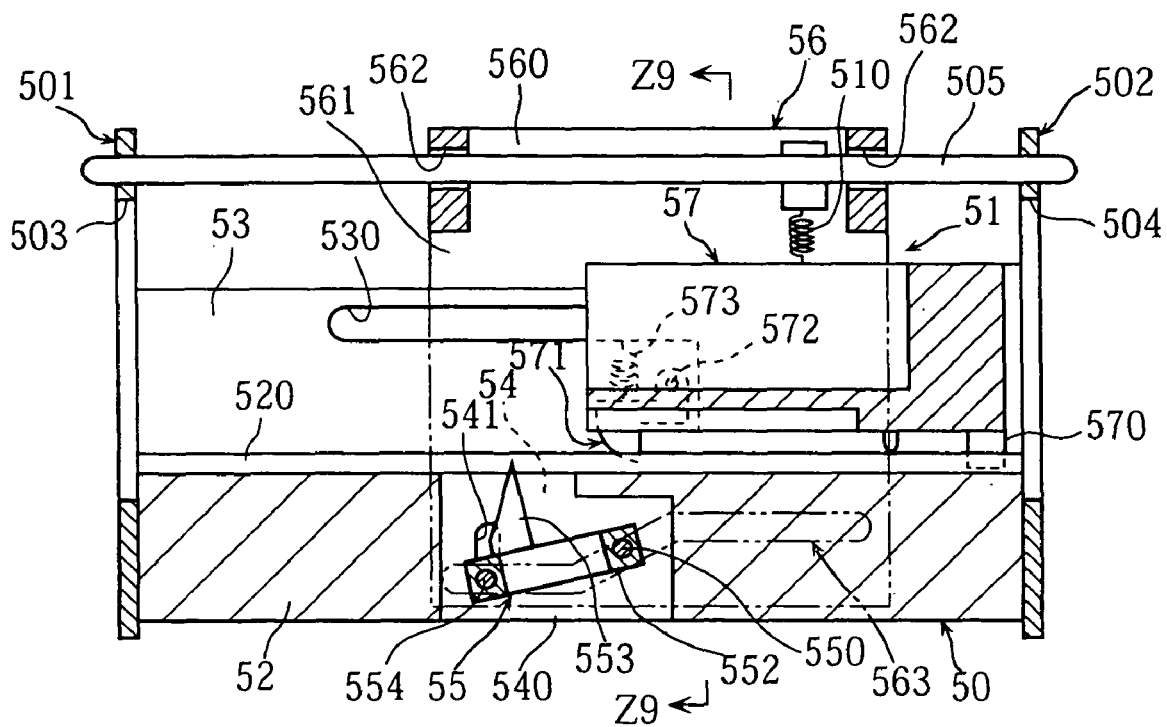
FIG. 25 is a sectional view taken along lines Z8-Z8 in FIG. 24.
Figure 26:
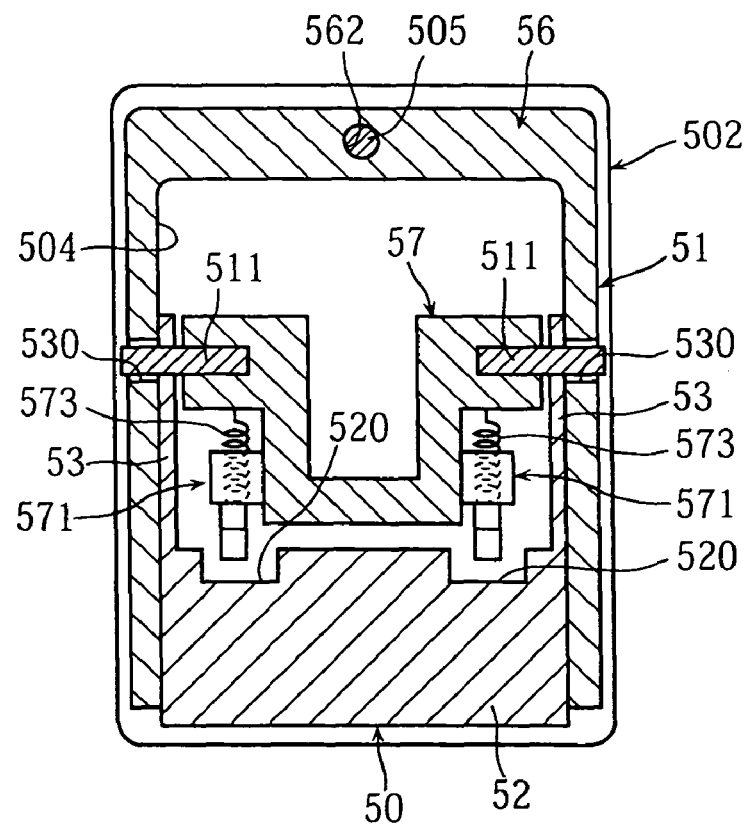
FIG. 26 is a sectional view taken along lines Z9-Z9 in FIG. 25.

As shown in FIGS. 24-26, the base 50 includes a base portion 52 and side walls 53 extending upward from opposite side edges of the base portion 52. The base 50 further includes opposite ends provided with plate frames 501, 502. The plate frame 501 is formed with an opening 503 for introducing the sensor pack 1, whereas the plate frame 502 is formed with an opening 504 for discharging the sensor pack 1. The plate frames 501, 502 support a guide rod 505.

The base portion 52 has an upper surface formed with two guide grooves 520 and is formed with a space 54 at the center portion thereof, as shown in FIG. 25. A movable cutter 55 is arranged in the space 54, and an elongated hole 541 is formed at a side wall 540 defining the space 54. The movable cutter 55 comprises a blade 553 and a holding block 552 for holding the blade. The movable cutter 55 has opposite ends one of which is pivotally connected to the base 50 via a shaft portion 550. The other end of the movable cutter 55 is connected to the elongated hole 541 via a shaft portion 554, so that the pivoting range of the movable cutter 55 is defined by the elongated hole 541. Each of the side walls 53 has an upper portion formed with an elongated hole 530, and an upper surface 531 formed with a tapered portion 532 at an end thereof.

The slider 51 includes a slide guide 56 and a slider block 57. The slider guide 56 and the slider block 57 are connected to each other via a resilient member 510 (illustrated as a coil spring in the figure) and pins 511. Therefore, the slide guide 56 and the slider block 57 can move together relative to the base 50 and move vertically relative to each other.

As shown in FIGS. 24-27, the slider block 57 is provided with a pair of front hooks 570 and a pair of rear hooks 571. As better shown in FIG. 27, the front hooks 570 and the rear hooks 571 serve to hold the sensor pack 1 and are so arranged that the distance between the front hooks 570 and the rear hooks 571 corresponds to the length of the sensor pack 1. Though not clearly shown in the figure, the distance between the paired front hooks 570 and the distance between the paired rear hooks 571 are set to be smaller than the width of the sensor pack 1 and larger than the width of the biosensor 13.

Each of the front hooks 570 is formed integrally on the slider block 57. However, the front hook may be made separately from the slider block. Each of the rear hooks 571 is connected to the rear end of the slider block 57 via a shaft 572. The rear hook 571 is pivotally supported by the slider block 57 while being biased downward by a resilient member 573. The rear end of the rear hook 571 has a curved surface.

Figure 28A:
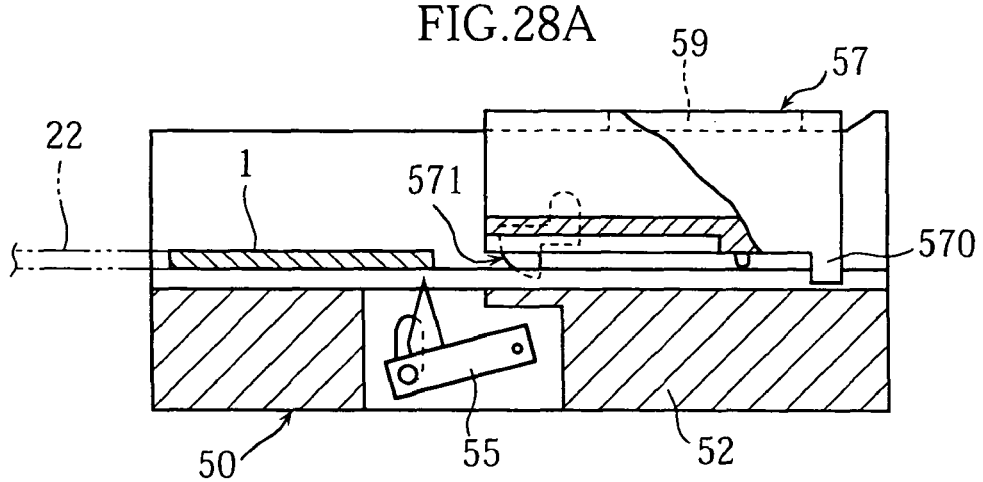
FIGS. 28A and 28B each is a sectional view of a principal portion to describe means for holding a sensor pack in the measurement mechanism.
Figure 28B:
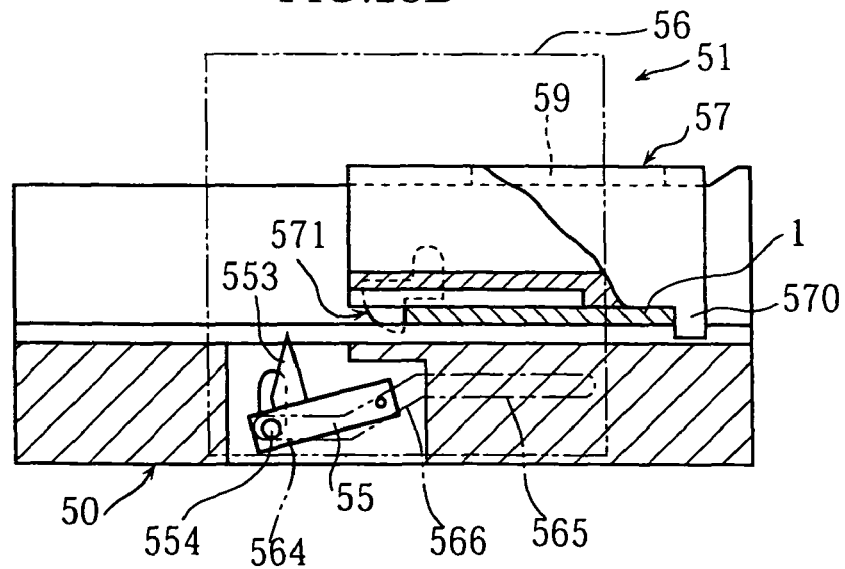

As noted above, the sensor pack 1 is transferred to the measurement mechanism 5 by the feeder 22. Specifically, as shown in FIG. 28A, the sensor pack 1 is transferred onto the base portion 52 of the base 50 through the opening 503 of the plate frame 501. When the sensor pack 1 is further pushed from this position, the sensor pack 1 moves while coming into contact with the curved surface of the rear hooks 571, whereby the rear hooks 571 are lifted. As shown in FIG. 28B, when the sensor pack 1 is moved until the front end of the senor pack 1 engages the front hooks 570, the front hooks 570 hinder further advancement of the sensor pack 1. Since the distance between the front hooks 570 and the rear hooks 571 corresponds to the length of the sensor pack 1, the rear end of the sensor pack 1 engages the rear hooks 571, whereby the sensor pack 1 is snugly held between the front hooks 570 and the rear hooks 571. In this state, the sensor pack 1 is movable together with the slider block 57, and hence, with the slider 51.

As shown in FIGS. 24-26, the slide guide 56 includes an upper frame portion 560, and side walls 561 extending downward from opposite side edges of the upper frame portion 560. The upper frame portion 560 is formed with a through-hole 562. The guide rod 505 is inserted in the through-hole 562, whereby the upper frame portion 560, and hence, the slide guide 56 is supported by the guide rod 505. With this arrangement, the slide guide 56, and hence the entirety of the slider 51 is movable along the guide rod 505.

The side wall 561 is formed with a cam groove 563. The cam groove 563 has opposite ends respectively provided with a first and a second straight movement portions 564 and 565 which differ from each other in height position. The straight movement portions 564 and 565 are connected to each other via an up/down movement portion 566. The cam groove 563 receives the shaft portion 554 of the movable cutter 55. Therefore, when the position of the shaft portion 554 in the cam groove 563 is changed by moving the slide guide 56, the movable cutter 55 pivots, whereby the height position of the blade 553 of the movable cutter 55 changes.

Figure 29A:
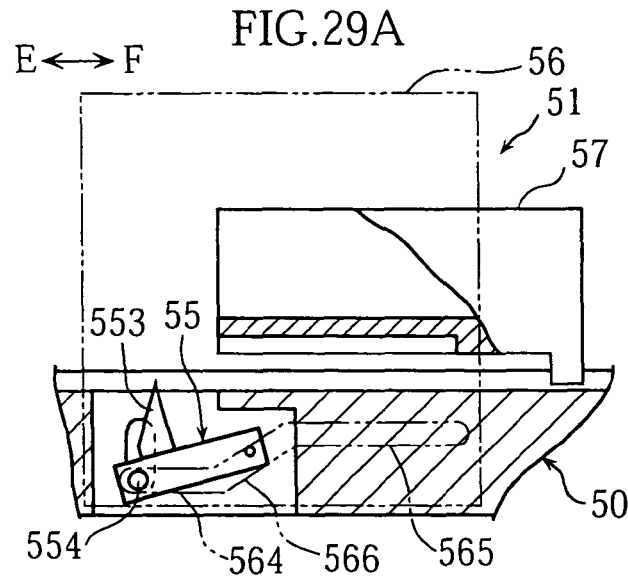
FIG. 29A-29C are sectional views showing a principal portion to describe the movement of a movable cutter.
Figure 29B:
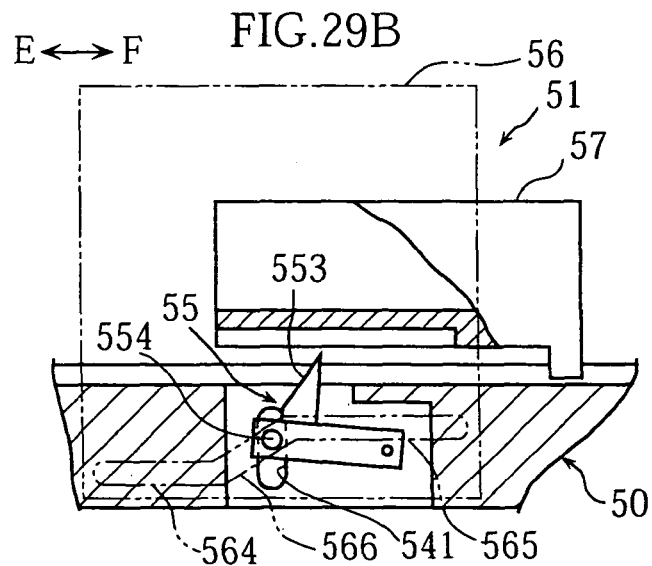
Figure 29C:
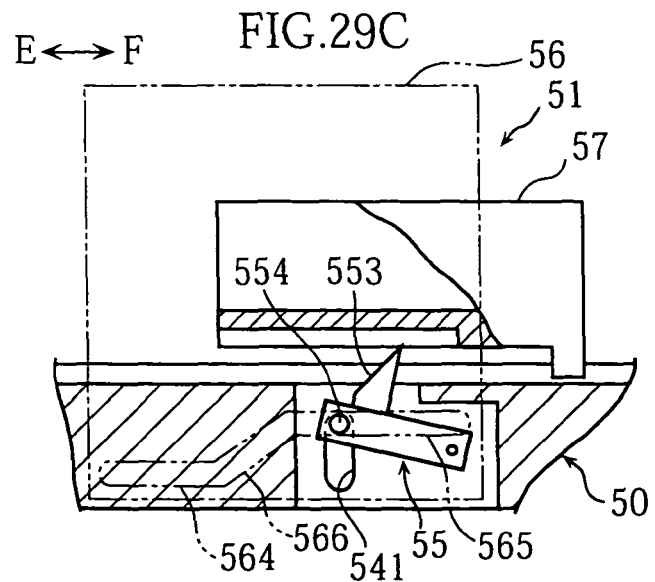

Specifically, as shown in FIGS. 28B and 29A, when the slider 51 is positioned on the right side in the figure and the shaft portion 554 is positioned in the first straight movement portion 564, the blade 553 of the movable cutter 55 is positioned at the bottom dead center. As shown in FIG. 29B, when the slide guide 56 is moved to move the shaft portion 554 from the first straight movement portion 564 toward the second straight movement portion 565 through the up/down movement portion 566, the blade 553 of the movable cutter 55 moves upward. As shown in FIG. 29C, when the shaft portion 554 reaches the second straight movement portion 565, the blade 553 is positioned at the top dead center.

Figure 12A:
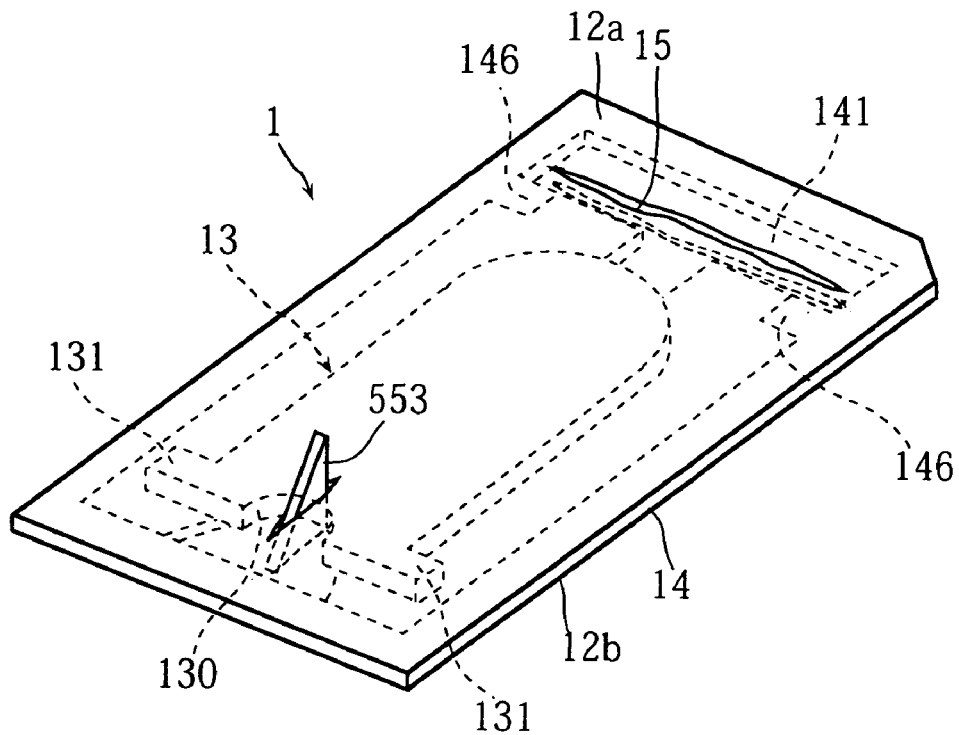
FIGS. 12A and 12B are perspective views for describing the operation for projecting a biosensor from the sensor pack.
Figure 12B:
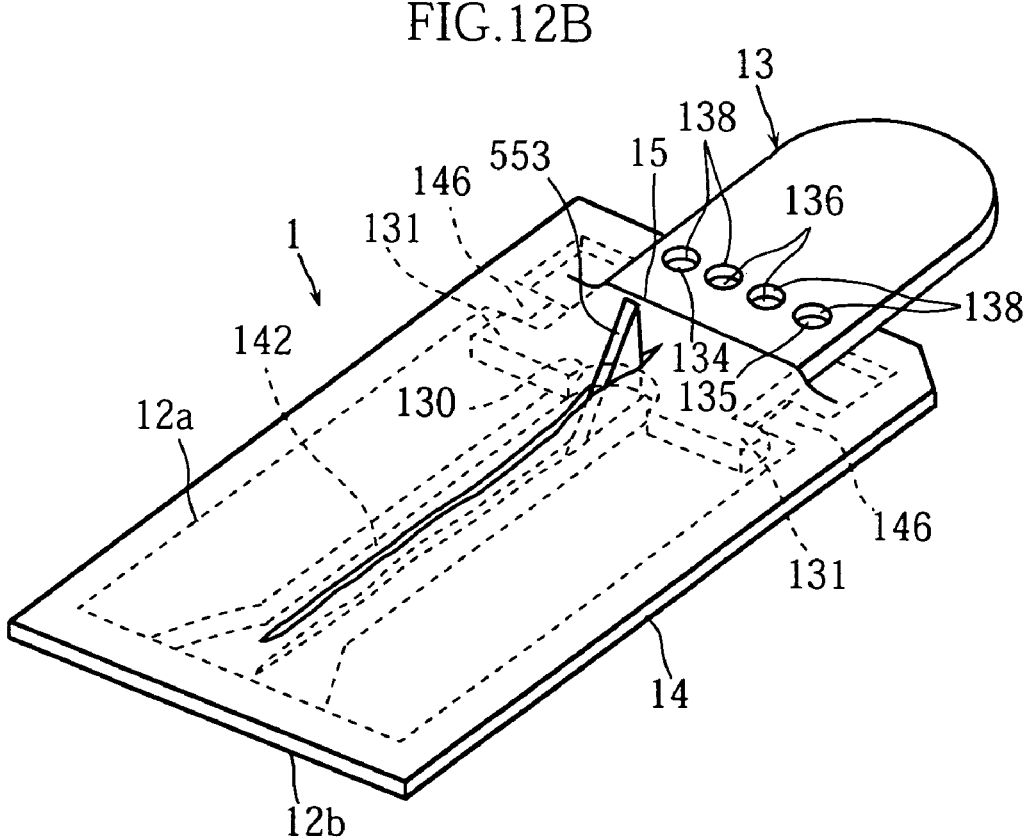
Figure 30A:
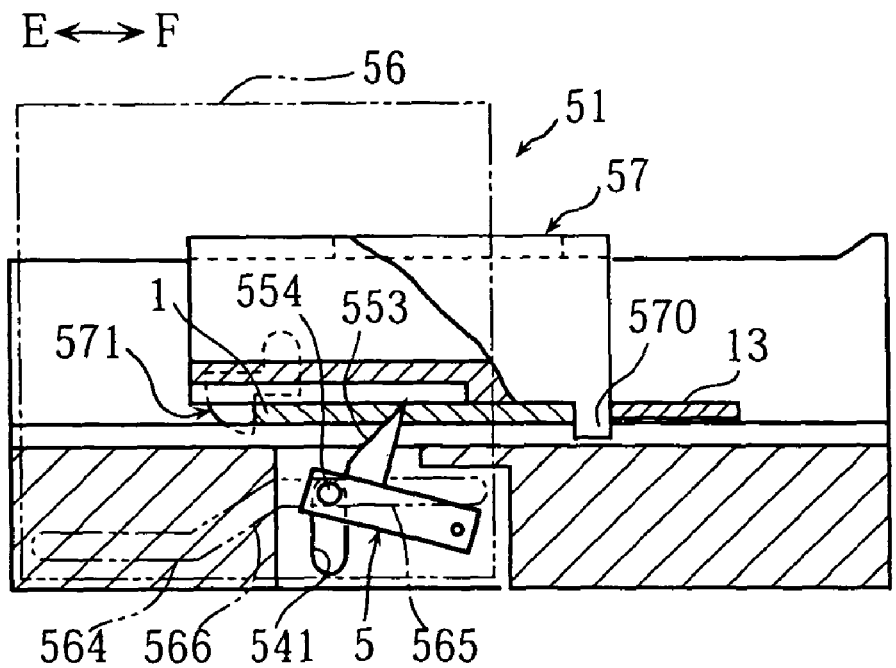
FIGS. 30A and 30B are sectional views showing a principal portion to describe the operation for projecting a biosensor from a sensor pack.

As shown in FIG. 12A, the blade 553 moved upward in the above manner penetrates through the sensor pack 1. The blade 553 then engages the cutout 130 of the biosensor 13. In this state, when the slider 51 is moved relative to the base 50 in the direction indicated by the arrow E in the figures (See FIGS. 29A-29C), the sensor pack 1 moves together with the slider 51 in the arrow E direction, because the sensor pack 1 is held by the front hooks 570 and the rear hooks 571, as shown in FIG. 30. During this movement, the shaft portion 554 is positioned in the second straight movement portion 565, so that the blade 553 of the movable cutter 55 is kept at the top dead center. As a result, the engagement of the blade 553 with the biosensor 13 is maintained, so that the biosensor 13 moves relative to the sensor pack 1 (relative to the sealing sheets 12a, 12b and the base film 14, to be exact) in the direction indicated by the arrow F.

As a result, as shown in FIG. 12B, the biosensor 13 projects through the slit 15 previously formed in the sensor pack 1. Since the distance between the paired front hooks 570 is larger than the width of the biosensor 13, the biosensor 13 projects from between the front hooks 570. Since the front end of the biosensor 13 is rounded, the projecting operation can be performed smoothly. The movement of the biosensor 13 is stopped when the stopper portion 131 of the biosensor 13 engages the stopper portion 146 of the sensor pack 1. Thus, the plurality of through-holes 138, and hence, the electrodes 134-136 of the biosensor 13 are exposed to the outside. In this embodiment, the exposed area of each electrode 134-136 is made as small as possible by the provision of the through-holes 138. Therefore, the electrodes 134-136 of the biosensor 13 projecting from the slit are prevented from coming into contact with the nearby portion of the slit 15 of the sealing sheet 12a, whereby short circuiting between the electrodes 134-136 are prevented.

Figure 30B:
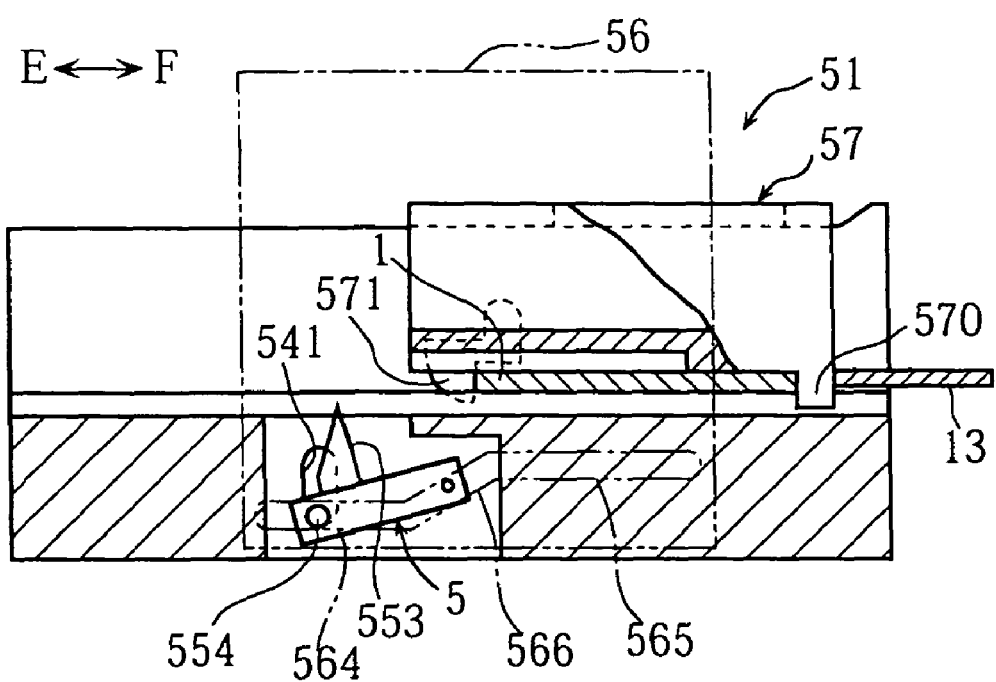

As shown in FIG. 30B, when the slide guide 56 is moved in the arrow F direction in the figure, the shaft portion 554 moves from the second straight movement portion 565 toward the first straight movement portion 564 through the up/down movement portion 566, whereby the blade 553 of the movable cutter 55 moves downward. At this time, the entirety of the sensor pack 1 including the biosensor 13 moves in the arrow F direction, so that the biosensor 13 projects from the measurement mechanism 5, and hence, from an opening 29 of the device body 2 shown in FIGS. 1 and 2. As will be understood from FIG. 18A, to the biosensor 13 in this state, the sample liquid is supplied through the sample introduction port 181 for performing analysis of the sample liquid.

Figure 31:
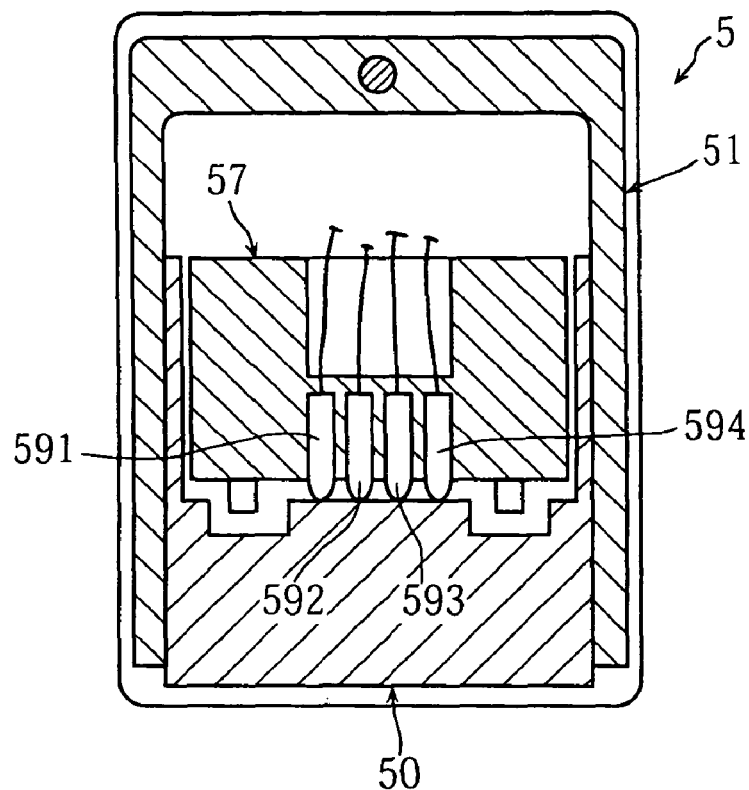
FIG. 31 is a sectional view showing a principal portion of a measurement mechanism.

As shown in FIG. 31, four probes 591-594 are fixed to the slider block 57. As shown in FIG. 18B, the probes 591-594 are so arranged as to come into contact with the electrodes 134-136, respectively, through the through-holes 138 when the biosensor 13 is in the state shown in FIG. 12B. With this arrangement, a voltage can be applied to the reagent layer 137 shown in FIGS. 17 and 18A, and the responsive current can be measured. Based on the responsive current, analysis of the sample (e.g. computation of the concentration of a particular component in the sample liquid) can be performed, or the introduction of the sample liquid into the flow path 133 can be detected.

Figure 27:
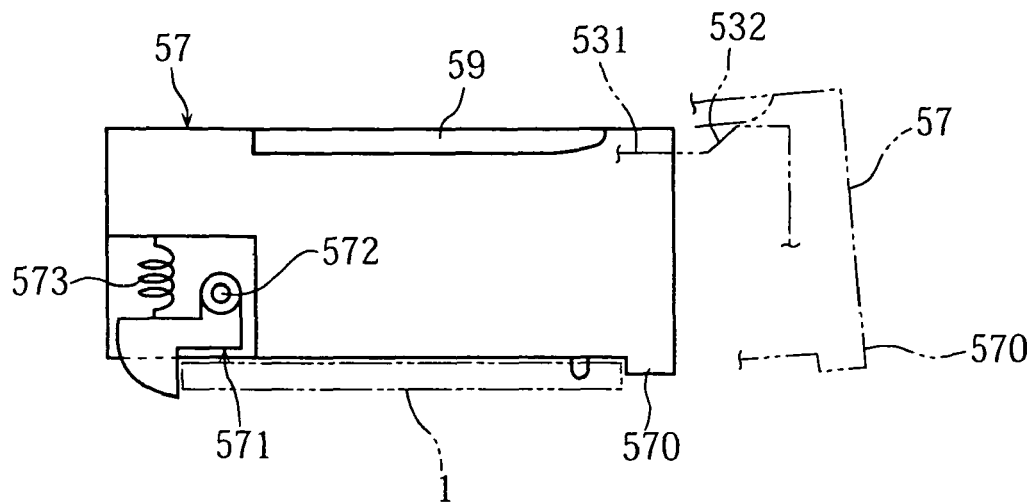
FIG. 27 is a front view of a slide block.
Figure 32:
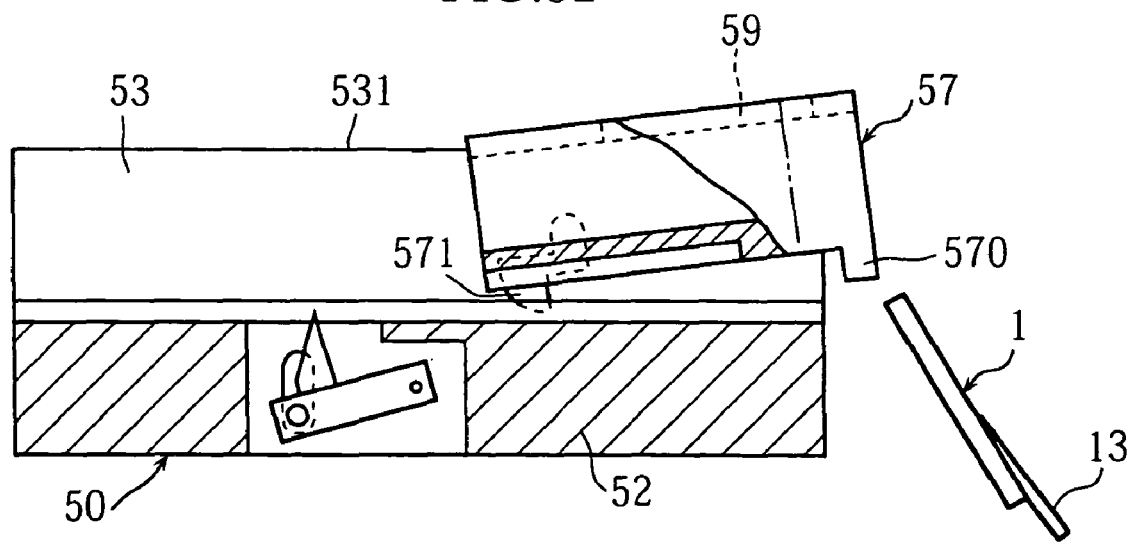
FIG. 32 is a sectional view showing a principal portion to describe the operation for discharging a sensor pack from the measurement mechanism.

As shown in FIGS. 24 and 27, the upper end of the slider block 57 is formed with a pair of flanges 59 projecting width wise outward of the slider block 57. Each of the flanges 59 slides on the upper surface 531 of the corresponding side wall 53 of the base 50 when the slider block 57 (slider 51) moves relative to the base 50. As noted above, a tapered portion 532 is formed at an end of the upper surface 531. Therefore, as shown in FIGS. 27 and 32, when the flange 59 rides on the tapered portion, the end of the slider block 57 (slider 51) is lifted relative to the base 50. As a result, the engagement between the front hooks 570 and the sensor pack 1 is released, whereby the sensor pack 1 together with the biosensor 13 is released from the measurement mechanism 5, or from the opening 29 (See FIGS. 1 and 2) of the device body 2. In the analyzer X, the entirety of the biosensor 13 may be accommodated again in the sensor pack 1 before the disposal of the sensor pack 1. In this case, the user can dispose of the biosensor without touching the biosensor 1 (particularly blood), which is preferable from a hygienic point of view.

As described above, since the front end of the biosensor need not be made sharp, the user does not feel fear and is not hurt by the biosensor 13. The sensor pack 1 after the analysis can be disposed of together with and at the same time as the biosensor 13. Therefore, the number of parts to be disposed of is small, and the sensor pack 1 can be disposed of with little trouble.

Next, a second embodiment of the present invention will be described below with reference to FIGS. 33-40. In FIGS. 33-40, elements which are identical or similar to those of the first embodiment described above are designated by the same reference signs, and the description thereof is omitted below.

Figure 33:
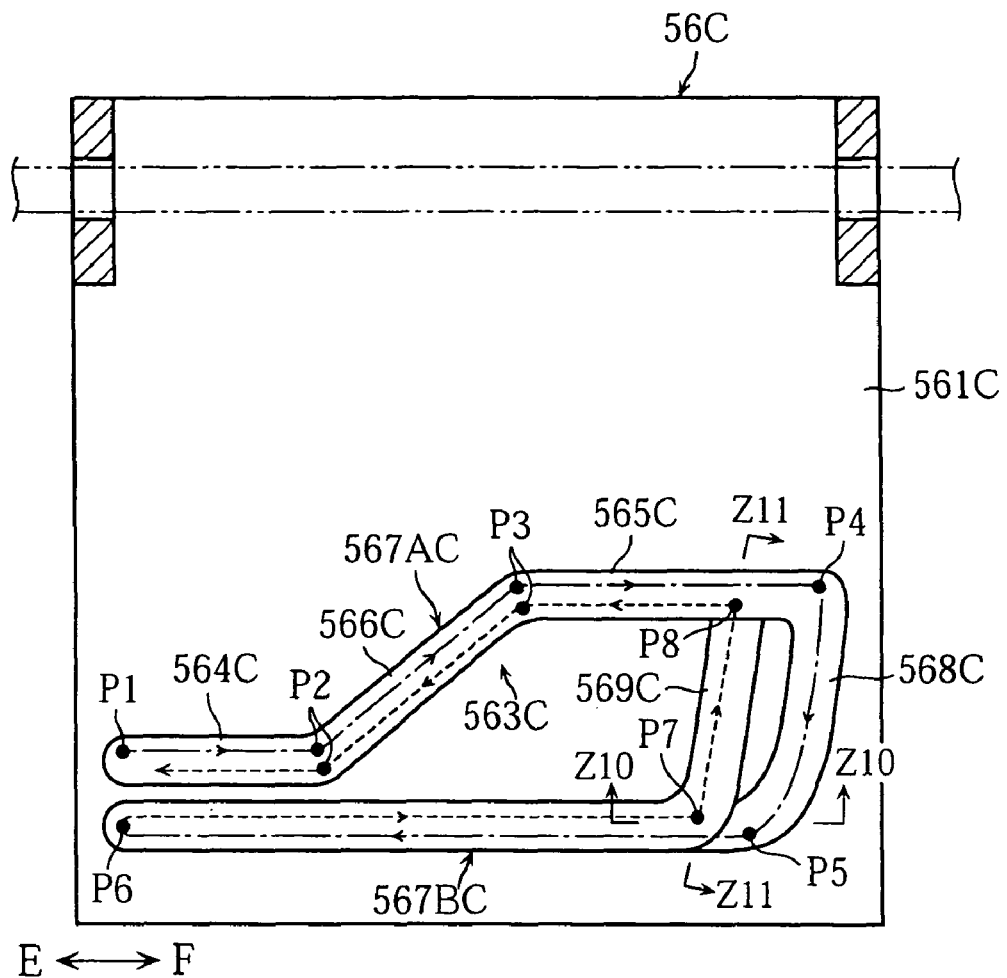
FIG. 33 is a sectional view showing a slide guide of a measurement mechanism according to a second embodiment of the present invention.

As shown in FIG. 33, the slide guide 56C of the measurement mechanism of the analyzer includes a side wall 561C formed with a non-penetrating cam groove 563C. The cam groove 563C includes an upper groove portion 567AC, a lower groove portion 567BC, a downward movement groove portion 568C connecting between the groove portions 567AC and 567BC, and an upward movement groove portion 569C.

The upper groove portion 567AC includes a first and a second straight movement portions 564C and 565C which differ from each other in height position, and an up/down movement portion 566C connecting between the straight movement portions 564C and 565C. As will be understood from FIGS. 33-35, the first and the second straight movement portions 564C, 565C and the up/down movement portion 566C have the same depth.

The lower groove portion 567BC extends below the first and the second straight movement portions 564C, 565C and in parallel with the first and the second straight movement portions 564C, 565C. The lower groove portion 567BC has a uniform depth which is generally equal to that of the upper groove portion 567AC.

Figure 34:
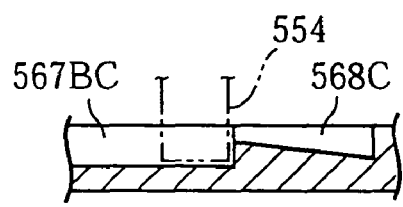
FIG. 34 is a sectional view taken along lines Z10-Z10 in FIG. 33.
Figure 35:
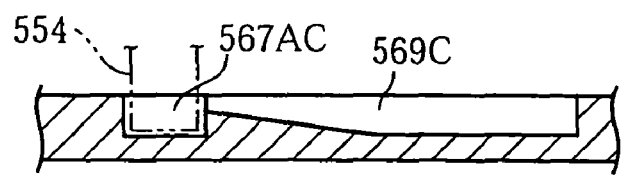
FIG. 35 is a sectional view taken along lines Z11-Z11 in FIG. 33.

The downward movement portion 568C connects an end of the upper groove portion 567AC and an end of the lower groove portion 567BC to each other, and the part of the downward movement portion connected to the end of the lower groove portion 567BC is smaller in depth than the lower groove portion 567BC, as better shown in FIG. 34.

As shown in FIG. 33, the upward movement portion 569C connects the upper groove portion 567AC and the lower groove portion 567BC to each other at a position deviated from the downward movement portion 568C in the arrow E direction. As better shown in FIG. 35, the part of the upward movement portion 569C connected to the upper groove portion 567AC is smaller in depth than the upper groove portion 567AC.

Figure 37A:
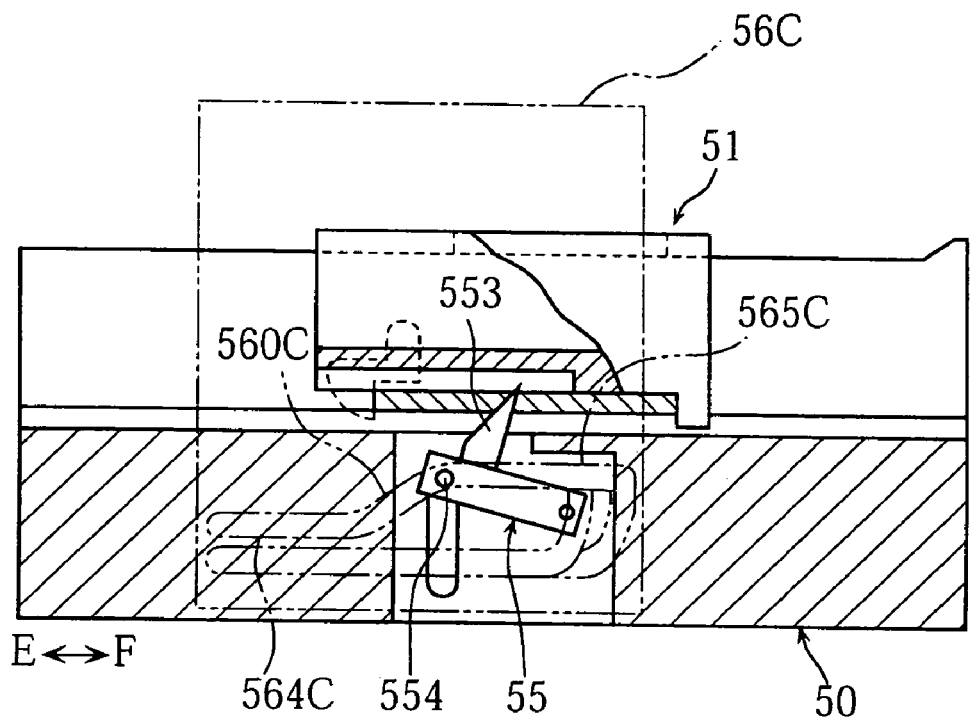

As will be understood from e.g. FIG. 37A, the cam groove 563C receives the shaft portion 554 of the movable cutter 55. Therefore, by moving the slide guide 56C, the position of the shaft portion 554 in the cam groove 563C changes. As a result, the movable cutter 55 pivots so that the height position of the movable cutter 55 changes. In the cam groove 563C having the above configuration, it is preferable that the shaft portion 554 is biased toward the side wall 561C.

Figure 36:
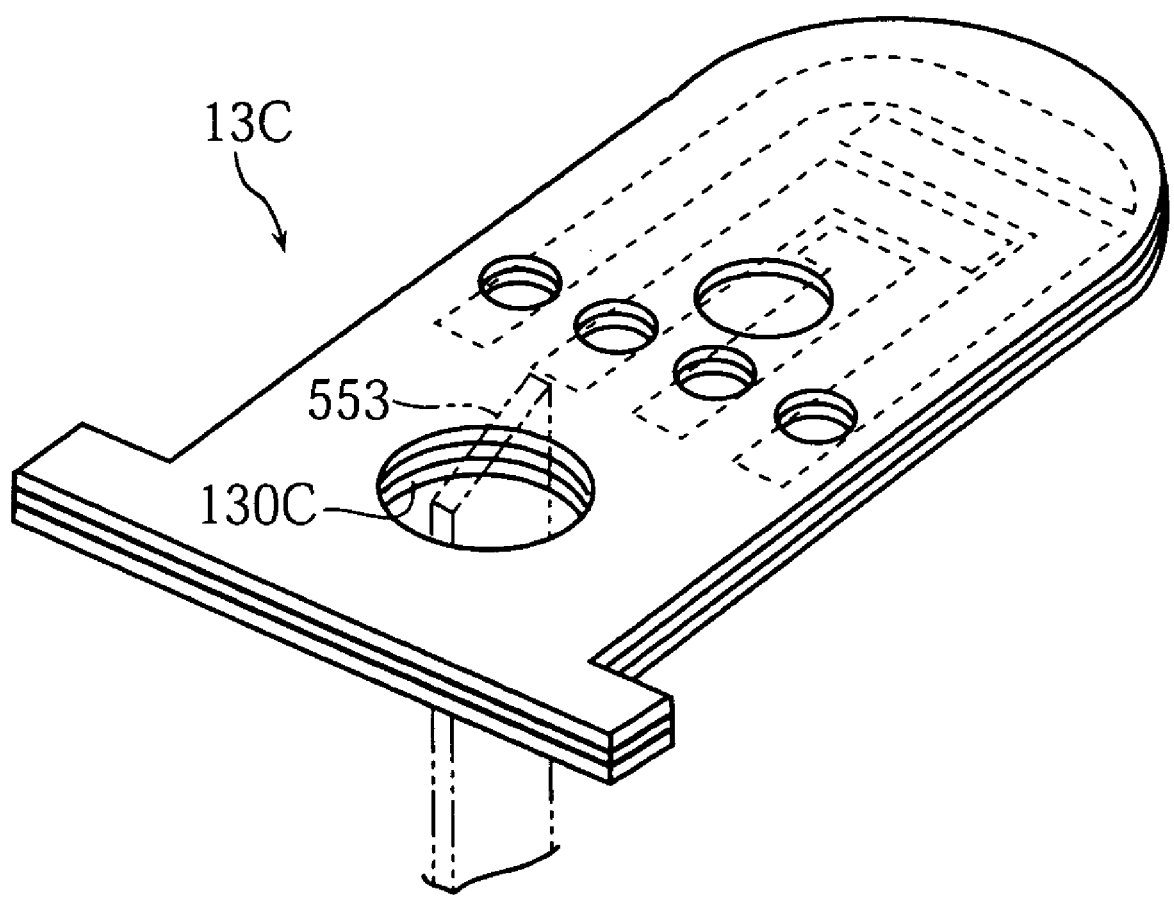
FIG. 36 is an entire perspective view of a biosensor.

In this embodiment, a biosensor 13C as shown in FIG. 36 is used, for example. The illustrated biosensor 13C is similar in basic structure to the biosensor 13 (See FIG. 16) used in the first embodiment but differs from the biosensor 13 in structure for engagement with the blade 553 of the movable cutter 55. Specifically, the portion for engagement with the blade 553 comprises a through-hole 130C.

In this embodiment, the slide guide 56C is caused to reciprocate twice in the arrow EF direction in the figure in a single sample analysis operation (See FIG. 33). Specifically, the first reciprocal movement is performed to cause the biosensor 13 to project from the slit 15 of the sensor pack 1C similarly to the first embodiment (See FIG. 38B), whereas the second reciprocal movement is performed to pull the biosensor 13C into the sensor pack 1C to accommodate the biosensor 13C again (See FIG. 40B).

As shown in FIG. 33, the movement route of the shaft portion 554 (See e.g. FIG. 37A) of the movable cutter 55 in the cam groove 563C differs between the first reciprocal movement (for pushing out the biosensor 13C (See FIG. 38B)) and the second reciprocal movement (for accommodating the biosensor 13C again (See FIG. 40B)). Thus, the blade 553 of the movable cutter 55 operates differently between the first reciprocal movement and the second reciprocal movement. In FIG. 33, the movement route of the shaft portion 554 in the first reciprocal movement is indicated by a single dashed line, whereas the movement route of the shaft portion 554 in the second reciprocal movement is indicated by a chain line.

In the first reciprocal movement, the shaft portion 554 (See e.g. FIG. 37A) starts from the point P1 and pass through the points P2-P5 before reaching the point P6.

Specifically, when the slide guide 56C moves in the arrow E direction, the shaft portion 554 moves through the first straight movement portion 564C, the up/down movement portion 566C, and the second straight movement portion 565C, similarly to the first embodiment. It is to be noted that, when the shaft portion 554 reaches the point P8, the shaft portion does not enter the upward movement portion 569C but moves straight in the arrow F direction to reach the point P4, because the second straight movement portion 565C is larger in depth than the part of the upward movement portion 569C connected to the second straight movement portion 565C.

As will be understood from FIG. 37A, when the shaft portion 554 is positioned in the first straight movement portion 564C (between the points P1 and P2), the blade 553 of the movable cutter 55 is located at a first bottom dead center. When the slide guide 56C is moved in the arrow E direction to move the shaft portion 554 from the first straight movement portion 564C toward the second straight movement portion 565C through the up/down movement portion 566C (between the points P2 and P3), the blade 553 of the movable cutter 55 moves upward. When the shaft portion 554 reaches the second straight movement portion 565C (point P3), the blade 553 is positioned at the top dead center.

Figure 37B:
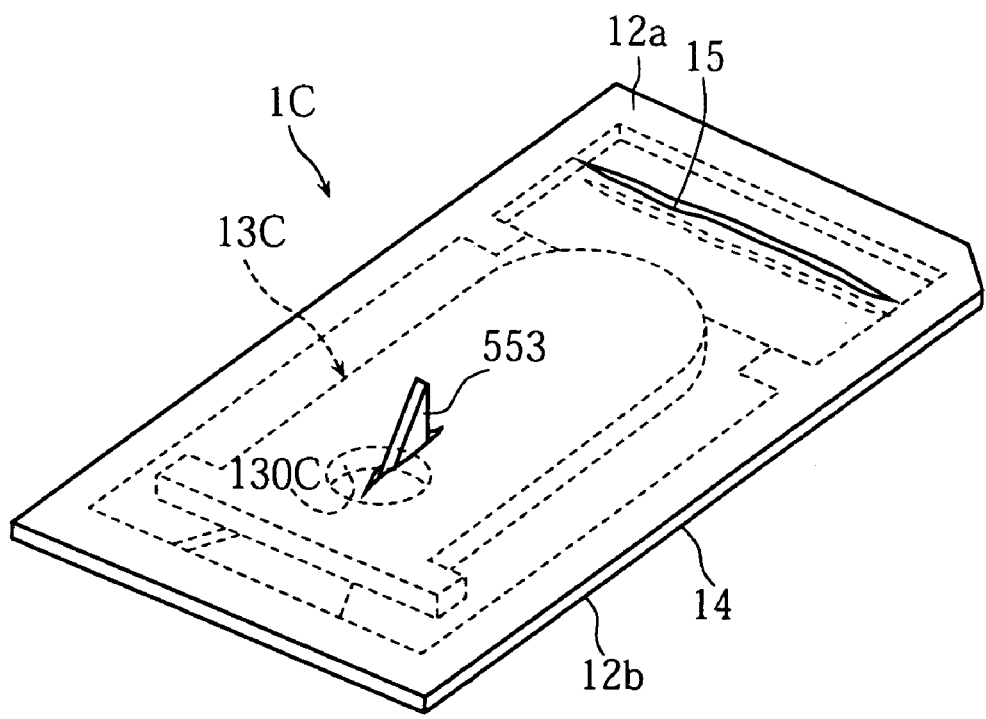
FIG. 37B is an entire perspective view showing a biosensor which is being fed.
Figure 38A:
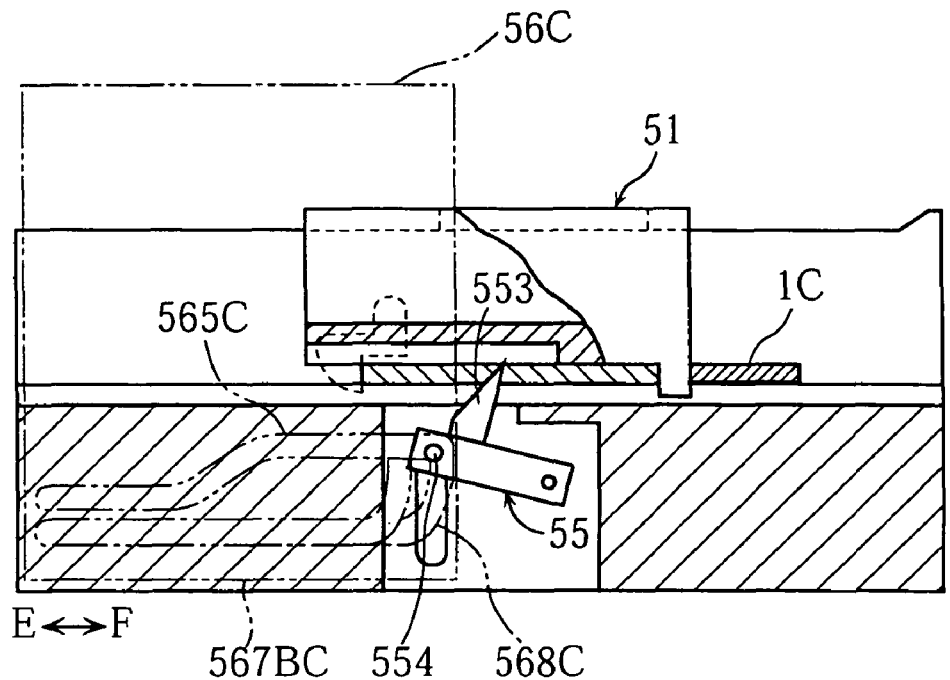
Figure 38B:
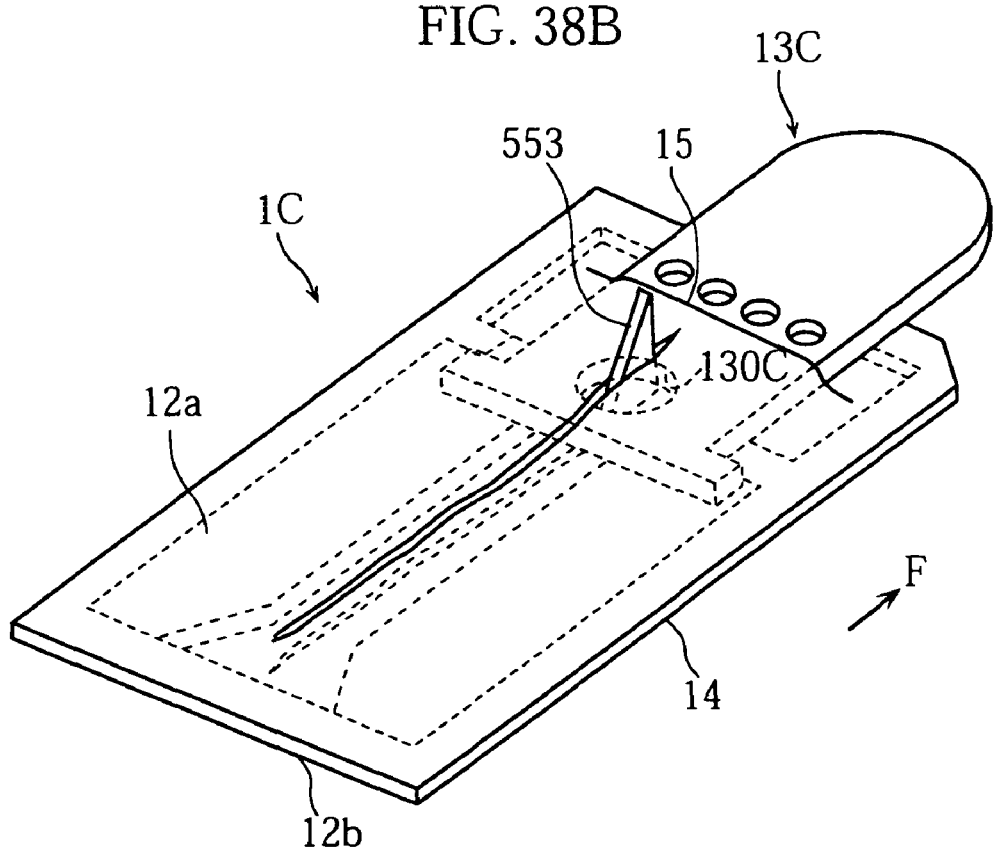
FIG. 38B is an entire perspective view showing a biosensor which is being fed.

As shown in FIG. 37B, the blade 553 moved upward in the above manner penetrates through the sensor pack 1C and is inserted into the through-hole 130C of the biosensor 13C for engagement with the inner surface of the through-hole 130C. In this state, when the slider 51 is moved relative to the base 50 in the direction indicated by the arrow E in the figures, the sensor pack 1C moves together with the slider 51 in the arrow E direction, as shown in FIGS. 38A and 38B. During this movement, the shaft portion 554 is positioned in the second straight movement portion 565C, so that the blade 553 is kept at the top dead center. As a result, as better shown in FIG. 38B, the engagement of the blade 553 with the through-hole 130C of the biosensor 13C is maintained, so that the biosensor 13 moves relative to the sensor pack 1 (relative to the sealing sheets 12a, 12b and the base film 14, to be exact) in the direction indicated by the arrow F. As a result, the biosensor 13C projects from the slit 15 of the sensor pack 1C.

With the biosensor 13C projecting from the sensor pack 1C, a sample is supplied to the biosensor 13C, whereby the concentration of a particular component in the sample is computed, similarly to the above-described first embodiment.

Unlike the first embodiment, when the slide guide 56C moves in the arrow F direction, the shaft portion 554 moves through the downward movement portion 568C (between the points P4 and P5) to move to a lower position and then moves straight through the lower groove portion 567BC (between the points P5 and P6) to reach the point P6, as will be understood from FIG. 33.

Figure 39A:
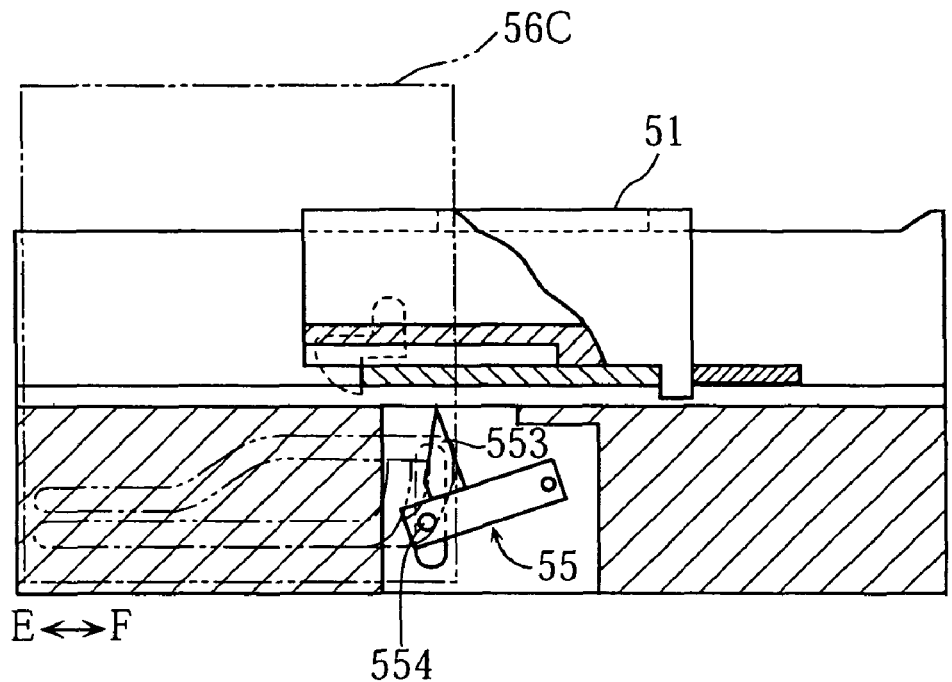

As can be seen from FIGS. 38A and 39A, when the slide guide 56C moves through the downward movement portion 568C (between the points P4 and P5 in FIG. 33), the blade 553 of the movable cutter 55 moves downward. When the shaft portion 554 reaches the lower groove portion 567BC (the point P5 in FIG. 33), the blade 553 is positioned at a second bottom dead center.

Figure 39B:
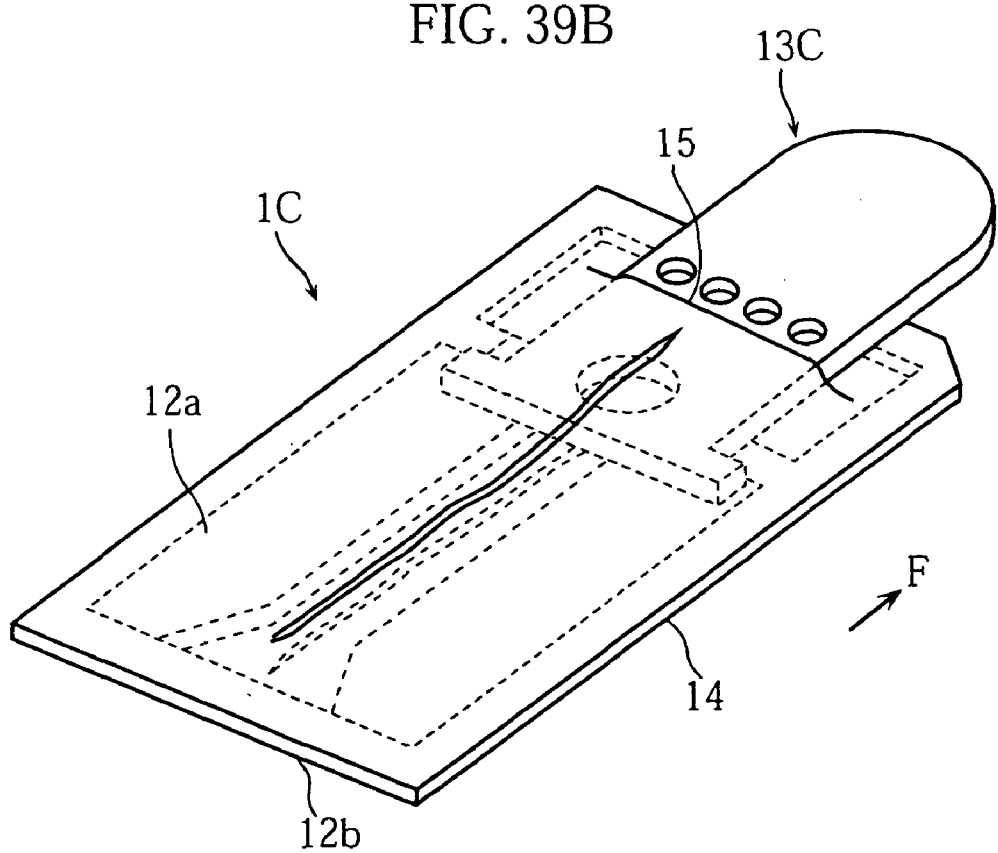
FIG. 39B is an entire perspective view showing a biosensor in the escaping movement.
Figure 40A:
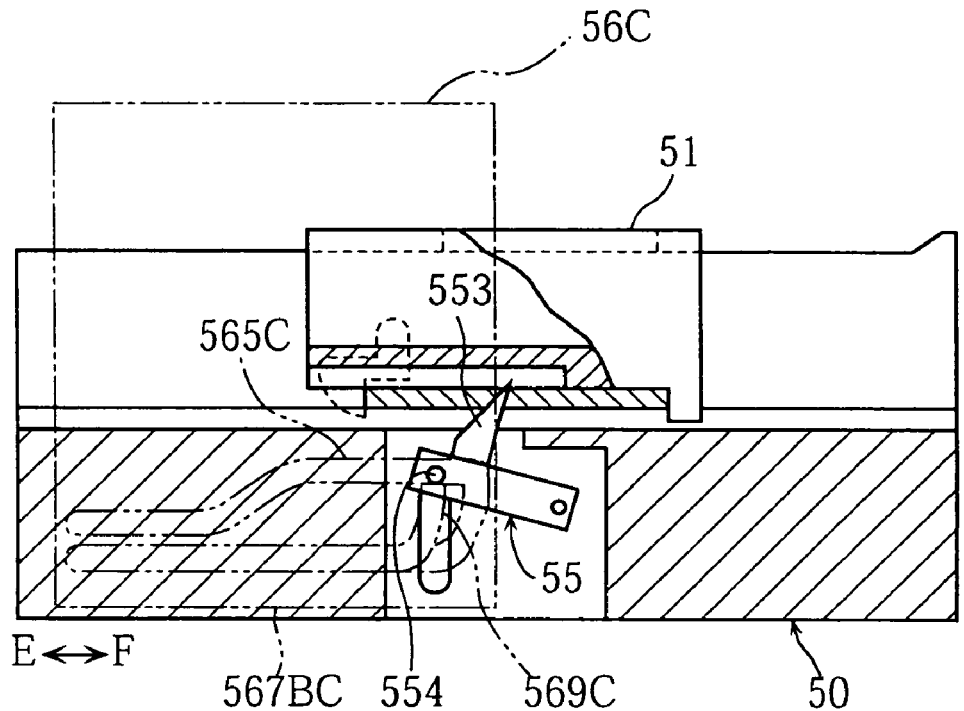
Figure 40B:
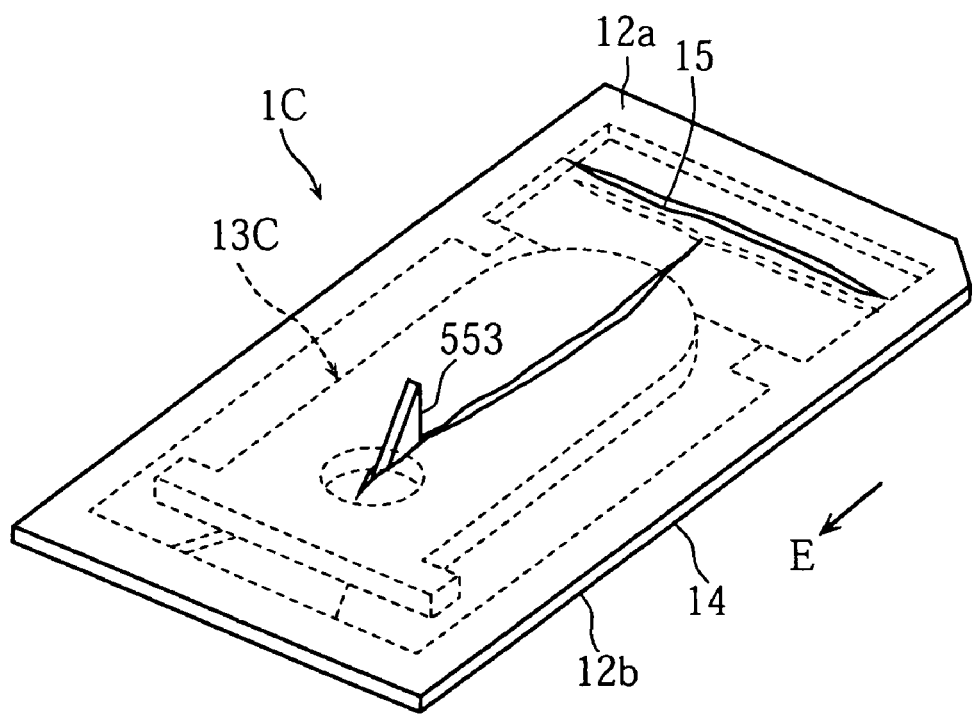
FIG. 40B is an entire perspective view showing the biosensor in the returning movement.

By moving the blade 553 downward in the above manner, the blade 553 is pulled out from the sensor pack 1C, as shown in FIGS. 39A and 39B. In this state, when the slide guide 56C is moved in the arrow F direction in the figure, the shaft portion 541 moves straight through the lower groove portion 567BC (between the points P5 and P6 in FIG. 33) while keeping the blade 553 at the bottom dead center.

In the second reciprocal movement, the shaft portion 554 (See e.g. FIG. 37A) starts from the point P6 and pass through the points P7, P8 and P2 to reach the point P1, as shown in FIG. 33.

Specifically, when the slide guide 56C moves in the arrow E direction, the shaft portion 554 moves straight through the lower groove portion 567BC from the point P6 toward the point P7, and then moves through the upward movement portion 569C (P7, P8) to reach the point P8. It is to be noted that, when the shaft portion 554 reaches the point P7, the shaft portion does not enter the downward movement portion 568C but moves through the upward movement portion 569C, because the upward movement portion 569C is larger in depth than the part of the downward movement portion 568C connected to the lower groove portion 567BC (See FIG. 34).

As will be understood from FIGS. 33 and 39A, when the shaft portion 554 is located in the lower grove portion 567BC (between the points P6 and P7), the blade 553 of the movable cutter 55 is located at the second bottom dead center. When the shaft portion 554 moves through the upward movement portion 569C (between the points P7 and P8), the blade 553 of the movable cutter 55 moves upward. When the shaft portion 554 reaches the second straight movement portion 565C (the point P8), the blade 553 is positioned at the top dead center.

The blade 553 moved upward in the above manner is inserted again into the through-hole 130C of the biosensor 13C for engagement with the inner surface of the through-hole 130C (See FIG. 38B). In this state, when the slider 51 is moved relative to the base 50 in the direction indicated by the arrow F in the figures, the sensor pack 1C moves together with the slider 51 in the arrow F direction. During this movement, the shaft portion 541 is positioned in the second straight movement portion 565C, so that the blade 553 is kept at the top dead center. As a result, as better shown in FIG. 40B, the engagement of the blade 553 with the through-hole 130C of the biosensor 13C is maintained, so that the biosensor 13C moves relative to the sensor pack 1C (relative to the sealing sheets 12a, 12b and the base film 14, to be exact) in the direction indicated by the arrow E. As a result, the biosensor 13C is accommodated again in the sensor pack 1C.

Similarly to the first embodiment, when the slide guide 56C moves in the arrow F direction, the shaft portion 554 moves through the second straight movement portion 565C, the up/down movement portion 566C and the first straight movement portion 564C. In this process, the blade 553 of the movable cutter 55 moves from the top dead center to the first bottom dead center. Thus, the blade 553 is pulled out from the sensor pack 1C to become a state similar to that shown in FIG. 39B.

After the biosensor 1C is accommodated again, the slider 51 is moved relative to the base 50 in the arrow E direction in the figure, whereby the sensor pack 1C is disposed of in a manner similar to that in the first embodiment.

In this embodiment, the sensor pack 1C after use is disposed of with the biosensor 1C accommodated in the sensor pack. Therefore, the biosensor 13C can be disposed of integrally with the wrapping member, which reduces the number of parts to be disposed of and which is preferable from a hygienic point of view.

Figure 41:
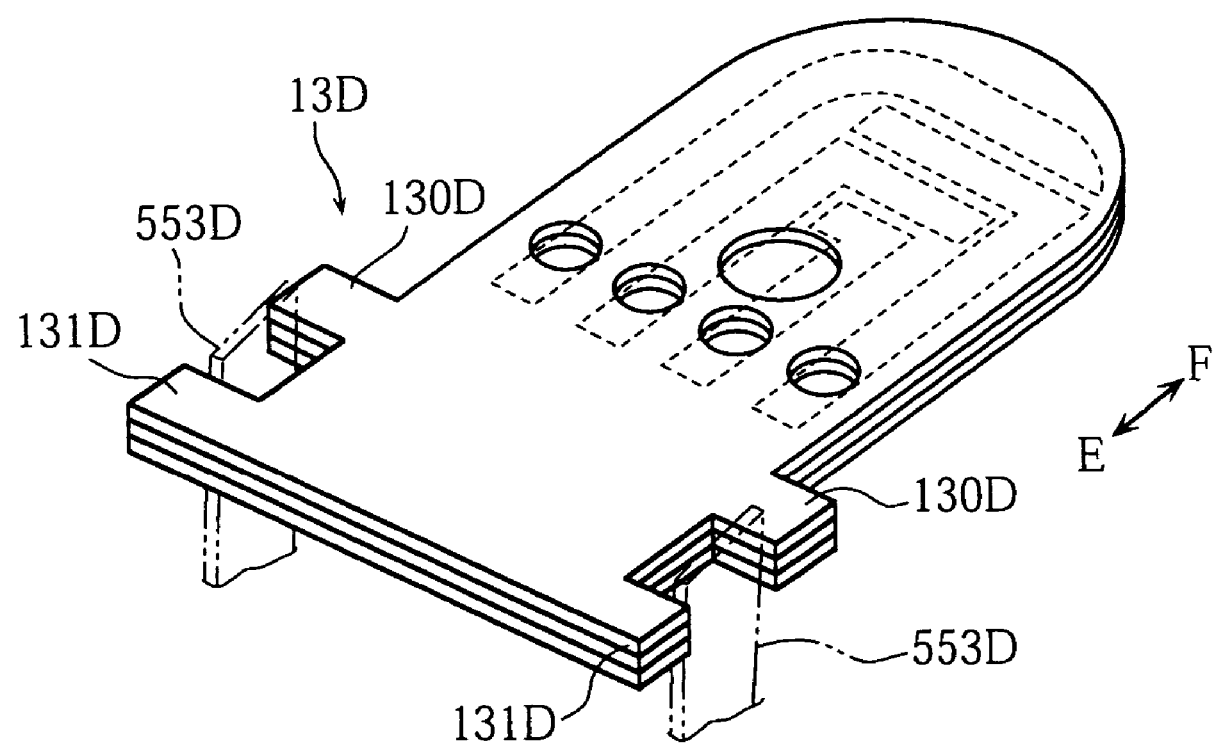
FIG. 41 is an entire perspective view showing another example of biosensor which can be used in the second embodiment.

As the biosensor for providing the sensor pack, use may be made of a biosensor 13D shown in FIG. 41. In the biosensor 13D, the portion for engagement with the blade 553D of the movable cutter in moving the biosensor 13 is provided at opposite sides of the biosensor 13D. Specifically, the biosensor 13D has opposite side edges each of which is provided with a pair of projections 130D, 131D. A blade 553D is inserted between the projections 130D and 131D for engagement with the projections 130D, 131D.

The projection 130D serves to engage with the blade 553D when the biosensor 13D is moved in the arrow F direction, and also serve as a stopper for preventing the movement of the biosensor 13D relative to the sealing sheets or the base film of the sensor pack. The projection 131D serves to engage with the blade 553D when the biosensor 13D is moved in the arrow F direction.

When the biosensor 13D is utilized, two blades 553 need be provided in the measurement mechanism.

The present invention is not limited to the first and the second embodiments described above, and may be modified in various ways. For example, the sensor pack and the biosensor may have structures as shown in FIGS. 42-44.

Figure 42:
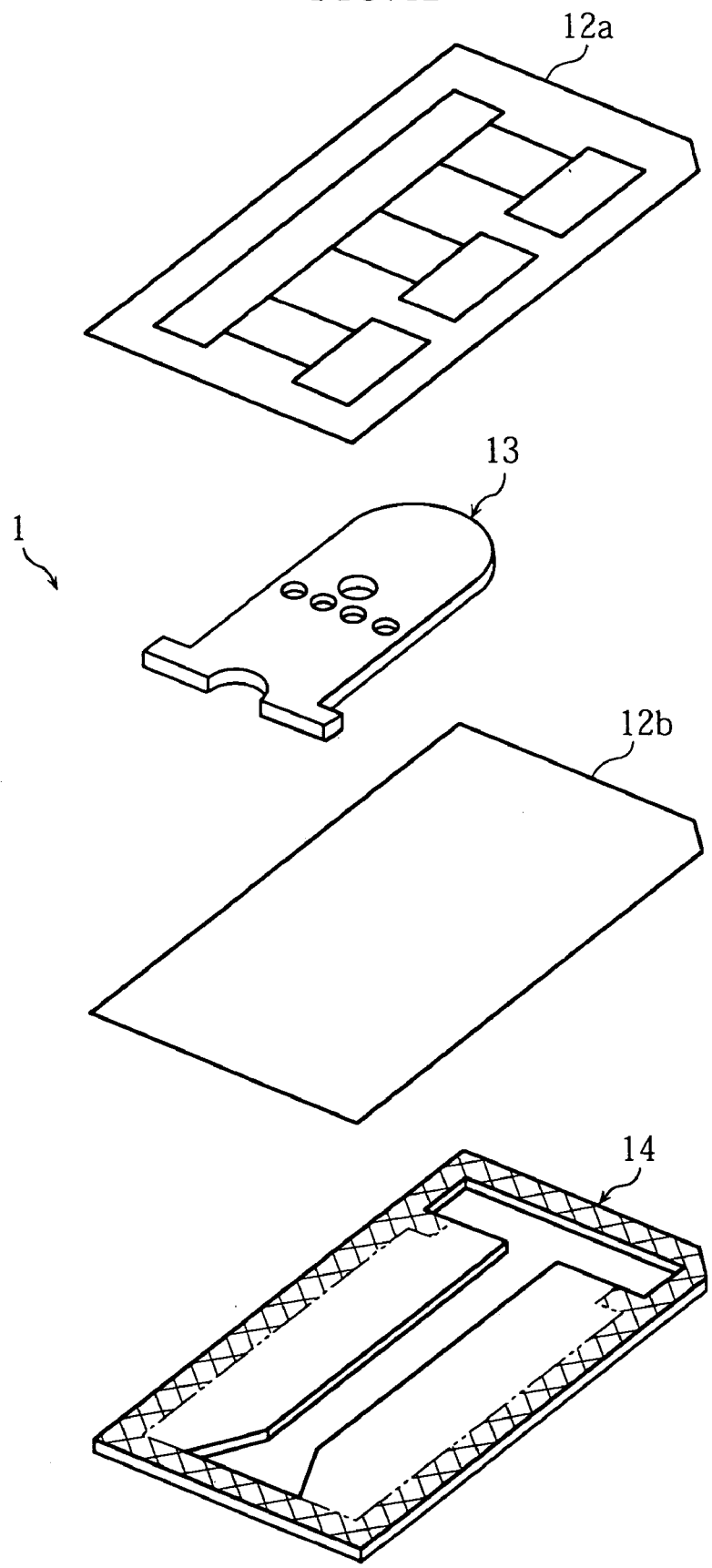
FIG. 42 is an exploded perspective view showing another example of sensor pack.

The sensor pack 1 shown in FIG. 42 includes a base film 14, a sealing sheet 12b, a biosensor 13 and a sealing sheet 12a which are stacked in the mentioned order.

Figure 43B:
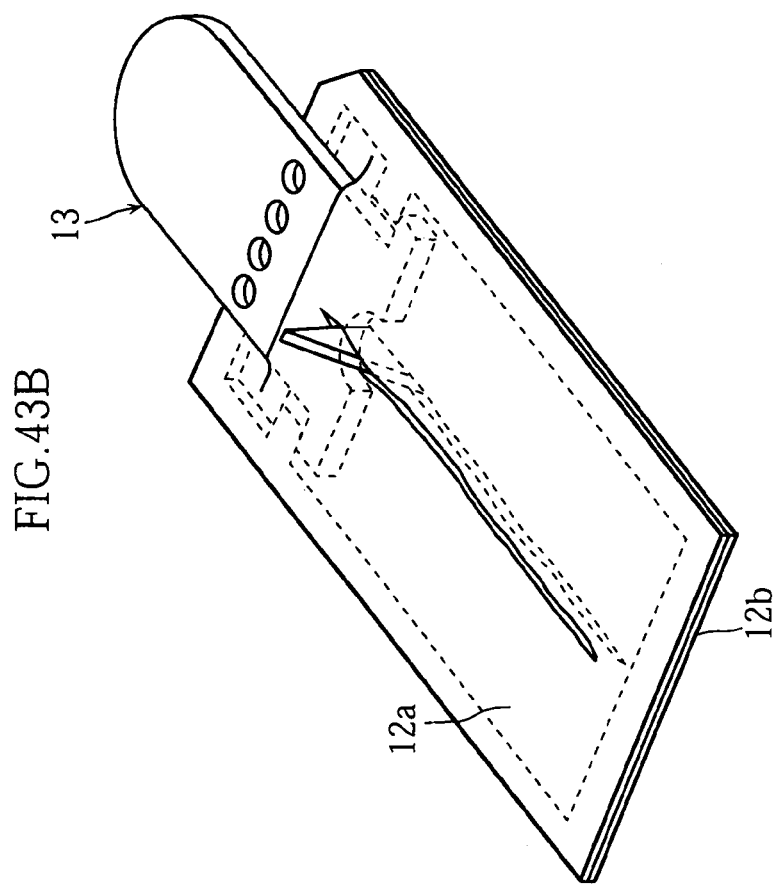
FIGS. 43A and 43B are an exploded perspective view and an entire perspective view, respectively, for describing another example of sensor pack.
Figure 43A:
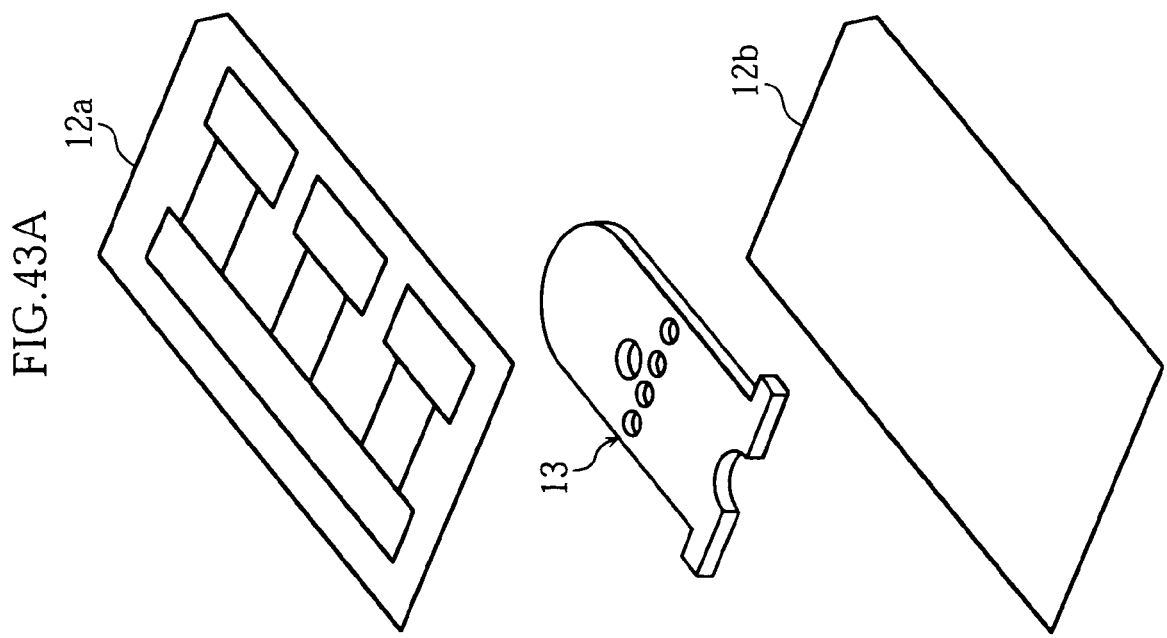

The sensor pack shown in FIGS. 43A and 43B does not include a base film, and the biosensor is enclosed only by the sealing sheets 12a, 12b.

Figure 44:
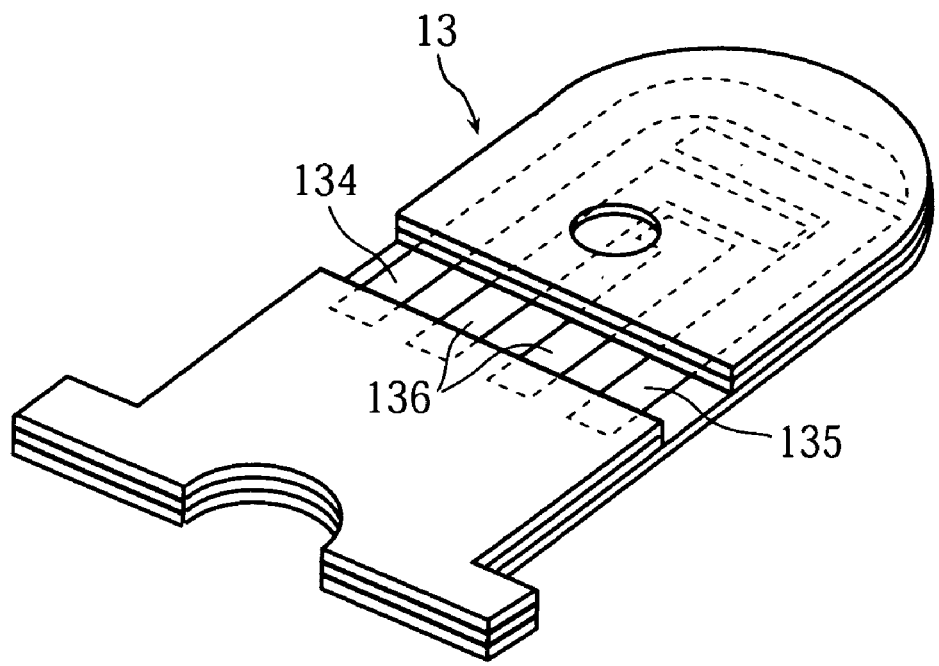
FIG. 44 is an entire perspective view showing another example of biosensor.
Figure 45:
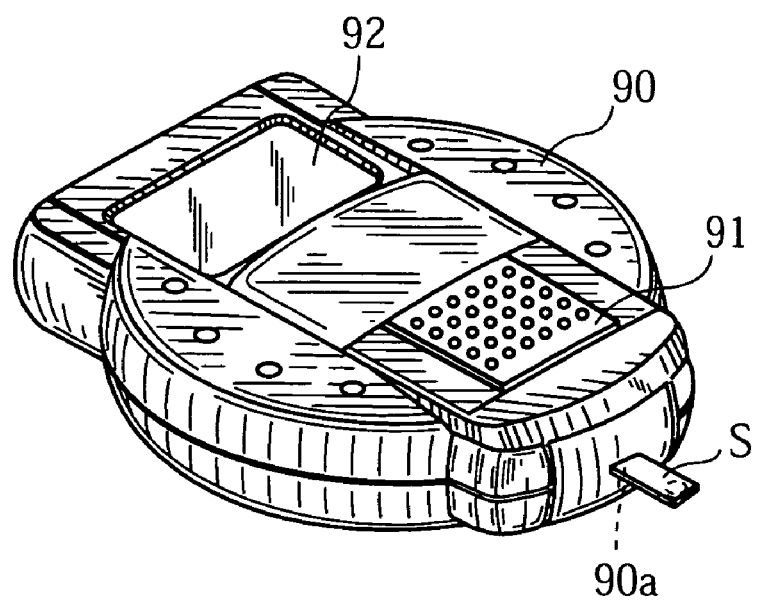
FIG. 45 is a perspective view showing the appearance of an example of prior art measurement device.
Figure 46:
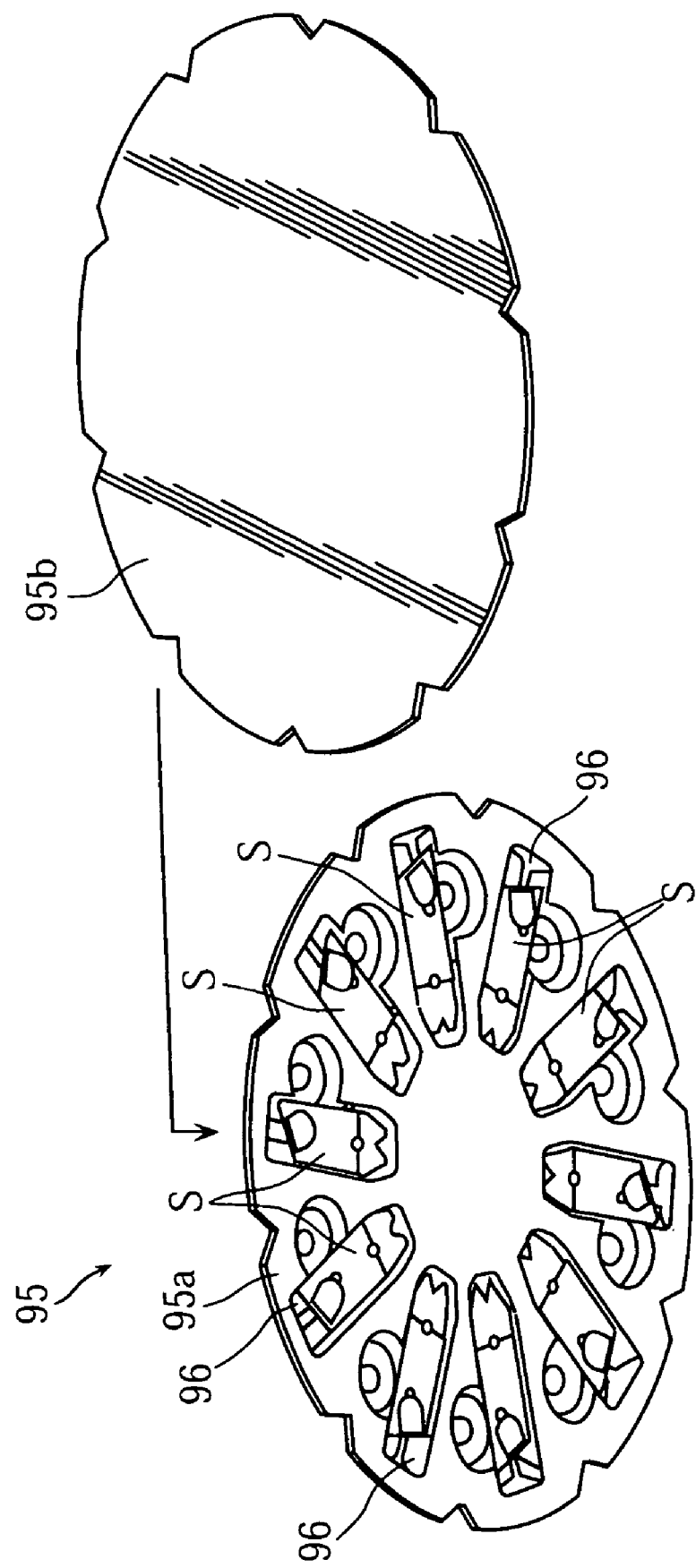
FIG. 46 is a perspective view showing an example of prior art cartridge and film for covering a sensor.
Figure 47A:
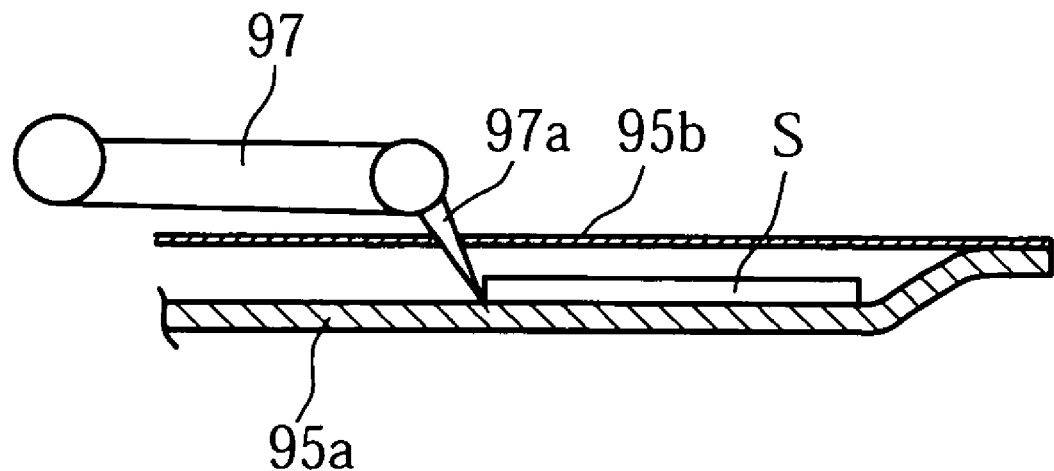
FIGS. 47A and 47B show the operation of a prior art measurement device.
Figure 47B:
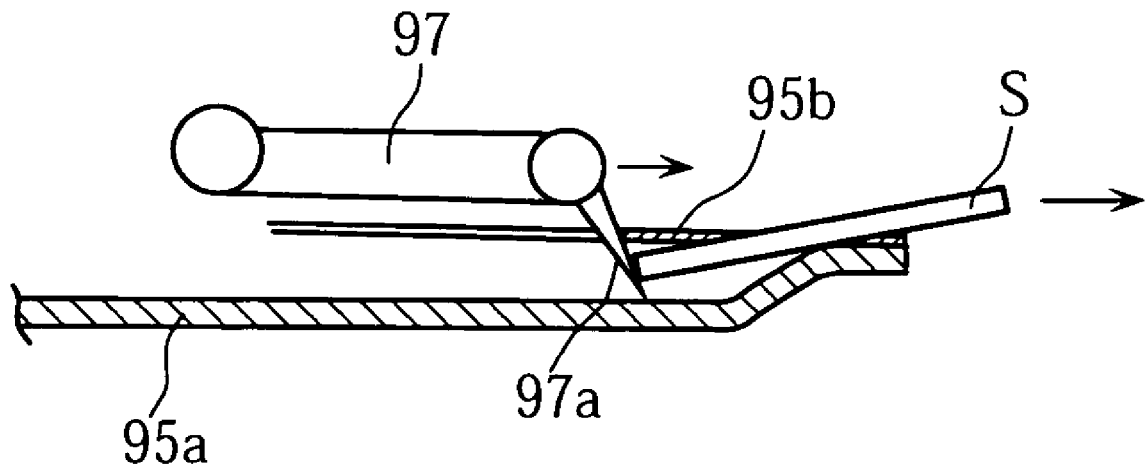

In the biosensor 13 shown in FIG. 44, the electrodes 134-136 are exposed continuously.

The opening mechanism of the first embodiment can be used not only for opening the sensor pack in the analyzer but also for various purposes. For example, when a wrapping member contains an object in a solid state other than a biosensor or an object in a liquid or gel state, the opening mechanism can be used for opening the wrapping member to take out the content. The content may be taken out by a method similar to that of the above analyzer when the content is in a solid state. Alternatively, the content may be taken out by squeezing out with the use of a roller, regardless of the state of the content.

The invention claimed is: comprising an information providing portion for outputting

1. An analytical tool pack comprising an analytical tool accommodated in a wrapping member made of a sealing sheet,
   wherein the analytical tool pack further comprises a stopper portion for holding the analytical tool in a manner such that the analytical tool projects from the wrapping member; and
   wherein the wrapping member further comprises a base film bonded to the sealing sheet to define a space between the base film and the sealing sheet for accommodating the analytical tool, the base film including a first guide groove penetrating through the base film and extending in a first direction, the base film further including a second guide groove penetrating through the base film and extending in a second direction crossing the first direction.

2. The analytical tool pack according to claim 1, wherein the stopper portion comprises a bonded portion of the sealing sheet and the base film.

3. The analytical tool pack according to claim 1, wherein the analytical tool includes an engagement portion engaging with the stopper portion.

4. The analytical tool pack according to claim 1, wherein the sealing sheet retains desiccant.

5. The analytical tool pack according to claim 1, wherein the base film retains desiccant.

6. The analytical tool pack according to claim 1, wherein the analytical tool is caused to project through a cut formed in the sealing sheet by a cutter; and
   wherein the first guide groove of the base film allows insertion of the cutter.

7. The analytical tool pack according to claim 1, wherein the analytical tool includes an end which is caused to project through a cut formed in the sealing sheet by a cutter inserted through the first guide groove of the base film; and
   wherein the end is entirely rounded.

8. The analytical tool pack according to claim 1, wherein the analytical tool is moved relative to the wrapping member by a pushing member; and
   wherein the second guide groove of the base film allows movement of the pushing member.

9. The analytical tool pack according to claim 1, wherein the analytical tool is moved relative to the wrapping member by a pushing member inserted through the second guide groove of the base film; and
   wherein the analytical tool further includes an engagement portion for engaging the pushing member.

10. The analytical tool pack according to claim 1, wherein the analytical tool includes a substrate, a plurality of electrodes formed on the substrate, and a plurality of holes each for partially exposing a respective one of the electrodes selectively.

11. The analytical tool pack according to claim 1, further comprising an information providing portion for outputting information relating to the analytical tool.

12. The analytical tool pack according to claim 11, wherein the information providing portion is capable of outputting information by combination of conduction/non-conduction between a plurality of pairs of conductors, or by correlation with a resistance between conductors, or by correlation with locations where a projection and a recess are formed.

13. The analytical tool pack according to claim 1, wherein the analytical tool pack in use is loaded in an accommodation portion of an analyzer, and wherein a pack orientation checker is provided for preventing improper loading of the analytical tool into the accommodation portion.

14. The analytical tool pack according to claim 1, wherein the analytical tool caused to project from the wrapping member is restorable into the wrapping member.

15. An analytical tool pack comprising an analytical tool accommodated in a wrapping member made of a sealing sheet,
   wherein the analytical tool pack further comprises a stopper portion for holding the analytical tool in a manner such that the analytical tool projects from the wrapping member, the stopper portion coming into stopping engagement with the analytical tool for preventing the analytical tool from moving completely out of the analytical tool pack and
   wherein the analytical tool includes a substrate, a plurality of electrodes formed on the substrate, and a plurality of holes each for partially exposing a respective one of the electrodes selectively.

16. An analytical tool pack comprising an analytical tool accommodated in a wrapping member made of a sealing sheet, the analytical tool including a substrate,
   wherein the analytical tool pack further comprises a stopper portion for holding the analytical tool in a manner such that the analytical tool projects from the wrapping member; and
   wherein the wrapping member further comprises a base film provided separately from the substrate of the analytical tool and bonded to the sealing sheet to define a space between the base film and the sealing sheet for movably accommodating the analytical tool, the base film including a first guide groove penetrating through an entire thickness of the base film and extending in a first direction, the base film further including a second guide groove penetrating through the entire thickness of the base film and extending in a second direction crossing the first direction.

\* \* \* \* \*